(12) United States Patent
Howard et al.

(10) Patent No.: US 7,601,355 B2
(45) Date of Patent: Oct. 13, 2009

(54) COMPOSITIONS AND METHODS FOR ALTERING IMMUNE FUNCTION

(75) Inventors: Laurence Howard, Vienna (AT); Stephen Miller, Oak Park, IL (US); Brian Shoichet, San Francisco, CA (US); John Irwin, San Rafael, CA (US)

(73) Assignee: Northwestern University, Evanston, IL (US)

( * ) Notice: Subject to any disclaimer, the term of this patent is extended or adjusted under 35 U.S.C. 154(b) by 292 days.

(21) Appl. No.: 11/444,591

(22) Filed: Jun. 1, 2006

(65) Prior Publication Data

US 2007/0041981 A1 Feb. 22, 2007

Related U.S. Application Data

(60) Provisional application No. 60/686,224, filed on Jun. 1, 2005.

(51) Int. Cl.
*A61K 39/395* (2006.01)
(52) U.S. Cl. .................. 424/184.1; 424/138.1; 424/118
(58) Field of Classification Search .................. None
See application file for complete search history.

(56) References Cited

U.S. PATENT DOCUMENTS

| 5,679,347 A | 10/1997 | Porcelli |
| 5,776,427 A | 7/1998 | Thorpe |
| 6,238,676 B1 | 5/2001 | Porcelli |
| 2003/0176377 A1 | 9/2003 | Xiang et al. |
| 2004/0006208 A1* | 1/2004 | Karpusas et al. ............ 530/350 |
| 2004/0191248 A1 | 9/2004 | Goldenberg et al. |
| 2005/0084490 A1 | 4/2005 | Adams |

FOREIGN PATENT DOCUMENTS

WO    2007/053189    5/2007

OTHER PUBLICATIONS

Kuby, Immunology, 1994, p. 1-20.*
Gurunathan et al., J. Immunology, 1998, vol. 161, p. 4563-4571.*
Banchereau and Steinman, "Dendritic cells and the control of immunity" 1998 Nature 392:245.
Banchereau et al., "Molecular control of B-cell immunopoiesis" 1994 Ann. N Y Acad. Sci. 725:22-23.
Burdin et al., "Inability to produce IL-6 is a functional feature of human germinal center B lymphocytes" 1996 J. Immunol. 156:4107.
Cohen et al., "CD4+ T-cells from mice immunized to syngeneic sarcomas recognize distinct, non-shared tumor antigens" 1994 Cancer Research 54:1055-8.
Estes et al., "CD40 ligand-dependent signaling of bovine B lymphocyte development and differentiation" Vet. Immunol. Immunopathol. 1998, 63:15-20.
Foy et al., "gp39-CD40 interactions are essential for germinal center formation and the development of B cell memory" J. Exp. Med. 1994, 180:157-63.
Gurunathan et al., "CD40 ligand/trimer DNA enhances both humoral and cellular immune responses and induces protective immunity to infectious and tumor challenge" 1998 J. Immunol. 161:4563-71.
Haas and Estes, "Activation of bovine B cells via surface immunoglobulin M cross-linking or CD40 ligation results in different B-cell phenotypes" 2000 Immunology 99:272.
Hirano et al., "Kinetics of expression and subset distribution of the TNF superfamily members CD40 ligand and Fas ligand on T lymphocytes in cattle" Vet. Immunol. Immonpathol. 1998, 61:251-63.
Kuby, "Overview of the Immune System," Immunology 1994, p. 1-20.
Ludmerer et al., "HPV11 Mutant Virus-like Particles Elicit Immune Responses That Neutralize Virus and Delineate a Novel Neutralizing Domain" Virology Jan. 20, 2000 266(2):237-45.
Mendoza et al., "Immunostimulatory effects of a plasmid expressing CD40 ligand (CD154) on gene immunization" 1997 J. Immunol. 159:5777.
Mertens et al., "Cloning of two members of the TNF-superfamily in cattle: CD40 ligand and tumor necrosis factor alpha" 1995 Immunogenetics 42:430-1.
Rolph et al. "CD40 signaling converts a minimally immunogenic antigen into a potent vaccine against the intracellular pathogen *Listeria monocytogenes*," J. Immunology 2001 v166 p. 5115.
Sin et al., "Modulation of cellular responses by plasmid CD40L: CD40L plasmid vectors enhance antigen-specific helper T cell type 1 CD4+ T cell-mediated protective immunity against herpes simplex virus type 2 in vivo" 2001 Hum. Gene Ther. 12:1091-102.
Tripp et al., "CD40 ligand (CD154) enhances the Th1 and antibody responses to respiratory syncytial virus in the BALB/c mouse" 2000 J. Immunol. 164:5913.
Van Kooten and Banchereau, "CO40-CO40 Ligand: A Multifunctional Receptor-Ligand Pair" 1996 Adv. Immunol. 61:1.
Van Kooten et al., "CD40-CD40 ligand" 2000 Leukocyte Biol. 67:2.

* cited by examiner

*Primary Examiner*—Michael Szperka
*Assistant Examiner*—Yunsoo Kim
(74) *Attorney, Agent, or Firm*—Casimir Jones SC

(57) ABSTRACT

The present invention relates to molecules that stabilize and/or enhance CD154 activity, compositions comprising these molecules, methods for using these molecules and compositions (e.g., pharmaceutical compositions) comprising them. Specifically, the molecules can be used for enhancing immune function (e.g., enhancing Th1 cytokine expression), stimulating immune responses, and/or treating certain disorders (e.g., cancer, infectious disease, and immune compromised states). The invention also relates to kits and compositions comprising the molecules.

15 Claims, 10 Drawing Sheets

** p<0.03 versus vehicle control
(Students one-tailed t test)

COMPOSITIONS AND METHODS FOR ALTERING IMMUNE FUNCTION

This application claims priority to U.S. Provisional Patent Application 60/686,224, filed Jun. 1, 2005, hereby incorporated by reference in its entirety.

This invention was funded, in part, under NIH Grants 5U19AI050853-02AI-00-016 and GM59957. The government may have certain rights in the invention.

FIELD OF THE INVENTION

The present invention relates to molecules that stabilize and/or enhance CD154 activity, compositions comprising these molecules, methods for using these molecules and compositions (e.g., pharmaceutical compositions) comprising them. Specifically, the molecules can be used for enhancing immune function (e.g., enhancing Th1 cytokine expression), stimulating immune responses, and/or treating certain disorders (e.g., cancer, infectious disease, and immune compromised states). The invention also relates to kits and compositions comprising the molecules.

BACKGROUND OF THE INVENTION

Cancer is the second leading cause of death, resulting in one out of every four deaths, in the United States. In 1997, the estimated total number of new diagnoses for lung, breast, prostate, colorectal and ovarian cancer was approximately two million. Due to the ever increasing aging population in the United States, it is reasonable to expect that rates of cancer incidence will continue to grow.

Cancer is currently treated using a variety of modalities including surgery, radiation therapy and chemotherapy. The choice of treatment modality will depend upon the type, location and dissemination of the cancer. One of the advantages of surgery and radiation therapy is the ability to control to some extent the impact of the therapy, and thus to limit the toxicity to normal tissues in the body. Chemotherapy is arguably the most appropriate treatment for disseminated cancers such as leukemia and lymphoma as well as metastases. Chemotherapy is generally administered systemically and thus toxicity to normal tissues is a major concern. Not all tumors, however, respond to chemotherapeutic agents and others, although initially responsive to chemotherapeutic agents, may develop resistance. As a result, the search for effective anti-cancer drugs has intensified in an effort to find even more effective agents with less non-specific toxicity.

Recently, much emphasis has been placed on the use of immunotherapy for the treatment and prevention of cancer and other disorders, including infectious disease. Immunotherapy provides the cell specificity that other treatment modalities lack. Methods for enhancing the efficacy of immune based therapies would be beneficial.

SUMMARY OF THE INVENTION

The invention provides compositions and methods of use in the prevention and treatment of disorders that would benefit from enhanced immunostimulation. The invention is based, in part, on the surprising observation that the small molecule compounds JFPB, JFPH, and functional equivalents (e.g., see Example 5, Table 2), stimulate the production of cytokines that can in turn stimulate immune cells. It has been found, according to the invention, that the small molecule compounds stimulate the production of IL-2 and IFN-γ, among others. Some of these cytokines activate macrophages and other antigen presenting cells, and thus are useful in enhancing immune responses that involve such cells including antibody dependent cell-mediated cytotoxicity, direct CD8 T cell mediated cytotoxicity and antigen presentation. Thus, in some embodiments, compositions comprising the small molecules are useful in altering (e.g., enhancing) humoral and cellular immune responses.

The ability of these small molecules to stimulate cytokine production endogenously is beneficial since exogenous administration of some of these factors, such as for example, IL-2, has been associated with toxicity. Production of IL-2 endogenously, and particularly in induction profiles that allow for induction in the spleen and lymph nodes with no detection in the serum indicates that the compositions comprising the small molecules can be used to induce cytokines in a controlled manner, and thereby overcome toxicity problems. Although not intending to be bound by any particular mechanism, it is further proposed that induction of these cytokines from cells in vivo also indicates that feedback loops normally operating in vivo may be operative and can control cytokine levels.

In some embodiments, the compositions of the present invention are administered with disease specific antibodies in order to enhance the efficacy of such antibodies. Again, although not intending to be bound by any particular mechanism, it is proposed that the production of cytokines following administration of compositions comprising the small molecules will lead to the stimulation of immune cells, thereby enhancing the response mediated by the exogenously administered antibody.

The present invention relates to methods and compositions for enhancing immune therapies for a number of indications, both in a therapeutic and a prophylactic sense, and for research and drug screening applications. Immune therapies comprising the compositions of the present invention include but are not limited to passive immune therapies such as immunoglobulin administration, and active immune therapies such as vaccination with antigens alone or antigens in the context of dendritic cells. The methods are intended to treat or prevent various indications that would benefit from an enhanced immune response.

In some embodiments, compositions comprising the small molecules of the present invention are administered with an antibody or antibody fragment, with an antigen and optionally with an adjuvant, or as stand alone compositions. In some embodiments, the immune response that is stimulated is a cell-mediated immune response involving T cells, NK cells, macrophages, and the like. In other embodiments, the immune response that is stimulated is a humoral response involving B cells and antibody production. In some embodiments, both types of responses co-exist. In still other embodiments, the immune response is an innate immune response, while in others it is an adaptive immune response.

Thus, in one aspect, the invention provides a method for stimulating an immune response in a subject comprising administering to a subject in need of immune stimulation a composition comprising JFPB and/or JFPH, or functional equivalents thereof, and an antibody or antibody fragment, in an amount effective to stimulate an immune response.

In some embodiments, the subject in need of immune stimulation is a subject having or at risk of developing cancer. The cancer may be selected from the group consisting of a carcinoma and a sarcoma, but it is not so limited. In some important embodiments, the cancer is neither a carcinoma nor a sarcoma. In a related embodiment, the cancer is a leukemia or a lymphoma.

In one embodiment, the cancer is selected from the group consisting of basal cell carcinoma, biliary tract cancer; bladder cancer; bone cancer; brain cancer; breast cancer; cervical cancer; choriocarcinoma; CNS cancer; colon and rectum cancer; connective tissue cancer; cancer of the digestive system; endometrial cancer; esophageal cancer; eye cancer; cancer of the head and neck; gastric cancer; intra-epithelial neoplasm; kidney cancer; larynx cancer; acute myeloid leukemia; acute lymphoid leukemia, chronic myeloid leukemia, chronic lymphoid leukemia, leukemia, liver cancer; small cell lung cancer; non-small cell lung cancer; lymphoma, Hodgkin's lymphoma; Non-Hodgkin's lymphoma; melanoma; myeloma; neuroblastoma; oral cavity cancer; ovarian cancer; pancreatic cancer; prostate cancer; retinoblastoma; rhabdomyosarcoma; rectal cancer; renal cancer; cancer of the respiratory system; sarcoma; skin cancer; stomach cancer; testicular cancer; thyroid cancer; uterine cancer; and cancer of the urinary system.

In another embodiment, the cancer is selected from the group consisting of bladder cancer, breast cancer, colon cancer, endometrial cancer, head and neck cancer, leukemia, lung cancer, lymphoma, melanoma, ovarian cancer, prostate cancer and rectal cancer.

In another embodiment, the cancer is a refractory cancer. Examples of refractory cancers include but are not limited to leukemias, melanomas, renal cell carcinomas, colon cancer, liver (hepatic) cancers, pancreatic cancer, Non-Hodgkin's lymphoma, and lung cancer. In still other embodiments, the cancer is an immunogenic cancer.

In still another embodiment, the cancer is a metastasis.

In some embodiments, the subject is one in need of immune stimulation is a subject having or at risk of developing an infectious disease. The infectious disease may be selected from the group consisting of, but not limited to, a bacterial infection, a mycobacterial infection, a viral infection, a fungal infection and a parasitic infection.

In some embodiments, the bacterial infection is selected from the group consisting of an *E. coli* infection, a *Staphylococcal* infection, a *Streptococcal* infection, a *Pseudomonas* infection, *Clostridium difficile* infection, *Legionella* infection, *Pneumococcus* infection, *Haemophilus* infection, *Klebsiella* infection, *Enterobacter* infection, *Citrobacter* infection, *Neisseria* infection, *Shigella* infection, *Salmonella* infection, *Listeria* infection, *Pasteurella* infection, *Streptobacillus* infection, *Spirillum* infection, *Treponema* infection, *Actinomyces* infection, *Borrelia* infection, *Corynebacterium* infection, *Nocardia* infection, *Gardnerella* infection, *Campylobacter* infection, *Spirochaeta* infection, *Proteus* infection, *Bacteriodes* infection, *H. pylori* infection, and *anthrax* infection.

The mycobacterial infection may be tuberculosis or leprosy respectively caused by the *M. tuberculosis* and *M. leprae* species, but is not so limited.

In some embodiments, the viral infection is selected from the group consisting of an HIV infection, a Herpes simplex virus 1 infection, a Herpes simplex virus 2 infection, cytomegalovirus infection, hepatitis A virus infection, hepatitis B virus infection, hepatitis C virus infection, human papilloma virus infection, Epstein Barr virus infection, rotavirus infection, adenovirus infection, JC viral infection, influenza A virus infection, respiratory syncytial virus infection, varicella-zoster virus infections, small pox infection, monkey pox infection and SARS infection.

In some embodiments, the viral infection is not an HIV infection.

In yet another embodiment, the fungal infection selected from the group consisting of candidiasis, ringworm, histoplasmosis, blastomycosis, paracoccidioidomycosis, cryptococcosis, aspergillosis, chromomycosis, mycetoma infections, pseudallescheriasis, and tinea versicolor infection.

In another embodiment, the parasite infection is selected from the group consisting of amebiasis, *Trypanosoma cruzi* infection, *Fascioliasis, Leishmaniasis, Plasmodium* infections, Onchocerciasis, Paragonimiasis, *Trypanosoma brucei* infection, *Pneumocystis* infection, *Trichomonas vaginalis* infection, *Taenia* infection, *Hymenolepsis* infection, *Echinococcus* infections, *Schistosomiasis*, neurocysticercosis, *Necator americanus* infection, and *Trichuris trichuria* infection.

In various aspects of the invention, the methods are intended to stimulate an immune response in a subject. In one embodiment, the immune response is antibody dependent cell-mediated cytoxicity. In another embodiment, the immune response is a cell-mediated immune response and/or a humoral (i.e., antibody-mediated) immune response. The immune response may be an innate immune response or an adaptive immune response, in other embodiments. In one embodiment, the immune response is an antigen specific immune response.

In some embodiment, the composition comprising JFPB, JFPH and/or functional equivalents is administered with or formulated with an antibody or antibody fragment. In one embodiment, the antibody or antibody fragment is an antibody.

The antibody or antibody fragment may be specific for a cell surface molecule. Cell surface molecules that may be targeted with the antibody or antibody fragment include but are not limited to HER 2, CD20, CD33, EGF receptor, HLA markers such as HLA-DR, CD52, CD1, CEA, CD22, GD2 ganglioside, FLK2/FLT3, VEGF, VEGFR, and the like.

The antibody or antibody fragment may be specific for a cancer antigen. Cancer antigens that may be targeted with the antibody or antibody fragment have been recited throughout the specification and include but are not limited to HER 2 (p185), CD20, CD33, GD3 ganglioside, GD2 ganglioside, carcinoembryonic antigen (CEA), CD22, milk mucin core protein, TAG-72, Lewis A antigen, ovarian associated antigens such as OV-TL3 and MOv18, high Mr melanoma antigens recognized by antibody 9.2.27, HMFG-2, SM-3, B72.3, PR5C5, PR4D2, and the like. Other cancer antigens are described in U.S. Pat. No. 5,776,427.

Cancer antigens can be classified in a variety of ways. Cancer antigens include antigens encoded by genes that have undergone chromosomal alteration. Many of these antigens are found in lymphoma and leukemia. Even within this classification, antigens can be characterized as those that involve activation of quiescent genes. These include BCL-1 and IgH (Mantel cell lymphoma), BCL-2 and IgH (Follicular lymphoma), BCL-6 (Diffuse large B-cell lymphoma), TAL-1 and TCRδ or SIL (T-cell acute lymphoblastic leukemia), c-MYC and IgH or IgL (Burkitt lymphoma), MUN/IRF4 and IgH (Myeloma), PAX-5 (BSAP) (Immunocytoma).

Other cancer antigens that involve chromosomal alteration and thereby create a novel fusion gene and/or protein include RARoa, PML, PLZF, NPMor NuM4 (Acute promyelocytic leukemia), BCR and ABL (Chronic myeloid/acute lymphoblastic leukemia), MLL (HRX) (Acute leukemia), E2A and PBXor HLF (B-cell acute lymphoblastic leukemia), NPM, ALK (Anaplastic large cell leukemia), and NPM, MLF-1 (Myelodysplastic syndrome/acute myeloid leukemia).

Other cancer antigens are specific to a tissue or cell lineage. These include cell surface proteins such as CD20, CD22 (Non-Hodgkin's lymphoma, B-cell lymphoma, Chronic lymphocytic leukemia (CLL)), CD52 (B-cell CLL), CD33 (Acute myelogenous leukemia (AML)), CD 10 (gp100)

(Common (pre-B) acute lymphocytic leukemia and malignant melanoma), CD3/T-cell receptor (TCR) (T-cell lymphoma and leukemia), CD79/B-cell receptor (BCR) (B-cell lymphoma and leukemia), CD26 (Epithelial and lymphoid malignancies), Human leukocyte antigen (HLA)-DR, HLA-DP, and HLA-DQ (Lymphoid malignancies), RCAS1 (Gynecological carcinomas, bilary adenocarcinomas and ductal adenocarcinomas of the pancreas), and Prostate specific membrane antigen (Prostate cancer).

Tissue- or lineage-specific cancer antigens also include epidermal growth factor receptors (high expression) such as EGFR (HER1 or erbB1) and EGFRvIII (Brain, lung, breast, prostate and stomach cancer), erbB2 (HER2 or HER2/neu) (Breast cancer and gastric cancer), erbB3 (HER3) (Adenocarcinoma), and erbB4 (HER4) (Breast cancer).

Tissue- or lineage-specific cancer antigens also include cell-associated proteins such as Tyrosinase, Melan-A/MART-1, tyrosinase related protein (TRP)-1/gp75 (Malignant melanoma), Polymorphic epithelial mucin (PEM) (Breast tumors), and Human epithelial mucin (MUC1) (Breast, ovarian, colon and lung cancers).

Tissue- or lineage-specific cancer antigens also include secreted proteins such as Monoclonal immunoglobulin (Multiple myeloma and plasmacytoma), Immunoglobulin light chains (Multiple Myeloma), alpha.-fetoprotein (Liver carcinoma), Kallikreins 6 and 10 (Ovarian cancer), Gastrin-releasing peptide/bombesin (Lung carcinoma), and Prostate specific antigen (Prostate cancer).

Still other cancer antigens are cancer testis (CT) antigens that are expressed in some normal tissues such as testis and in some cases placenta. Their expression is common in tumors of diverse lineages and as a group the antigens form targets for immunotherapy. Examples of tumor expression of CT antigens include MAGE-A1, -A3, -A6, -A12, BAGE, GAGE, HAGE, LAGE-1, NY-ESO-1, RAGE, SSX-1, -2, -3, -4, -5, -6, -7, -8, -9, HOM-TES-14/SCP-1, HOM-TES-85 and PRAME. Still other examples of CT antigens and the cancers in which they are expressed include SSX-2, and -4 (Neuroblastoma), SSX-2 (HOM-MEL-40), MAGE, GAGE, BAGE and PRAME (Malignant melanoma), HOM-TES-14/SCP-1 (Meningioma), SSX-4 (Oligodendrioglioma), HOM-TES-14/SCP-1, MAGE-3 and SSX-4 (Astrocytoma), SSX member (Head and neck cancer, ovarian cancer, lymphoid tumors, colorectal cancer and breast cancer), RAGE-1, -2, -4, GAGE-1-2, -3, -4, -5, -6, -7 and -8 (Head and neck squamous cell carcinoma (HNSCC)), HOM-TES14/SCP-1, PRAME, SSX-1 and CT-7 (Non-Hodgkin's lymphoma), and PRAME (Acute lymphoblastic leukemia (ALL), acute myelogenous leukemia (AML) and chronic lymphocytic leukemia (CLL)).

Other cancer antigens are not specific to a particular tissue or cell lineage. These include members of the carcinoembryonic antigen (CEA) family: CD66a, CD66b, CD66c, CD66d and CD66e. These antigens can be expressed in many different malignant tumors and can be targeted by immunotherapy.

Still other cancer antigens are viral proteins and these include Human papilloma virus protein (cervical cancer), and EBV-encoded nuclear antigen (EBNA)-1 (lymphomas of the neck and oral cancer).

Still other cancer antigens are mutated or aberrantly expressed molecules such as but not limited to CDK4 and beta-catenin (melanoma).

In some embodiments, compositions comprising small molecules of the present invention are administered in combination with antibodies or antibody fragments specific for any of the foregoing cancer antigens.

The antibody or antibody fragment may be specific for a stromal cell molecule. Stromal cell molecules that may be targeted with the antibody or antibody fragment include but are not limited to FAP and CD26.

The antibody or antibody fragment may be specific for an extracellular matrix molecule. Extracellular matrix molecules that may be targeted with the antibody or antibody fragment include but are not limited to collagen, glycosaminoglycans (GAGs), proteoglycans, elastin, fibronectin and laminin.

The antibody or antibody fragment may be specific for a tumor vasculature molecule. Tumor vasculature molecules include but are not limited to endoglin, ELAM-1, VCAM-1, ICAM-1, ligand reactive with LAM-1, MHC class II antigens, aminophospholipids such as phosphatidylserine and phosphatidylethanolamine, VEGFR1 (Flt-1) and VEGFR2 (KDR/Flk-1).

Antibodies to endoglin include TEC-4 and TEC-11. Antibodies that inhibit VEGF include 2C3 (ATCC PTA 1595). Other antibodies that are specific for tumor vasculature include antibodies that react to a complex of a growth factor and its receptor such as a complex of FGF and the FGFR or a complex of TGFβ and the TGFβR. Antibodies of this latter class include GV39 and GV97.

In a related embodiment, the antibody or antibody fragment is selected from the group consisting of trastuzumab, alemtuzumab (B cell chronic lymphocytic leukemia), gemtuzumab ozogamicin (CD33+ acute myeloid leukemia), hP67.6 (CD33+ acute myeloid leukemia), infliximab (inflammatory bowel disease and rheumatoid arthritis), etanercept (rheumatoid arthritis), rituximab, tositumomab, MDX-210, oregovomab, anti-EGF receptor mAb, MDX-447, anti-tissue factor protein (TF), (Sunol); ior-c5, c5, edrecolomab, ibritumomab tiuxetan, anti-idiotypic mAb mimic of ganglioside GD3 epitope, anti-HLA-Dr10 mAb, anti-CD33 humanized mAb, anti-CD52 humAb, anti-CD1 mAb (ior t6), MDX-22, celogovab, anti-17-1A mAb, bevacizumab, daclizumab, anti-TAG-72 (MDX-220), anti-idiotypic mAb mimic of high molecular weight proteoglycan (I-Mel-1), anti-idiotypic mAb mimic of high molecular weight proteoglycan (I-Mel-2), anti-CEA Ab, hmAbH11, anti-DNA or DNA-associated proteins (histones) mAb, Gliomab-H mAb, GNI-250 mAb, anti-CD22, CMA 676), anti-idiotypic human mAb to GD2 ganglioside, ior egf/r3, anti-ior c2 glycoprotein mAb, ior c5, anti-FLK-2/FLT-3 mAb, anti-GD-2 bispecific mAb, anti-nuclear autoantibodies, anti-HLA-DR Ab, anti-CEA mAb, palivizumab, bevacizumab, alemtuzumab, BLyS-mAb, anti-VEGF2, anti-Trail receptor; B3 mAb, mAb BR96, breast cancer; and Abx-Cb1 mAb.

In some embodiments, the antibody or antibody fragment is an anti-HER2 antibody, and preferably it is trastuzumab. In another embodiment, the antibody or antibody fragment is an anti-CD20 antibody, and preferably it is rituximab.

The antibody or antibody fragment may be conjugated (covalently or otherwise) to a toxin derived from plant, fungus, or bacteria. The toxin may be selected from the group consisting of A chain toxin, deglycosylated A chain toxin, ribosome inactivating protein, α-sarcin, aspergillin, restrictocin, ribonuclease, diptheria toxin and *Pseudomonas* exotoxin, but is not so limited.

The antibody or antibody fragment may also conjugated to a chemotherapeutic agent, a radioisotope or a cytotoxin. The chemotherapeutic agent may be selected from the group comprising, but not limited to, an anti-metabolite, an anthracycline, a vinca alkaloid, an antibiotic, an alkylating agent, and an epipodophyllotoxin.

In some embodiments, the antibody or antibody fragment is administered in a sub-therapeutic dose.

In some embodiments, the composition comprising JFPB, JFPH, and/or functional equivalents is administered on a routine schedule.

In some embodiments, the composition comprising JFPB, JFPH, and/or functional equivalents is administered in a route of administration different from that of the antibody or antibody fragment.

In still other embodiments, the subject is otherwise free of symptoms calling for immune (e.g., humoral or cell mediated hematopoietic) stimulation. In some embodiments, the subject may be non-immunocompromised. In some embodiments, the subject is genetically immunocompromised, and may be so as a result of a genetic mutation such as in agammaglobulinemia, X-linked hyper-IgM syndrome, or SCID. In another embodiment, the subject may have an immune deficiency selected from the group consisting of Bruton's agammaglobulinemia, congenital hypogammaglobulinemia, common variable immunodeficiency, and selective immunoglobulin A deficiency. In another embodiment, the subject is elderly (e.g., at least 50 years old). In still another embodiment, the subject is non-immunocompromised as the subject has not undergone any immunosuppressive therapies such as chemotherapy or radiation.

In some embodiments, the composition comprising JFPB, JFPH, and/or functional equivalents is administered orally and the antibody or antibody fragment is administered by injection. In another embodiment, the composition comprising JFPB, JFPH, and/or functional equivalents is administered prior to the antibody or antibody fragment. In still another embodiment, the composition comprising JFPB, JFPH, and/or functional equivalents is administered in an amount that increases lymphoid tissue (e.g., spleen) levels of IL-2, IFN-γ, IL-1, G-CSF or IL-8 (KC in mice). In some embodiment, the composition comprising JFPB, JFPH, and/or functional equivalents is administered in an amount that does not increase serum IFN-γ levels.

In some embodiments, the composition comprising JFPB, JFPH, and/or functional equivalents is administered 30 minutes to 8 hours prior to the antibody or antibody fragment. In another embodiment, the composition comprising JFPB, JFPH, and/or functional equivalents is administered 1 to 7 days prior to the antibody or antibody fragment. In yet another embodiment, the composition comprising JFPB, JFPH, and/or functional equivalents is administered substantially simultaneously with the antibody or antibody fragment. As used herein, the term "substantially simultaneously" means that the small molecule compounds are administered within minutes of each other (e.g., within 10 minutes of each other) and intends to embrace joint administration as well as consecutive administration, but if the administration is consecutive it is separated in time for only a short period (e.g., the time it would take a medical practitioner to administer two small molecule compounds separately). As used herein, concurrent administration and substantially simultaneous administration are used interchangeably.

In some embodiments, the composition comprising JFPB, JFPH, and/or functional equivalents is administered after the antibody or antibody fragment.

The antibody or antibody fragment may be administered on a first day of multi-day cycle, with the composition comprising JFPB, JFPH, and/or functional equivalents administered on the remaining days of the cycle. The cycle may be a 2, 3, 4, 5, 6, 7, or more day cycle. The composition comprising JFPB, JFPH, and/or functional equivalents may be administered once, twice, or more times per day. In some embodiments, the antibody or antibody fragment is administered on the first day of a seven day cycle, followed by a twice daily administration of the composition comprising JFPB, JFPH, and/or functional equivalents on each of the remaining days of the seven day cycle.

The multi-day cycle may be repeated twice, thrice, four times, or more. It may also be repeated for various lengths of time, including but not limited to a week, a month, two months, or more.

The compositions of the present invention may be provided in a housing such as a container, a box, or a bag. The housing may also contain instructions for use of the composition either thereon or therein. The instructions for use indicate how the contents of the housing are to be used, including timing and dose of administrations. In these latter embodiments, the compositions may be contained in a kit.

In another aspect, the invention provides a method for stimulating an immune response in a subject comprising administering to a subject in need of immune stimulation a composition comprising JFPB, JFPH, and/or functional equivalents, and an antigen, in an amount effective to stimulate an antigen-specific immune response, wherein the composition comprising JFPB, JFPH, and/or functional equivalents is administered at a concentration of greater than $10^{-8}$M.

In some embodiments, the composition comprising JFPB, JFPH, and/or functional equivalents is administered on a routine schedule. In another embodiment, the composition comprising JFPB, JFPH, and/or functional equivalents is administered in a route of administration different from that of the antigen.

In another embodiment, the method further comprises administering an adjuvant to the subject. In some embodiments, the adjuvant is selected from the group consisting of alum, cholera toxin, CpG immunostimulatory nucleic acids, MPL, MPD, and QS-2 1.

In some embodiments, the antigen is a cancer antigen. The cancer antigen may be selected from the group consisting of MART-1/Melan-A, gp100, adenosine deaminase-binding protein (ADAbp), FAP, cyclophilin b, colorectal associated antigen (CRC)-C017-1A/GA733, carcinoembryonic antigen (CEA), CAP-1, CAP-2, etv6, AML1, prostate specific antigen (PSA), PSA-1, PSA-2, PSA-3, prostate-specific membrane antigen (PSMA), T-cell receptor/CD3-zeta chain, and CD20. The cancer antigen may also be selected from the group consisting of MAGE-A1, MAGE-A2, MAGE-A3, MAGE-A4, MAGE-A5, MAGE-A6, MAGE-A7, MAGE-A8, MAGE-A9, MAGE-A10, MAGE-A11, MAGE-A12, MAGE-Xp2 (MAGE-B2), MAGE-Xp3 (MAGE-B3), MAGE-Xp4 (MAGE-B4), MAGE-C1, MAGE-C2, MAGE-C3, MAGE-C4, MAGE-C5). In still another embodiment, the cancer antigen is selected from the group consisting of GAGE-1, GAGE-2, GAGE-3, GAGE-4, GAGE-5, GAGE-6, GAGE-7, GAGE-8, GAGE-9. And in yet a further embodiment, the cancer antigen is selected from the group consisting of BAGE, RAGE, LAGE-1, NAG, GnT-V, MUM-1, CDK4, tyrosinase, p53, MUC family, HER2/neu, p21 ras, RCAS 1, .alpha.-fetoprotein, E-cadherin, .alpha.-catenin, .beta.-catenin, .gamma.-catenin, p120ctn, gp100.sup.Pmel117, PRAME, NY-ESO-1, cdc27, adenomatous polyposis coli protein (APC), fodrin, Connexin 37, Ig-idiotype, p15, gp75, GM2 ganglioside, GD2 ganglioside, human papilloma virus proteins, Smad family of tumor antigens, lmp-1, P1A, EBV-encoded nuclear antigen (EBNA)-1, brain glycogen phosphorylase, SSX-1, SSX-2 (HOM-MEL-40), SSX-1, SSX-4, SSX-5, SCP-1 and CT-7, and c-erbB-2.

In some embodiments of the foregoing aspects of the invention, the methods may further comprise treating the subject with a therapy selected from the group consisting of surgery, radiation and chemotherapy.

In some embodiments, the composition comprising JFPB, JFPH, and/or functional equivalents is administered prior to treating the subject with a therapy selected from the group consisting of surgery, radiation and chemotherapy. In some embodiments, the composition comprising JFPB, JFPH, and/or functional equivalents is administered after treating the subject with a therapy selected from the group consisting of surgery, radiation and chemotherapy. In yet another embodiment, the composition comprising JFPB, JFPH, and/or functional equivalents is administered before and after treating the subject with a therapy selected from the group consisting of surgery, radiation and chemotherapy.

In some embodiments, the composition comprising JFPB, JFPH, and/or functional equivalents is administered with an antigen or portion thereof. In some embodiments, the antigen is a microbial antigen. As used herein, a microbial antigen is an antigen derived from an infectious pathogen, and may include the entire pathogen. The antigen may be peptide, lipid, or carbohydrate in nature, but it is not so limited.

In some embodiments, the microbial antigen is selected from the group consisting of a bacterial antigen, a mycobacterial antigen, a viral antigen, a fungal antigen, and a parasitic antigen.

In some embodiments, the bacterial antigen is derived from a bacterial species selected from the group consisting of *E. coli, Staphylococcal, Streptococcal, Pseudomonas, Clostridium difficile, Legionella, Pneumococcus, Haemophilus, Klebsiella, Enterobacter, Citrobacter, Neisseria, Shigella, Salmonella, Listeria, Pasteurella, Streptobacillus, Spirillum, Treponema, Actinomyces, Borrelia, Corynebacterium, Nocardia, Gardnerella, Campylobacter, Spirochaeta, Proteus, Bacteriodes, H. pylori*, and *anthrax*.

The mycobacterial antigen may be derived from a mycobacterial species such as *M. tuberculosis* and *M. leprae*, but is not so limited.

In another embodiment, the viral antigen is derived from a viral species selected from the group consisting of HIV, Herpes simplex virus 1, Herpes simplex virus 2, cytomegalovirus, hepatitis A virus, hepatitis B virus, hepatitis C virus, human papilloma virus, Epstein Barr virus, rotavirus, adenovirus, influenza A virus, respiratory syncytial virus, varicella-zoster virus, small pox, monkey pox and SARS.

In yet another embodiment, the fungal antigen is derived from a fungal species that causes an infection selected from the group consisting of candidiasis, ringworm, histoplasmosis, blastomycosis, paracoccidioidomycosis, crytococcosis, aspergillosis, chromomycosis, mycetoma infections, pseudallescheriasis, and tinea versicolor infection.

In some embodiments, the parasitic antigen is derived from a parasite species selected from the group consisting of amebiasis, *Trypanosoma cruzi, Fascioliasis, Leishmaniasis, Plasmodium, Onchocerciasis, Paragonimiasis, Trypanosoma brucei, Pneumocystis, Trichomonas vaginalis, Taenia, Hymenolepis, Echinococcus, Schistosomiasis*, neurocysticercosis, *Necator americanus*, and *Trichuris trichuria*.

The invention intends to embrace various antigens from the infectious pathogens recited herein.

In some embodiments, the composition comprising JFPB, JFPH, and/or functional equivalents is administered with a pharmaceutically acceptable carrier.

In some embodiments, the effective amount is an amount to stimulate antibody dependent cell-mediated cytotoxicity. In another embodiment, the effective amount is an amount to treat or prevent cancer.

For example, in some embodiments, a composition comprising JFPB, JFPH and/or functional equivalents is administered to a subject in order to prevent cancer growth. In some embodiments, a composition comprising JFPB, JFPH and/or functional equivalents is administered to a subject in order to prevent cancer metastasis. In still another embodiment, the effective amount is an amount to treat or prevent an infectious disease.

In another aspect, the invention provides a composition comprising an effective amount of a composition comprising JFPB, JFPH, and/or functional equivalents and a cancer antigen. In some embodiments, the effective amount is an amount to treat or prevent cancer, while maintaining a desired immune response.

In this and other aspects of the invention, the cancer antigen may be a peptide antigen, or a lipid antigen, but it is not so limited. The cancer antigen can be selected from the groups recited above. In some embodiments, the composition comprising JFPB, JFPH, and/or functional equivalents is formulated for administration at a dose of greater than $10^{-8}$M.

In yet another aspect, the invention provides a method of preventing an infectious disease in a subject at risk of developing an infectious disease comprising identifying a subject at risk of developing an infectious disease, and administering a composition comprising JFPB, JFPH, and/or functional equivalents to the subject in an amount effective to induce IL-2 and/or IFN-$\gamma$.

In some embodiments, the method further comprises administering to the subject a microbial antigen, selected from the groups recited above. In one embodiment, the infectious disease is selected from the group consisting of a bacterial infection, a viral infection, a fungal infection and a parasitic infection, and these can be selected from the groups listed above.

In some embodiments, the subject is HIV negative. In some embodiments, the viral infection is selected from the group consisting of a Herpes simplex virus 1 infection, a Herpes simplex virus 2 infection, cytomegalovirus infection, hepatitis A virus infection, hepatitis B virus infection, hepatitis C virus infection, human papilloma virus infection, Epstein Barr virus infection, rotavirus infection, adenovirus infection, influenza A virus infection, respiratory syncytial virus infection, varicella-zoster virus infections, small pox infection, monkey pox infection and SARS infection.

In yet another aspect, the invention provides a composition comprising an effective amount of a composition comprising JFPB, JFPH, and/or functional equivalents and a microbial antigen, wherein an agent comprising JFPB, JFPH, and/or functional equivalent is formulated for administration at a dose of greater than $10^{-8}$M. In some embodiments, the effective amount is an amount to treat or prevent an infectious disease. The microbial antigen can be selected from the groups recited above.

In yet another aspect, the invention provides a method for stimulating an immune response in a subject having or at risk of having cancer comprising administering to a subject in need of immune stimulation an agent comprising JFPB, JFPH, and/or functional equivalents, and an antigen, in an amount effective to stimulate an antigen-specific immune response.

In some embodiments, the subject is HIV negative. In another embodiment, the subject is a subject having cancer. In yet another embodiment, the cancer is selected from the group consisting of a lymphoma or leukemia. In still other embodiments, the cancer may be selected from the groups recited above. In one embodiment, the cancer is a metastasis. In yet another embodiment, the subject has or is at risk of developing an infectious disease, and these infectious diseases can be selected from the groups recited above. In one embodiment, the subject is further administered an antigen such as a cancer antigen or a microbial antigen, and either can be selected from the groups recited above.

In some embodiments, the subject receiving compositions of the present invention will have a surgery. In another embodiment, the subject has a skin abrasion from a trauma. In yet another embodiment, the subject is traveling to a region in which a microbial infection is common. In one embodiment, the subject is elderly.

In some embodiments, a method is provided for treating a subject having or at risk of developing an interferon (IFN)-responsive condition. The method comprises administering to a subject in need of such treatment an agent comprising JFPB, JFPH, and/or functional equivalents. In some embodiments, the agent comprising JFPB, JFPH, and/or functional equivalents is administered in an amount effective to induce a therapeutically or prophylactically effective amount of IL-2 and/or IFN-γ in the subject.

In some embodiments, the method may further comprise identification of a subject having or at risk of developing an IFN-responsive condition. The IFN may be IFN-α, IFN-α2b, IFN-β or IFN-γ, but is not so limited. In some embodiments, the condition is an IFN-γ-responsive condition, and may be selected from the group consisting of viral infections and associated diseases, and cancer. In some embodiments, the subject is HIV positive. In one embodiment, the IFN-responsive condition is a chronic infection selected from the group consisting of a chronic hepatitis B infection, chronic hepatitis C infection, chronic Epstein Barr Virus infection, and tuberculosis. Other disorders include hepatocellular carcinoma, Kaposi's Sarcoma (AIDS-related), thick primary melanomas, and regional lymph node metastases. In one embodiment, the disorder is refractive (i.e., resistant) to prior therapy (e.g., drug treatment) Thus, in some embodiments, the disorder is drug resistant. In another embodiment, the disorder is multiple sclerosis. IFN-responsive conditions are not intended to be limited to those described.

In some embodiments, the compositions of the present invention are administered with one or more agents selected from the group consisting of IFN-α, pegylated IFN, IFN-α2b, acyclovir, lobucavir, ganciclovir, L-deoxythymidine, clevudine, a therapeutic vaccine, phosphonoformate (PFA), ribavirin (RBV), thymosin alpha-1, 2 3-dideoxy-3-fluoroguanosine (FLG), famciclovir, lamivudine, adefovir dipivoxil, entecavir, emtricitabine, and hepatitis B-specific immunoglobulin.

In a further aspect, the invention provides a method for treating a subject having or at risk of developing cancer comprising administering to a subject in need of such treatment an enzyme inhibitor selected from the group consisting of a tyrosine kinase inhibitor, a CDK inhibitor, a MAP kinase inhibitor, and an EGFR inhibitor, and an agent comprising JFPB, JFPH, and/or functional equivalents in an amount effective to inhibit the cancer. In some embodiments, the tyrosine kinase inhibitor is selected from the group consisting of Genistein (4',5,7-trihydroxyisoflavone), Tyrphostin 25 (3,4,5-trihydroxyphenyl), methylene]-propanedinitrile, Herbimycin A, Daidzein (4',7-dihydroxyisoflavone), AG-126, trans-]-(3'-carboxy-4'-hydro-xyphenyl)-2-(2",5"-dihydroxyphenyl)ethane, and HDBA (2-Hydroxy5-(2,5-Dihydroxybenzylamino)-2-hydroxybenzoic acid. In another embodiment, the CDK inhibitor is selected from the group consisting of p21, p27, p57, p15, p16, p18, and p19. In another embodiment the MAP kinase inhibitor is selected from the group consisting of KY 12420 (C.sub.23H.sub.24O.sub.8), CNI-1493, PD98059, 4-(4-Fluorophenyl)-2-(4-met- hylsulfinyl phenyl)-5-(4-pyridyl) 1H-imidazole. In still a further embodiment, the EGFR inhibitor is selected from the group consisting of TARCEVA (OSI-774), IRESSA (ZD1839), WHI-P97 (quinazoline derivative), LFM-A12 (leflunoinide metabolite analog), AG1458. In various embodiments, the amount effective is a synergistic amount.

In yet one more aspect of the invention, a method is provided for treating a subject having or at risk of developing cardiovascular disease comprising administering to a subject in need of such treatment an agent comprising JFPB, JFPH, and/or functional equivalents in an amount effective to induce an effective amount of IL-2 and/or IFN-γ. The method may further comprise identifying a subject in need of such treatment.

In another aspect, the invention provides a method for preventing drug resistance in a subject. The method involves administering to a subject receiving an anti-microbial agent, an agent comprising JFPB, JFPH, and/or functional equivalents in an amount effective to reduce the risk of resistance to the anti-microbial agent. In one embodiment, the subject is one having or is at risk of developing an infectious disease. As used herein, the terms "infectious disease" and "microbial infection" are used interchangeably and intended to convey an infection by any microbe including but not limited to a bacterium, a mycobacterium, a virus, a fungus, a parasite, and the like. Thus, in some embodiments, the infectious disease is selected from the group consisting of a bacterial infection, a viral infection, a fungal infection and a parasitic infection. In one embodiment, the bacterial infection is a *Pseudomonas* infection. Other drug resistant microbes and the drugs to which they are resistant include *Staphylococcus aureus* (penicillin), *Streptococcus pneumoniae* (penicillin), *gonorrhea* (penicillin), and *Enterococcus faecium*(penicillin). In some embodiments, the anti-microbial agent is selected from the group consisting of an anti-bacterial agent, an anti-viral agent, an anti-fungal agent, and an anti-parasitic agent.

In still another aspect, the invention provides a method for shortening a vaccination course. As used herein, "shortening a vaccination course" refers to reducing either the number of vaccine administrations (e.g., by injection) or the time between vaccine administrations. This is accomplished by stimulating a more robust immune response in the subject. The method may involve, in one embodiment, administering to a subject in need of immunization an agent comprising JFPB, JFPH, and/or functional equivalents in an amount effective to induce an antigen-specific immune response to a vaccine administered in a vaccination course, wherein the vaccination course is shortened by at least one immunization. In other embodiments, the vaccination course is shortened by one immunization, two immunizations, three immunizations, or more. The method may involve, in another embodiment, administering to a subject in need of immunization an agent comprising JFPB, JFPH, and/or functional equivalents in an amount effective to induce an antigen-specific immune response to a vaccine administered in a vaccination course, wherein the vaccination course is shortened by at least one day. In other embodiments, the vaccination course is shortened by one day, two days, three days, four days, five days, six days, one week, two weeks, three weeks, four weeks, one month, two months or more. In one embodiment, the agent comprising JFPB, JFPH, and/or functional equivalents is administered substantially simultaneously with the vaccine. Immunizations that can be modified in this way include but are not limited to newborn immunizations for HBV; immunizations at for example two months of age for Polio, DTaP, Hib, HBV, Pneumococcus; immunizations at for example four months of age for Polio, DTAP, Hib, Pneumococcus; immunizations at for example six months of age for Polio, DTaP, Hib, HBV, Pneumococcus; immunizations at for example 12-15 months of age for Hib, Pneumococcus, MMR, Varicella; immunizations at for example 15-18 months of age for DtaP; immunizations at for example 4-6 years of age for Polio, DPT, MMR; immunizations at for example 11-12 years of age for MMR; immunizations at for example 14-16 years of age for tetanus-diphtheria (i.e., Td) (with a repeat as a booster every 10 years). As an example, a recommended vaccination course for tetanus/diphtheria includes a primary immunization series given in adults if not received as a child, followed by routine booster doses of tetanus-diphtheria (Td) every 10 years. The method of the invention will allow for a shortened series of vaccinations at the first time point, and may in some instances obviate the need for booster shots later on. As another example, hepatitis vaccination commonly requires three administrations spaced at least two weeks, and sometimes one month, apart in order to develop full immunity. Using the methods of the invention, it is possible to either reduce the number of injections from three to two or one, or to reduce the time in between injections from weeks or months to days or weeks. Vaccination courses that can be shortened by the method of the invention include but are not limited to: HBV: Hepatitis B vaccine (3 total doses currently recommended); Polio: Inactivated polio vaccine (4 total doses currently recommended); DTaP: Diphtheria/tetanus/acellular Pertussis (3-in-1 vaccine; 5 total doses currently recommended); Hib: *Haemophilus influenzae* type b conjugate vaccine (4 total doses currently recommended); Pneumococcus (Prevnar): Protects against certain forms of *Strep. Pneumoniae* (3 total doses recommended); MMR: measles/mumps/rubella (3-in-1 vaccine; 2 total doses recommended); Td: Adult tetanus/diphtheria (2-in-i vaccine; for use in people over age 7). In another embodiment, an agent comprising JFPB, JFPH, and/or functional equivalent can be used together with oral polio vaccine.

The invention provides in yet another aspect a method for stimulating an immune response in a subject having cancer comprising administering to a subject in need of such treatment an agent comprising JFPB, JFPH, and/or functional equivalents in an amount effective to stimulate an antigen-specific immune response, prior to and following a therapy selected from the group consisting of radiation, surgery and chemotherapy, wherein the method further comprises administering an adjuvant to the subject. In some embodiments, the adjuvant is selected from the group consisting of alum, cholera toxin, CpG immunostimulatory nucleic acids, MPL, MPD, and QS-21.

In still another aspect, a method is provided for stimulating an immune response in a subject at risk of developing cancer comprising administering to a subject in need of such treatment an agent comprising JFPB, JFPH, and/or functional equivalents in an amount effective to stimulate an antigen-specific immune response wherein the subject at risk of developing cancer has a familial predisposition to developing cancer. In some embodiments, the familial predisposition is familial colon polyposis. In some embodiments, the subject has precancerous polyps. In some embodiments, the subject has precancerous HPV lesions. In some embodiments the familial predisposition can include BRCA1- and BRCA2-associated breast cancer, Wilms tumor, colorectal cancer, Li-Fraumeni Syndrome, ovarian cancer, and prostate cancer. In another embodiment, the subject is at risk of developing a cancer that is a metastasis.

DETAILED DESCRIPTION OF THE INVENTION

Figure 1:
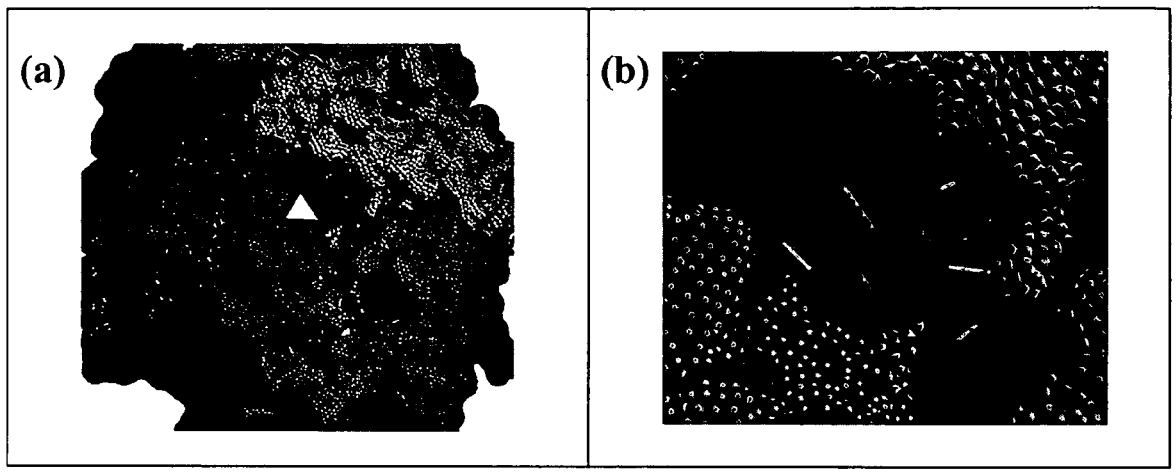
FIG. 1 depicts a visualization of the homotrimer binding site and demonstration of a chemical docked into this site.

CD154 and the CD40R belong to the TNF superfamily (van Kooten et al., Leukocyte Biol. 67:2). CD154 (CD40L, TNF-related activation protein, or gp39), a 39-kDa glycoprotein, is expressed as a type II integral membrane protein on the surface of activated T cells, basophils, and mast cells. Its receptor, CD40, is a 45- to 50-kDa surface protein that is expressed on B cells, DCs, macrophages, and Langerhans cells, and also on nonhemopoietic cells including endothelial cells, fibroblasts, and epithelial cells. CD40-CD154 interactions between DCs and T cells provide signals for activation and maturation of DCs (Banchereau and Steinman. 1998. Nature 392:245). CD154 ligation of CD40 on B cells influences various stages in B cell development (Banchereau et al., 1994. Ann. N Y Acad. Sci. 725:22; Van Kooten and Banchereau. 1996. Adv. Immunol. 61:1; Foy et al., 1994. J. Exp. Med. 180:157), including secretion of cytokines (Burdin et al., 1996. J. Immunol. 156:4107) and Ig isotype switching. Bovine CD154 has been cloned and sequenced (Mertens et al., 1995. Immunogenetics 42:430), and the kinetics and expression of CD154 on bovine T cells (Hirano et al., 1998. Vet. Immunol. Immunopathol. 61:251) and its role in bovine B cell development and differentiation (Estes et al., 1998. Vet. Immunol. Immunopathol. 63:15; Haas and Estes. 2000. Immunology 99:272) have been investigated. Coadministration of a plasmid encoding CD154 and a plasmid encoding the Ag of interest enhanced humoral and cellular immune responses in mice (Mendoza et al., 1997. J. Immunol. 159: 5777; Sin et al., 2001. Hum. Gene Ther. 12:1091; Gurunathan et al., 1998. J. Immunol. 161:4563; Tripp et al., 2000. J. Immunol. 164:5913).

Experiments conducted during the development of the present invention set out to identify small molecules that were capable of acting as inhibitors/stabilizers of CD154 trimerization with the goal of developing new therapies for either inhibiting immune cell function in autoimmune disease, or enhancing natural or vaccine facilitated immune responses (See, e.g., Examples 1 and 2).

As such, small molecules of the present invention were used to modulate CD154 trimer stability on the cell surface of activated T cells as well as other cell types. Among other functions, the CD154 antigen is central to the induction of Th1 responses and immune effector function in the target site.

Antigen presenting cells present antigen to T cells through Major Histocompatibility Complex I and II. For effective T cell activation to occur, co-stimulation must be present through expression of CD80 and/or CD86 on the antigen presenting cells. In turn this results in the expression of CD154 on activated T cells. CD154 expression is extremely transient and has been implicated in the induction of strong type 1 immune responses. CD154 on the activated T cell binds CD40 on the antigen presenting cell, resulting in co-stimulatory signals to that antigen presenting cell and induction of proteins such as IL-12, chemokines and increased levels of CD80/CD86 expression. This has been suggested to become a positive feedback loop between antigen presenting cells and T cells.

CD154 expression is important for induction of an effective immune response to antigen. The strict control of expression of CD154 on the T cell suggests that prolonged ligation of CD40, by CD154 trimers, may result in exacerbated immune responses, under normal circumstances. Thus, the development of the present invention was initiated to modulate the expression of CD154 trimers on the cell surface of activated T cells, in order to either inhibit or enhance the developing immune response and effector function.

Thus, the invention is based in part on the discovery that the small molecules JFPB, JFPH, and/or functional equivalents stimulate a variety of cytokines and chemokines which can stimulate the immune system. Thus, in some embodiments, a composition comprising JFPB, JFPH, and/or functional equivalents is administered to enhance immune (e.g., humoral or cell mediated) responses. The resultant immune stimulation can also be exploited to enhance the efficacy of immune based therapies such as passive (i.e., immunoglobulin) immunotherapy, or active immunization with antigens. Thus, in some embodiments, the invention provides methods that exploit the synergy that is achieved when the small molecule JFPB, JFPH, and/or functional equivalents are used together with antibodies or fragments thereof. In another aspect, the invention provides methods for stimulating an antigen specific immune response by administering a composition comprising JFPB, JFPH, and/or functional equivalents together with antigens. The antigens may be targeted to particular cell types or tissues (e.g., Corixa targeted antigens). These antibodies and antigens that can be used in the methods of the invention are not restricted to those that are cancer specific, and as described in greater detail herein can apply to a broad range of conditions (e.g., cancer, infectious disease, etc.).

A variety of functional equivalents of the small molecules JFPB and JFPH may be used in the compositions and methods of the present invention. For example, functional equivalents of the small molecules JFPB and JFPH may include, but are not limited to, molecules similar to JFPG and JFPH but with one or more different halogens (e.g., fluorine (F), bromine (Br), iodine (I), astatine (At)) substituted for the chlorine molecule (e.g., for JFPB) or chlorine molecules (e.g., for JFPH). Furthermore, molecules comprising replacement of the 8-membered ring of JFPH with other 5 (e.g., an azole), 6, or 7 membered ring structures (e.g., saturated cycles comprising carbon and/or oxygen within the ring) are also contemplated to be useful in the compositions and methods of the present invention. In some embodiments, a small molecule equivalent comprises two or more aryl groups connected by a linker. In some embodiments, the aryl group is selected from the group comprising a phenyl, a benzyl, a tolyl, and a xylyl. In some embodiments, one or more of the aryl groups comprise a heterocyclic compound. In some embodiments, the heterocyclic compound comprises sulfur, oxygen and/or nitrogen. In some embodiments, the heterocyclic compound is a pyrimidine. In some embodiments, the heterocyclic compound is a pyridine. In some embodiments, the heterocyclic compound is a dioxane. In some embodiments, the heterocyclic compound is a pyran. In some embodiments, the heterocyclic compound is a pyridazine. In some embodiments, the heterocyclic compound is a pyrazine. In some embodiments, the heterocyclic compound is a piperazine. In some embodiments, the aryl group is a quinoline. In some embodiments, the linker comprises nitrogen. In some embodiments, the linker comprises oxygen. In some embodiments, the linker comprises both nitrogen and oxygen. In some embodiments, the small molecule equivalent comprises a quinoline connected to a pyridine. In some embodiments, one or both of the aryl groups are functionalized with an alkyl, substituted alkyl, or additional aryl group. In some embodiments, the aryl groups, linkers, or alkyl groups comprise a ketone group.

In some embodiments, the present invention provides small molecules (e.g., JFPB, JFPH, and/or functional equivalents) that may be applied to chemotherapeutic strategies in targeting and eliminating cancer cells by the individuals own immune system with or without tumor vaccine therapy, can be used as standalone vaccines protecting against infectious or toxic agents, for treating infectious disease (e.g., antibiotic facilitator enhancing immune function), used as facilitators for immune clearance of persistent infections, for control of asthma and anaphylaxis and boosting immune compromised individual immune responses (e.g., chronic alcoholism). Compositions comprising JFPB, JFPH, and/or functional equivalents may also be used as a way of studying the role of CD154 in the immune system by the stabilization of CD154 trimerization. Thus, these small molecule compounds find use in both an applied clinical setting as well as basic research.

In some embodiments, the invention provides methods and products for the treatment of cancer using an agent comprising JFPB, JFPH, and/or functional equivalents in combination with cancer specific antibodies. In some embodiments, the combination is synergistic, resulting in greater than additive effects than would otherwise be expected using the agents separately. In other embodiments, the combination is additive.

Antibodies specific for tumor or cancer antigens can suppress tumor growth in vivo via a variety of mechanisms. Antibody dependent cell-mediated cytotoxicity, complement mediated cell lysis, targeting of chemically linked toxins, inhibition of tumor cell division, and induction of tumor cell apoptosis have all been described as mechanisms by which immunoglobulins specific for tumor antigens suppress tumor growth in the treatment of cancer. Although antibody-based treatments for cancer can be effective, they do not completely suppress tumor development and progression in all subjects.

In some embodiments, compositions comprising JFPB, JFPH, and/or functional equivalents suppress a number of different tumors. In some embodiments, administration of compositions comprising JFPB, JFPH, and/or functional equivalents stimulate the production of immune mediators (e.g., growth factors, cytokines and chemokines) (See, e.g., Examples 3-6). These mediators collectively stimulate the proliferation, activation and chemoattraction to the tumor microenvironment of effector cells involved in both non-adaptive (innate) and immune lysis or growth inhibition of tumor cells. The immune and non-immune effector cell populations mobilized and/or activated by compositions comprising JFPB, JFPH, and/or functional equivalents enhance the tumor suppressive effects of anti-cancer antibodies.

Examples of effector cells involved in the anti-tumor effects of compositions comprising JFPB, JFPH, and/or functional equivalents are provided below. Although not intending to be bound by any particular mechanism, a brief description of how each cell type can cooperate with tumor-specific antibodies in the lysis or growth inhibition of tumor cells is provided herein.

Tumor-infiltrating T cells, including cytotoxic T lymphocytes (CTL), that either lyse or inhibit tumor growth will suppress tumors by a mechanism of antigen-recognition that is different from that of antibodies. Thus, tumor-specific T cells can augment tumor cell lysis or growth inhibition initiated by antibody-based therapeutics.

In some embodiments, macrophage/monocyte, neutrophil, eosinophil, natural killer cells, and lymphokine activated killer cells are also activated by compositions comprising JFPB, JFPH, and/or functional equivalents. Individually or collectively, these effector cell types can either lyse tumor cells or suppress their growth in ligand-receptor mediated interactions that lack immunological specificity. The activities of these cells can account for the innate or non-adaptive immune responses against tumors stimulated by compositions comprising JFPB, JFPH, and/or functional equivalents. In addition, all of these cell types possess receptors that bind to the Fc portion of immunoglobulin and are referred to as Fc receptors. Fc receptors can bind to antibodies that are specifically bound to tumor cells by their antigen-binding regions. Therefore, since each effector cell possesses cytotoxicity or growth inhibitory activity against tumor cells, the antibody-mediated interaction targets this activity specifically against the tumor. The mechanism can therefore increase the efficiency with which these otherwise non-specific effector cells suppress tumor growth. The process is frequently referred to as antibody dependent cell-mediated cytotoxicity (ADCC).

Thus, in one aspect, the invention provides a method for stimulating ADCC in a subject. The method comprises administering an anti-cancer antibody or antibody fragment and a composition comprising JFPB, JFPH, and/or functional equivalents to a subject having or at risk of developing cancer in an amount effective to stimulate antibody dependent cell-mediated cytotoxicity in the subject. In some embodiments, the amount effective to stimulate antibody dependent cell-mediated cytotoxicity is a synergistic amount. In some embodiments, a composition comprising JFPB, JFPH, and/or functional equivalents are administered to a subject in combination with non-classical antibodies (e.g., camel/Llama therapeutics (e.g., from Ablynx) or mini-antibodies).

In some embodiments, a composition comprising JFPB, JFPH, and/or functional equivalents are administered to a subject in combination with a humanized antibody. In some embodiments, a composition comprising JFPB, JFPH, and/or functional equivalents are administered to a subject in combination with a genetically and/or structurally modified (e.g., PEGylated) antibody. In some embodiments, JFPB, JFPH, and/or functional equivalents are PEGylated.

In some embodiments, the invention provides methods for inducing mucosal immunity. The mucosal surface is frequently in contact with infectious pathogens such as bacteria, viruses and fungi, and thus an enhanced immune response at this surface would benefit a subject greatly. The compositions provided herewith could also be used for a variety of mucosal malignancies. Mucosal immunity generally involves immunoglobulin of the secretory IgA (s-IgA) isotype, and accordingly, antibodies of this isotype could be used together with the agents comprising JFPB, JFPH, and/or functional equivalents, although such antibodies are not so limited. The agents comprising JFPB, JFPH, and/or functional equivalents are useful in stimulating both cell-mediated immune responses and antibody-mediated immune responses at mucosal surfaces. Mucosal surfaces include oral, rectal, vaginal, gastrointestinal surfaces.

The novel observation that compositions comprising JFPB, JFPH, and/or functional equivalents induce the production of IL-2 and IFN-γ indicates that such small molecule compounds can be used for a number of indications that are mediated fully or in part by IL-2 and or INF-γ and downstream IL-2 and/or INF-γ signaling events. Some of these indications are recited herein as targets of combination therapy. It has been discovered according to the invention that some of these indications can also respond to sole compositions comprising JFPB, JFPH, and/or functional equivalents administration.

In some embodiments, compositions comprising JFPB, JFPH, and/or functional equivalents can be used either alone or in combination with other active agents to treat infections (e.g., bacterial or viral).

In some embodiments, compositions comprising JFPB, JFPH, and/or functional equivalents of the present invention are also suitable for treatment of hepatitis B infection. In this latter indication, compositions comprising JFPB, JFPH, and/or functional equivalents can be used alone or together with IFN as well as various small molecule drugs being developed, such as IFNα-2b, acyclovir, lobucavir, ganciclovir, L-deoxythymidine, clevudine, a therapeutic vaccine, phosphonoformate (PFA), ribavirin (RBV) and thymosin alpha-1; and nucleotide and nucleoside analogues such as 2 3-dideoxy-3-fluoroguanosine (FLG), famciclovir, lamivudine, adefovir dipivoxil, entecavir, and emtricitabine. In some embodiments, an agent comprising JFPB, JFPH, and/or functional equivalent is used with hepatitis B-specific immunoglobulin. In some embodiments, combined use of compositions comprising JFPB, JFPH, and/or functional equivalents with another small molecule drug can reduce or eliminate the risk of drug resistance.

Compositions comprising JFPB, JFPH, and/or functional equivalents can also be used in the treatment of tuberculosis, either alone (i.e., as a substitute for currently available drug treatments such as antibiotic therapy), or in combination with those antibiotics.

The ability of compositions comprising JFPB, JFPH, and/or functional equivalents to induce cytokines, and in particular IL-2 and IFN-γ (See, e.g., Examples 3, 4 and 6), also indicates that these compounds are useful in vaccine induced immunity, including both humoral and cell-mediated immunity. The ability to enhance cellular mediated immunity is useful, inter alia, in the treatment or prevention of viral infections, and in particular, HIV infection. As described in greater detail below, compositions comprising JFPB, JFPH, and/or functional equivalents can be used together with vaccines such as those to small pox virus (e.g., BVL).

Induction of IL-2 and IFN-γ indicates that compositions comprising JFPB, JFPH, and/or functional equivalents can be used to activate macrophages. This in turn can be exploited to reduce plaque formation in cardiovascular disease. Plaque engulfing macrophages can be activated following administration of compositions comprising JFPB, JFPH, and/or functional equivalents.

Indications relating to immune deficiency can also be treated using compositions comprising JFPB, JFPH, and/or functional equivalents. These indications include congenital deficiencies, some of which are described in greater detail herein. Examples include the syndromes commonly referred to as congenital disorder of glycosylation (CDG). Another congenital indication is the immunoglobulin deficiency common variable immunodeficiency (CVID) which is characterized by low IgG and IgA, and in some instances low IgM. Subjects having CVID can present with other clinical manifestations including gastrointestinal problems, granulomatous inflammation, cutaneous features, unusual presentations of enteroviral and mycoplasma infection, an increased incidence of autoimmunity, and a predisposition to lymphoma and stomach cancer. Other congenital indications include agammaglobulinemias such as Bruton's agammaglobulinemia and congenital hypogammaglobulinemia, selective immunoglobulin A deficiency, and severe combined immunodeficiency (i.e., SCID, a T cell deficiency). Immune deficiencies that include low or no immunoglobulin production can be treated using compositions comprising JFPB, JFPH, and/or functional equivalents alone, and in some instances, preferably with the antibodies described herein. Other immune deficiencies include amyotrophic lateral sclerosis (ALS), systemic lupus erythematosus, rheumatoid arthritis, Hashimoto's disease, chronic immune thrombocytopenic purpura (chronic ITP), and the like.

As indicated above, compositions comprising JFPB, JFPH, and/or functional equivalents are therapeutically and prophylactically useful for indications which are responsive to IFN therapy. The IFN therapy may be IFNα, IFNβ, or IFN-γ therapy, but is not so limited. A further example of this is multiple sclerosis. Others include tuberculosis, chronic Epstein Barr Virus (EBV) infection, and chronic hepatitis (e.g., chronic hepatitis C), viral hepatitis (e.g., hepatitis C), hepatocellular carcinoma, Kaposi's Sarcoma (AIDS-related), thick primary melanomas, and regional lymph node metastases. Examples of conditions responsive to IFN-γ therapy include, but are not limited to, viral infections and associated diseases and cancer.

One advantage of using compositions comprising JFPB, JFPH, and/or functional equivalents in place of IFN therapy is compositions comprising JFPB, JFPH, and/or functional equivalents are less expensive and easier to administer than IFN. These and other conditions can be immunosuppressive and therefore compositions comprising JFPB, JFPH, and/or functional equivalents can be used to enhance immunity in such subjects. Other chronic immunosuppressive conditions can arise from pharmaceutical use such as the use of deliberate anti-inflammatories such as cox-1 or cox-2 inhibitors celecoxib (Celebrex), rofecoxib (Vioxx), naproxen (Naprosyn), non-steroidal anti-inflammatory drugs (NSAIDS) such as ibuprofen (Motrin, Advil), fenoprofen, indomethacin, and valdecoxib (Bextra), and aspirin; substance abuse such as the alcoholism, intravenous drug use, morphine use; chronic infections or disease states such as gingivitis, osteomyelitis, diabetes types I and II, chronic granulomas, *Pneumocystis carinii pneumonia* pneumonia (PCP) infection, recurrent fungal/yeast infections, non-Hodgkin's lymphoma, and Kaposi's Sarcoma.

As a prophylaxis, compositions comprising JFPB, JFPH, and/or functional equivalents can be used to enhance immunity in a subject at risk of developing a condition that is immunologically responsive. For example, a subject may be administered a composition comprising JFPB, JFPH, and/or functional equivalents when it is at risk of developing the flu. As another example, a subject having or at risk of having angina may be administered a composition comprising JFPB, JFPH, and/or functional equivalents.

In some embodiments, depending upon the indication being treated or prevented, the compositions comprising JFPB, JFPH, and/or functional equivalents are combined, preferably in pharmaceutical form, with antibodies or fragments thereof or antigens. Compositions comprising JFPB, JFPH, and/or functional equivalents are of the structures shown in Example 5.

In some embodiments, certain methods and compositions comprise, in addition to the compositions comprising JFPB, JFPH, and/or functional equivalents, an antibody or fragment thereof. The invention embraces the use of antibodies of all isotypes including IgM, IgA1, IgA2, sigA, IgD, IgE, IgG1, IgG2, IgG3, and IgG4, having light chains that are either kappa or lambda chains.

The antibodies or fragments thereof useful in the invention can be specific for any component of a particular target. Accordingly, the antibody can recognize and bind to proteins, lipids, carbohydrates, DNA, RNA, and any combination of these in molecular or supra-molecular structures (e.g., cell organelles such as mitochondria or ribosomes). The antibody or fragment thereof can also recognize a modification of the tumor cell, such as e.g., chemical modifications, or genetic modifications made by transfection ex vivo or in vivo with DNA or RNA. As used herein, the terms "antibody" and "immunoglobulin" are used interchangeably.

Bispecific antibodies can also be used in the invention. A bispecific antibody is one having one variable region that specifically recognizes a tumor antigen and the other variable region that specifically recognizes an antigenic epitope of a host immune effector cell that has lytic or growth inhibitory activity against the tumor. Bispecific and multispecific antibody complexes can be created by linkage of two or more immunoglobulins of different specificity for tumor antigens and/or effector cell antigens, either at the peptide or nucleic acid level.

Immunoglobulin can be produced in vivo in human or nonhuman species, or in vitro from immunoglobulin encoding DNA or cDNA isolated from libraries of DNA (e.g., phage display libraries). Immunoglobulin can also be modified genetically or chemically to incorporate human polypeptide sequences into non-human coding sequences (commonly referred to as humanization). Additionally, immunoglobulins can be modified chemically or genetically to incorporate protein, lipid, or carbohydrate moieties. Potential modifications could also include naturally occurring or synthetic molecular entities that are either directly toxic for tumor cells or serve as ligands or receptors for biologically active molecules that could suppress tumor growth. For example, growth factors, cytokines, chemokines and their respective receptors, immunologically active ligands or receptors, hormones or naturally occurring or synthetic toxins all represent biologically active molecules that could interact with suitably modified immunoglobulins and their targets.

The antibody or antibody fragment may be conjugated (covalently or otherwise) to a toxin derived from plant, fungus, or bacteria. The toxin may be selected from the group consisting of A chain toxin, deglycosylated A chain toxin, ribosome inactivating protein, α-sarcin, aspergillin, restrictocin, ribonuclease, diptheria toxin and *Pseudomonas* exotoxin, but is not so limited.

The antibody or antibody fragment may also conjugated to a chemotherapeutic agent, a radioisotope such as those recited herein, or a cytotoxin. The chemotherapeutic agent may be selected from the group consisting of an anti-metabolite, an anthracycline, a vinca alkaloid, an antibiotic, an alkylating agent, and an epipodophyllotoxin, but is not so limited.

As used herein, an "anti-cancer antibody or fragment thereof" is an antibody or an antibody fragment that binds to a cancer or tumor antigen. The terms "cancer antigen" and "tumor antigen" are used interchangeably. A cancer antigen as used herein is a compound differentially associated with a tumor or cancer, preferably at the cell surface of a tumor or cancer cell, that is capable of invoking an immune response. The cancer antigen may be peptide in nature but it is not so limited. As an example, the antigen may be a lipid antigen, as described in U.S. Pat. No. 5,679,347, and U.S. Pat. No. 6,238,676 B1. If the antigen is a peptide, then it invokes an immune response when it is presented (in a digested form) on the surface of an antigen presenting cell in the context of an MHC molecule. If the antigen is a lipid, then it invokes an immune response when it is presented in the context of a CD1 molecule. Cancer antigens can be prepared from cancer cells either by preparing crude extracts of cancer cells (See, e.g., Cohen, et al., 1994, Cancer Research, 54:1055), by partially purifying the antigens, by recombinant technology, or by de novo synthesis of known antigens. Cancer antigens include but are not limited to antigens that are recombinantly expressed, an immunogenic portion of, or a whole tumor or cancer. Such antigens can be isolated or prepared recombinantly or by any other means known in the art.

A cancer antigen encompasses antigens that are differentially expressed between cancer and normal cells. Due to this differential expression, these antigens can be targeted in anti-tumor therapies. Cancer antigens may be expressed in a regulated manner in normal cells. For example, they may be expressed only at certain stages of differentiation or at certain points in development of the organism or cell. Some are temporally expressed as embryonic and fetal antigens. Still others are never expressed in normal cells, or their expression in such cells is so low as to be undetectable.

Other cancer antigens are encoded by mutant cellular genes, such as oncogenes (e.g., activated ras oncogene), suppressor genes (e.g., mutant p53), fusion proteins resulting from internal deletions or chromosomal translocations. Still other cancer antigens can be encoded by viral genes such as those carried on RNA and DNA tumor viruses.

Examples of cancer antigens include HER 2 (p185), CD20, CD33, GD3 ganglioside, GD2 ganglioside, carcinoembryonic antigen (CEA), CD22, milk mucin core protein, TAG-72, Lewis A antigen, ovarian associated antigens such as OV-TL3 and MOv18, high Mr melanoma antigens recognized by antibody 9.2.27, HMFG-2, SM-3, B72.3, PR5C5, PR4D2, and the like. Other cancer antigens are described in U.S. Pat. No. 5,776,427. Still other cancer antigens are listed in Table 1.

Further examples include MAGE, MART-1/Melan-A, gp100, Dipeptidyl peptidase IV (DPPIV), adenosine deaminase-binding protein (ADAbp), FAP, cyclophilin b, Colorectal associated antigen (CRC)-C017-1A/GA733, Carcinoembryonic Antigen (CEA) and its immunogenic epitopes CAP-1 and CAP-2, etv6, am11, Prostate Specific Antigen (PSA) and its immunogenic epitopes PSA-1, PSA-2, and PSA-3, prostate-specific membrane antigen (PSMA), T-cell receptor/CD3-zeta chain, MAGE-family of tumor antigens (e.g., MAGE-A1, MAGE-A2, MAGE-A3, MAGE-A4, MAGE-A5, MAGE-A6, MAGE-A7, MAGE-A8, MAGE-A9, MAGE-A10, MAGE-A11, MAGE-A12, MAGE-Xp2 (MAGE-B2), MAGE-Xp3 (MAGE-B3), MAGE-Xp4 (MAGE-B4), MAGE-C1, MAGE-C2, MAGE-C3, MAGE-C4, MAGE-C5), GAGE-family of tumor antigens (e.g., GAGE-1, GAGE-2, GAGE-3, GAGE-4, GAGE-5, GAGE-6, GAGE-7, GAGE-8, GAGE-9), BAGE, RAGE, LAGE-1, NAG, GnT-V, MUM-1, CDK4, tyrosinase, p53, MUC family, HER2/neu, p21ras, RCAS1, alpha.-fetoprotein, E-cadherin, .alpha.-catenin, .beta.-catenin and .gamma.-catenin, p120ctn, gp100.sup.Pme117, PRAME, NY-ESO-1, cdc27, adenomatous polyposis coli protein (APC), fodrin, Connexin 37, Ig-idiotype, p 15, gp75, GM2 and GD2 gangliosides, viral products such as human papilloma virus proteins, Smad family of tumor antigens, lmp-1, PIA, EBV-encoded nuclear antigen (EBNA)-1, brain glycogen phosphorylase, SSX-1, SSX-2 (HOM-MEL-40), SSX-1, SSX-4, SSX-5, SCP-I and CT-7, CD20 and c-erbB-2.

Cancer antigens are described in general in U.S. Pat. App. No. 20050084490, herein incorporated by reference in its entirety for all purposes.

Cancer or tumor antigens can also be classified according to the cancer or tumor they are associated with (i.e., expressed by). Cancers or tumors associated with tumor antigens include acute lymphoblastic leukemia (etv6; am11; cyclophilin b), B cell lymphoma (Ig-idiotype); Burkitt's (Non-Hodgkin's) lymphoma (CD20); glioma (E-cadherin; α-catenin; β-catenin; γ-catenin; p120ctn), bladder cancer (p21ras), biliary cancer (p21ras), breast cancer (MUC family; HER2/neu; c-erbB-2), cervical carcinoma (p53; p21ras), colon carcinoma (p21ras; HER2/neu; c-erbB-2; MUC family), colorectal cancer (Colorectal associated antigen (CRC)-C017-1A/GA733; APC), choriocarcinoma (CEA), epithelial cell-cancer (cyclophilin b), gastric cancer (HER2/neu; c-erbB-2; ga733 glycoprotein), hepatocellular cancer (α-fetoprotein), Hodgkin's lymphoma (lmp-1; EBNA-1), lung cancer (CEA; MAGE-3; NY-ESO-1), lymphoid cell-derived leukemia (cyclophilin b), melanoma (p15 protein, gp75, oncofetal antigen, GM2 and GD2 gangliosides), myeloma (MUC family; p21 ras), non-small cell lung carcinoma (HER2/neu; c-erbB-2), nasopharyngeal cancer (lmp-1; EBNA-1), ovarian cancer (MUC family; HER2/neu; c-erbB-2), prostate cancer (Prostate Specific Antigen (PSA) and its immunogenic epitopes PSA-1, PSA-2, and PSA-3; PSMA; HER2/neu; c-erbB-2), pancreatic cancer (p21ras; MUC family; HER2/neu; c-erbB-2; ga733 glycoprotein), renal (HER2/neu; c-erbB-2), squamous cell cancers of cervix and esophagus (viral products such as human papilloma virus proteins and non-infectious particles), testicular cancer (NY-ESO-1), T cell leukemia (HTLV-1 epitopes), and melanoma (Melan-A/MART-1; cdc27; MAGE-3; p21ras; gp100.sup.Pme117).

For examples of tumor antigens that bind to either or both MHC class I and MHC class II molecules, see the following references: Coulie, Stem Cells 13:393-403, 1995; Traversari et al., J. Exp. Med. 176:1453-1457, 1992; Chaux et al., J. Immunol. 163:2928-2936, 1999; Fujie et al., Int. J. Cancer 80:169-172, 1999; Tanzarella et al., Cancer Res. 59:2668-2674, 1999; van der Bruggen et al., Eur. J. Immunol. 24:2134-2140, 1994; Chaux et al., J. Exp. Med. 189:767-778, 1999; Kawashima et al, Hum. Immunol. 59:1-14, 1998; Tahara et al., Clin. Cancer Res. 5:2236-2241, 1999; Gaugler et al., J. Exp. Med. 179:921-930, 1994; van der Bruggen et al., Eur. J. Immunol. 24:3038-3043, 1994; Tanaka et al., Cancer Res. 57:4465-4468, 1997; Oiso et al., Int. J. Cancer 81:387-394, 1999; Herman et al., Innumogenetics 43:377-383, 1996; Manici et al., J. Exp. Med. 189:871-876, 1999; Duffour et al., Eur. J. Immunol. 29:3329-3337, 1999; Zom et al., Eur. J. Immunol. 29:602-607, 1999; Huang et al., J. Immunol. 162:6849-6854, 1999; Boel et al., Immunity 2:167-175, 1995; Van den Eynde et al., J. Exp. Med. 182:689-698, 1995; De Backer et al., Cancer Res. 59:3157-3165, 1999; Jager et al., J. Exp. Med. 187:265-270, 1998; Wang et al., J. Immunol. 161:3596-3606, 1998; Aarnoudse et al., Int. J. Cancer 82:442-448, 1999; Guilloux et al., J. Exp. Med. 183:1173-1183, 1996; Lupetti et al., J. Exp. Med. 188:1005-1016, 1998; Wolfel et al., Eur. J. Immunol. 24:759-764, 1994; Skipper et al., J. Exp. Med. 183:527-534, 1996; Kang et al., J. Immunol. 155:1343-1348, 1995; Morel et al., Int. J. Cancer 83:755-759, 1999; Brichard et al., Eur. J. Immunol. 26:224-230, 1996; Kittlesen et al., J. Immunol. 160:2099-2106, 1998; Kawakami et al., J. Immunol. 161:6985-6992, 1998; Topalian et al., J. Exp. Med. 183:1965-1971, 1996; Kobayashi et al., Cancer Research 58:296-301, 1998; Kawakami et al., J. Immunol. 154:3961-3968, 1995; Tsai et al., J. Immunol. 158:1796-1802, 1997; Cox et al., Science 264:716-719, 1994; Kawakami et al., Proc. Natl. Acad. Sci. USA 91:6458-6462, 1994; Skipper et al., J. Immunol. 157:5027-5033, 1996; Robbins et al., J. Immunol. 159:303-308, 1997; Castelli et al, J. Immunol. 162:1739-1748, 1999; Kawakami et al., J. Exp. Med. 180: 347-352, 1994; Castelli et al., J. Exp. Med. 181:363-368, 1995; Schneider et al., Int. J. Cancer 75:451-458, 1998; Wang et al., J. Exp. Med 183:1131-1140, 1996; Wang et al., J. Exp. Med. 184:2207-2216, 1996; Parkhurst et al., Cancer Research 58:4895-4901, 1998; Tsang et al., J. Natl Cancer Inst 87:982-990, 1995; Correale et al., J. Natl Cancer Inst 89:293-300, 1997; Coulie et al., Proc. Natl. Acad. Sci. USA 92:7976-7980, 1995; Wolfel et al., Science 269:1281-1284, 1995; Robbins et al., J. Exp. Med. 183:1185-1192, 1996; Brandle et al., J. Exp. Med. 183:2501-2508, 1996; ten Bosch et al., Blood 88:3522-3527, 1996; Mandruzzato et al., J. Exp. Med. 186:785-793, 1997; Gueguen et al., J. Immunol. 160:6188-6194, 1998; Gjertsen et al., Int. J. Cancer 72:784-790, 1997; Gaudin et al., J. Immunol. 162:1730-1738, 1999; Chiari et al., Cancer Res. 59:5785-5792, 1999; Hogan et al., Cancer Res. 58:5144-5150, 1998; Pieper et al., J. Exp. Med. 189:757-765, 1999; Wang et al., Science 284:1351-1354, 1999; Fisk et al., J. Exp. Med. 181:2109-2117, 1995; Brossart et al., Cancer Res. 58:732-736, 1998; Ropke et al., Proc. Natl. Acad. Sci. USA 93:14704-14707, 1996; Ikeda et al., Immunity 6:199-208, 1997; Ronsin et al., J. Immunol. 163:483-490, 1999; Vonderheide et al., Immunity 10:673-679,1999. These antigens as well as others are disclosed in PCT Application PCT/US98/18601.

In some embodiments, the antigens are administered in a substantially purified form. The term "substantially purified" as used herein refers to a compound which is substantially free of other compounds such as proteins, lipids, carbohydrates or other materials with which it is naturally associated. One skilled in the art can purify viral or bacterial compounds such as polypeptides using standard techniques such as for example protein purification. The substantially pure polypeptide will often yield a single major band on a non-reducing polyacrylamide gel. In the case of partially glycosylated polypeptides or those that have several start codons, there may be several bands on a non-reducing polyacrylamide gel, but these will form a distinctive pattern for that polypeptide. The purity of the viral or bacterial polypeptide can also be determined by amino-terminal amino acid sequence analysis.

In some embodiments, compositions comprising JFPB, JFPH, and/or functional equivalents can be used in combination with various vaccines either currently being used or in development, whether intended for human or non-human subjects. Examples of vaccines for human subjects and directed to infectious diseases include the combined diphtheria and tetanus toxoids vaccine; pertussis whole cell vaccine; the inactivated influenza vaccine; the 23-valent pneumococcal vaccine; the live measles vaccine; the live mumps vaccine; live rubella vaccine; Bacille Calmette-Guerin (BCG) tuberculosis vaccine; hepatitis A vaccine; hepatitis B vaccine; hepatitis C vaccine; rabies vaccine (e.g., human diploid cell vaccine); inactivated polio vaccine; meningococcal polysaccharide vaccine; quadrivalent meningococcal vaccine; yellow fever live virus vaccine; typhoid killed whole cell vaccine; cholera vaccine; Japanese B encephalitis killed virus vaccine; adenovirus vaccine; cytomegalovirus vaccine; rotavirus vaccine; varicella vaccine; anthrax vaccine; small pox vaccine.

In some embodiments, compositions comprising JFPB, JFPH, and/or functional equivalents can be administered after viral, bacterial mycobacterial, fungal, or parasitic infection in order to stimulate innate immunity (i.e., immunity mediated by neutrophils, macrophages, NK cells and eosinophils) and/or adaptive immunity (i.e., immunity mediated by T cells and B cells). The growth factors, cytokines and chemokines stimulated by compositions comprising JFPB, JFPH, and/or functional equivalents can stimulate these cells and thereby enhance an immune response to a foreign pathogen. As an example, IL-2 and IFN-γ rapidly activates innate immunity. Therefore, compositions comprising JFPB, JFPH, and/or functional equivalents can be used to activate innate immunity via cytokine (e.g., IL-2 or IFN-γ induction, See, e.g., Examples 3, 4, and 6), and this in turn can provide an initial defense against any infectious agent.

In some embodiments, compositions comprising JFPB, JFPH, and/or functional equivalents are used prophylactically to prevent infection during periods of heightened risk, including for example flu season, epidemics, and travel to places where the risk of pathogen exposure is high. Many of the cytokines and chemokines induced compositions comprising JFPB, JFPH, and/or functional equivalents can prime a subject and prepare it for passive exposure to a pathogen. The rate at which compositions comprising JFPB, JFPH, and/or functional equivalents stimulate cytokines and chemokines is useful particularly where pathogen exposure cannot be anticipated.

Thus, the methods of the present invention can be used in the treatment or prevention of infectious diseases such as bacterial infections, mycobacterial infections, viral infections, fungal infections and parasitic infections.

Examples of bacterial infections include *E. coli, Streptococcal* infections, *Staphylococcal* infections, *Pseudomonas* infections, *Clostridium difficile, Legionella* infections, *Pneumococcus* infection, *Haemophilus* infections (e.g., *Haemophilus influenzae* infections), *Klebsiella* infections, *Enterobacter* infections, *Citrobacter* infections, *Neisseria* infections (e.g., *N. meningitidis* infection, *N. gonorrhoeae* infection), *Shigella* infections, *Salmonella* infections, *Listeria* infections (e.g., *L. monocytogenes* infection), *Pasteurella* infection (e.g., *Pasteurella multocida* infection), *Streptobacillus* infection, *Spirillum* infection, *Treponema* infection (e.g., *Treponema pallidum* infection), *Actinomyces* infection (e.g., *Actinomyces israelli* infection), *Borrelia* infection, *Corynebacterium* infection, *Nocardia* infection, *Gardnerella* infections (e.g., *Gardnerella* vaginal is infection), *Campylobacter* infections (e.g., *Campylobacter fetus* infection), *Spirochaeta* infections, Proteus infections, *Bacteriodes* infections, *H. pylori*, and *anthrax*.

Examples of viral infections include HIV infection, Herpes simplex virus 1 and 2 infections (including encephalitis, neonatal and genital forms), human papilloma virus infection, cytomegalovirus infection, Epstein Barr virus infection, Hepatitis virus A, B and C infections, rotavirus infection, adenovirus infection, influenza A virus infection, respiratory syncytial virus infection, varicella-zoster virus infections, small pox infection, monkey pox infection and SARS infection.

Examples of fungal infections include candidiasis infection, ringworm, histoplasmosis infection, blastomycosis infections, paracoccidioidomycosis infections, crytococcosis infections, aspergillosis infections, chromomycosis infections, mycetomna infections, pseudallescheriasis infection, and tinea versicolor infection.

Examples of parasite infections include both protozoan infections and nematode infections. These include amebiasis, *Trypanosoma cruzi* infection (i.e., Chagas' disease), Fascioliasis (e.g., Facioloa hepatica infection), Leishmaniasis, *Plasmodium* infections (e.g., malaria causing *Plasmodium* species infections, e.g., *P. falciparum, P. knowlesi, P. malariae,*) Onchocerciasis, Paragonimiasis, *Trypanosoma brucei* infection (i.e., Sleeping sickness), *Pneumocystis* infection (e.g.,

*Pneumocystis carinii* infection), *Trichomonas vaginalis* infection, *Taenia* infections, *Hymenolepsis* infections (e.g., *Hymenolepsis nana* infection), *Echinococcus* infections, Schistosomiasis (e.g., *Schistosoma mansoni* infection), neurocysticercosis, *Necator americanus* infection, and *Trichuris trichuria* infections.

Other infections that can be treated according to the methods of the invention include *Chlamydia* infection, Mycobacterial infection such as tuberculosis and leprosy, and Rickettsiae.

The foregoing lists of infections are not intended to be exhaustive but rather exemplary. Those of ordinary skill in the art will identify other infections that are amenable to prevention and treatment using the compositions and methods of the invention.

Antigens associated with infectious diseases that can be used in the methods of the invention include whole bacteria, whole virus, whole fungi, whole parasites, and fragments thereof. Examples include non-infectious human papillomavirus-like particles (VLP) (which can be used as a cancer antigen as well, particularly for cervical cancer); and the like.

Subjects having an infectious disease are those that exhibit symptoms of infectious disease (e.g., rapid onset, fever, chills, myalgia, photophobia, pharyngitis, acute lymphadenopathy, splenomegaly, gastrointestinal upset, leukocytosis or leukopenia) and in whom infectious pathogens or byproducts thereof can be detected. Tests for diagnosing infectious diseases are known in the art and the ordinary medical practitioner will be familiar with these laboratory tests which include but are not limited to microscopic analyses, cultivation dependent tests (such as cultures), and nucleic acid detection tests. These include wet mounts, stain-enhanced microscopy, immune microscopy (e.g., FISH), hybridization microscopy, particle agglutination, enzyme-linked immunosorbent assays, urine screening tests, DNA probe hybridization, serologic tests, etc. The medical practitioner will generally also take a full history and conduct a complete physical examination in addition to running the laboratory tests listed above.

A subject at risk of developing an infectious disease is one that is at risk of exposure to an infectious pathogen. Such subjects include those that live in an area where such pathogens are known to exist and where such infections are common. These subjects also include those that engage in high risk activities such as sharing of needles, engaging in unprotected sexual activity, routine contact with infected samples of subjects (e.g., medical practitioners), people who have undergone surgery, including but not limited to abdominal surgery, etc.

In some embodiments, compositions comprising JFPB, JFPH, and/or functional equivalents are used for treatment of human papillomavirus (HPV) infection. The current therapy for HPV is injection of IFN into a lesion and/or surgical ablation. A systemic treatment such as that envisioned for compositions comprising JFPB, JFPH, and/or functional equivalents, particularly when administered orally, would be desirable in comparison with current clinical therapies. Compositions comprising JFPB, JFPH, and/or functional equivalents are similarly useful in combination with HPV vaccines currently in development such as HPV virus-like particle (VLP)-based vaccine (see, for example, Virology 2000 Jan. 20; 266(2):237-45).

In still further aspects, the invention contemplates the use of compositions comprising JFPB, JFPH, and/or functional equivalents together with anti-microbial agents (e.g., anti-bacterial agents or anti-viral agents) in order to reduce the risk of drug resistance by the microbial species, or for treatment following incidence of drug resistance.

The invention intends to treat subjects that are not immunocompromised in some instances. Subject that are not immunocompromised (i.e., "non-immunocompromised") are those that have blood cell counts in the normal range. Normal ranges of blood counts are known to the medical practitioner and reference can be made to a standard hematology textbook for such counts. In addition, reference can be made to published PCT application PCT/US00/14505. Non-immunocompromised subjects can include subjects that have not undergone any treatment that would render them immunocompromised. For example, such subjects may have a cancer but they have not undergone any treatment such as chemotherapy or radiation that would render them immunocompromised. Such subjects also would not inherently be immunocompromised as a result of the cancer. In some important embodiments, the subjects are at risk of developing an infection due to an impending surgical procedure, travel to a region where one or more infections are common, or they have experienced a skin abrasion, for example as a result of a trauma.

In still other embodiments, the subjects may be genetically immunocompromised, meaning that they harbor a genetic mutation that renders them immunocompromised even in the absence of an infectious or exogenous procedure. Such subjects may have for example a genetic mutation such as in agammaglobulinemia or SCID. These subjects may be treated according to the invention routinely or only when they are at a higher risk of developing an infectious disease e.g., when traveling to a region where infections are common, when having surgery, when having a skin abrasion, etc.

In still other embodiments, the methods taught herein are intended for use in elderly subjects. As used herein, an elderly subject is one that is at least 50 years old, preferably at least 60 years old, more preferably at least 70 years old, and most preferably at least 75 years old.

In some embodiments, the compositions provided herein can further include other therapeutic agents such as antimicrobials agents, if the disease is an infectious disease, or anti-cancer agents if the disease is a cancer. Examples of anti-microbials include anti-bacterials, anti-mycobacterials, anti-virals, anti-fungal, and anti-parasites.

Examples of anti-bacterials include, but are not limited to, β-lactam antibiotics, penicillins (such as natural penicillins, aminopenicillins, penicillinase-resistant penicillins, carboxy penicillins, ureido penicillins), cephalosporins (first generation, second generation, and third generation cephalosporins), and other β-lactams (such as imipenem, monobactams,), β-lactamase inhibitors, vancomycin, aminoglycosides and spectinomycin, tetracyclines, chloramphenicol, erythromycin, lincomycin, clindamycin, rifampin, metronidazole, polymyxins, sulfonamides and trimethoprim, and quinolines.

Anti-bacterials include, but are not limited to: Acedapsone; Acetosulfone Sodium; Alamecin; Alexidine; Amdinocillin; Amdinocillin Pivoxil; Amicycline; Amifloxacin; Amifloxacin Mesylate; Amikacin; Amikacin Sulfate; Aminosalicylic acid; Aminosalicylate sodium; Amoxicillin; Amphomycin; Ampicillin; Ampicillin Sodium; Apalcillin Sodium; Apramycin; Aspartocin; Astromicin Sulfate; Avilamycin; Avoparcin; Azithromycin; Azlocillin; Azlocillin Sodium; Bacampicillin Hydrochloride; Bacitracin; Bacitracin Methylene Disalicylate; Bacitracin Zinc; Bambermycins; Benzoylpas Calcium; Berythromycin; Betamicin Sulfate; Biapenem; Biniramycin; Biphenamine Hydrochloride; Bispyrithione Magsulfex; Butikacin; Butirosin Sulfate; Capreomycin Sulfate; Carbadox; Carbenicillin Disodium; Carbenicillin Indanyl Sodium; Carbenicillin Phenyl Sodium; Carbenicillin Potassium; Carumonam Sodium; Cefaclor; Cefadroxil; Cefamandole;

Cefamandole Nafate; Cefamandole Sodium; Cefaparole; Cefatrizine; Cefazaflur Sodium; Cefazolin; Cefazolin Sodium; Cefbuperazone; Cefdinir; Cefepime; Cefepime Hydrochloride; Cefetecol; Cefixime; Cefmenoxime Hydrochloride; Cefinetazole; Cefinetazole Sodium; Cefonicid Monosodium; Cefonicid Sodium; Cefoperazone Sodium; Ceforanide; Cefotaxime Sodium; Cefotetan; Cefotetan Disodium; Cefotiam Hydrochloride; Cefoxitin; Cefoxitin Sodium; Cefpimizole; Cefpimizole Sodium; Cefpiramide; Cefpiramide Sodium; Cefpirome Sulfate; Cefpodoxime Proxetil; Cefprozil; Cefroxadine; Cefsulodin Sodium; Ceftazidime; Ceftibuten; Ceftizoxime Sodium; Ceftriaxone Sodium; Cefuroxime; Cefuroxime Axetil; Cefuroxime Pivoxetil; Cefuroxime Sodium; Cephacetrile Sodium; Cephalexin; Cephalexii Hydrochloride; Cephaloglycini; Cephaloridine; Cephalothin Sodium; Cephapirin Sodium; Cephradine; Cetocycline Hydrochloride; Cetophenicol; Chloramphenicol; Cliloramphenicol Palmitate; Chloramphenicol Pantotheniate Complex; Chloramphenicol Sodium Succinate; Chlorhexidine Phosphanilate; Chloroxylenol; Chlortetracycline Bisulfate; Chlortetracycline Hydrochloride; Cinoxacin; Ciprofloxacin; Ciprofloxacin Hydrochloride; Cirolemycin; Clarithromycin; Clinafloxacin Hydrochloride; Clildamycin; Clindamycin Hydrochloride; Clindamycin Palmitate Hydrochloride; Clindamycin Phosphate; Clofazimine; Cloxacillin Benzathine; Cloxacillin Sodium; Cloxyquin; Colistimethate Sodium; Colistin Sulfate; Coumermycin; Coumermycin Sodium; Cyclacillin; Cycloserine; Dalfopristin; Dapsone; Daptomycin; Demeclocycine; Demeclocycine Hydrochloride; Demecycline; Denofungin; Diaveridine; Dicloxacillin; Dicloxacillin Sodium; Dihydrostreptomycin Sulfate; Dipyrithione; Dirithromycin; Doxycycline; Doxycycline Calcium; Doxycycline Fosfatex; Doxycycline Hyclate; Droxacin Sodium; Enoxacin; Epicillin; Epitetracycline Hydrochloride; Erythromycin; Erythromycin Acistrate; Erythromycin Estolate; Erythromycin Ethylsuccinate; Erythromycin Gluceptate; Erythromycin Lactobionate; Erythromycin Propionate; Erythromycin Stearate; Ethambutol Hydrochloride; Ethionamide; Fleroxacin; Floxacillin; Fludalanine; Flumequine; Fosfomycin; Fosfomycin Tromethamine; Fumoxicillin; Furazolium Chloride; Furazolium Tartrate; Fusidate Sodium; Fusidic Acid; Gentamicin Sulfate; Gloximonam; Gramicidin; Haloprogin; Hetacillin; Hetacillin Potassium; Hexedine; Ibafloxacin; Imipenem; Isoconazole; Isepamicin; Isoniazid; Josamycin; Kanamycin Sulfate; Kitasamycin; Levofuraltadone; Levopropylcillin Potassium; Lexithromycin; Lincomycin; Lincomycin Hydrochloride; Lomefloxacin; Lomefloxacin Hydrochloride; Lomefloxacin Mesylate; Loracarbef; Mafenide; Meclocycline; Meclocycline Sulfosalicylate; Megalomicin Potassium Phosphate; Mequidox; Meropenem; Methacycline; Methacycline Hydrochloride; Methenamine; Methenamine Hippurate; Methenamine Mandelate; Methicillin Sodium; Metioprim; Metronidazole Hydrochloride; Metronidazole Phosphate; Mezlocillin; Mezlocillin Sodium; Minocycline; Minocycline Hydrochloride; Mirincamycin Hydrochloride; Monensin; Monensin Sodium; Nafcillin Sodium; Nalidixate Sodium; Nalidixic Acid; Natamycin; Nebramycin; Neomycin Palmitate; Neomycin Sulfate; Neomycin Undecylenate; Netilmicin Sulfate; Neutramycin; Nifuradene; Nifuraldezone; Nifuratel; Nifuratrone; Nifurdazil; Nifurimide; Nifuirpirinol; Nifurquinazol; Nifurthiazole; Nitrocycline; Nitrofurantoin; Nitromide; Norfloxacin; Novobiocin Sodium; Ofloxacin; Ormetoprim; Oxacillin Sodium; Oximonam; Oximonam Sodium; Oxolinic Acid; Oxytetracycline; Oxytetracycline Calcium; Oxytetracycline Hydrochloride; Paldimycin; Parachlorophenol; Paulomycin; Pefloxacin; Pefloxacin Mesylate; Penamecillin; Penicillin G Benzathine; Penicillin G Potassium; Penicillin G Procaine; Penicillin G Sodium; Penicillin V; Penicillin V Benzathine; Penicillin V Hydrabamine; Penicillin V Potassium; Pentizidone Sodium; Phenyl Aminosalicylate; Piperacillin Sodium; Pirbenicillin Sodium; Piridicillin Sodium; Pirlimycin Hydrochloride; Pivampicillin Hydrochloride; Pivampicillin Pamoate; Pivampicillin Probenate; Polymyxin B Sulfate; Porfiromycin; Propikacin; Pyrazinamide; Pyrithione Zinc; Quindecamine Acetate; Quinupristin; Racephenicol; Ramoplanin; Ranimycin; Relomycin; Repromicin; Rifabutin; Rifametane; Rifamexil; Rifamide; Rifampin; Rifapentine; Rifaximin; Rolitetracycline; Rolitetracycline Nitrate; Rosaramicin; Rosaramicin Butyrate; Rosaramicin Propionate; Rosaramicin Sodium Phosphate; Rosaramicin Stearate; Rosoxacin; Roxarsone; Roxithromycin; Sancycline; Sanfetrinem Sodium; Sarmoxicillin; Sarpicillin; Scopafungin; Sisomicin; Sisomicin Sulfate; Sparfloxacin; Spectinomycin Hydrochloride; Spiramycin; Stallimycin Hydrochloride; Steffimycin; Streptomycin Sulfate; Streptonicozid; Sulfabenz; Sulfabenzamide; Sulfacetamide; Sulfacetamide Sodium; Sulfacytine; Sulfadiazine; Sulfadiazine Sodium; Sulfadoxine; Sulfalene; Sulfamerazine; Sulfameter; Sulfamethazine; Sulfamethizole; Sulfamethoxazole; Sulfamonomethoxine; Sulfamoxole; Sulfanilate Zinc; Sulfanitran; Sulfasalazine; Sulfasomizole; Sulfathiazole; Sulfazamet; Sulfisoxazole; Sulfisoxazole Acetyl; Sulfisoxazole Diolamine; Sulfomyxin; Sulopenem; Sultamicillin; Suncillin Sodium; Talampicillin Hydrochloride; Teicoplanin; Temafloxacin Hydrochloride; Temocillin; Tetracycline; Tetracycline Hydrochloride; Tetracycline Phosphate Complex; Tetroxoprim; Thiamphenicol; Thiphencillin Potassium; Ticarcillin Cresyl Sodium; Ticarcillin Disodium; Ticarcillin Monosodium; Ticlatone; Tiodonium Chloride; Tobramycin; Tobramycin Sulfate; Tosufloxacin; Trimethoprim; Trimethoprim Sulfate; Trisulfapyrimidines; Troleandomycin; Trospectomycin Sulfate; Tyrothricin; Vancomycin; Vancomycin Hydrochloride; Virginiamycin; Zorbamycin.

Anti-mycobacterials include, but are not limited to, Myambutol (Ethambutol Hydrochloride), Dapsone (4,4'-diaminodiphenylsulfone), Paser Granules (aminosalicylic acid granules), rifapentine, Pyrazinamide, Isoniazid, Rifampin, Rifadin IV, Rifampin and Isoniazid, Rifampin, Isoniazid, and Pyrazinamide, Streptomycin Sulfate and Trecator-SC (Ethionamide).

Anti-virals include, but are not limited to, amantidine and rimantadine, ribivarin, acyclovir, vidarabine, trifluorothymidine, ganciclovir, zidovudine, retinovir, and interferons.

Anti-virals further include: Acemannan; Acyclovir; Acyclovir Sodium; Adefovir; Alovudine; Alvircept Sudotox; Amantadine Hydrochloride; Aranotin; Arildone; Atevirdine Mesylate; Avridine; Cidofovir; Cipamfylline; Cytarabine Hydrochloride; Delavirdine Mesylate; Desciclovir; Didanosine; Disoxaril; Edoxudine; Enviradene; Enviroxime; Famciclovir; Famotine Hydrochloride; Fiacitabine; Fialuridine; Fosarilate; Foscarnet Sodium; Fosfonet Sodium; Ganciclovir; Ganciclovir Sodium; Idoxuridine; Kethoxal; Lamivudine; Lobucavir; Memotine Hydrochloride; Methisazone; Nevirapine; Penciclovir; Pirodavir; Ribavirin; Rimantadine Hydrochloride; Saquinavir Mesylate; Soinantadine Hydrochloride; Sorivudine; Statolon; Stavudine; Tilorone Hydrochloride; Trifluridine; Valacyclovir Hydrochloride; Vidarabine; Vidarabine Phosphate; Vidarabine Sodium Phosphate; Viroxime; Zalcitabine; Zidovudine; Zinviroxime and integrase inhibitors.

Anti-fungals include, but are not limited to, imidazoles and triazoles, polyene macrolide antibiotics, griseofulvin, amphotericin B, and flucytosine. Antiparasites include heavy metals, antimalarial quinolines, folate antagonists, nitroimidazoles, benzimidazoles, avermectins, praxiquantel, ornithine decarboxylase inhbitors, phenols (e.g., bithionol, niclosamide); synthetic alkaloid (e.g., dehydroemetine); piperazines (e.g., diethylcarbamazine); acetanilide (e.g., diloxanide furonate); halogenated quinolines (e.g., iodoquinol (di-iodohydroxyquin)); nitrofurans (e.g., nifurtimox); diamidines (e.g., pentamidine); tetrahydropyrimidine (e.g., pyrantel pamoate); sulfated naphthylamine (e.g., suramin).

Other anti-infectives include Difloxacin Hydrochloride; Lauryl Isoquinolinium Bromide; Moxalactam Disodium; Ornidazole; Pentisomicin; Sarafloxacin Hydrochloride; Protease inhibitors of HIV and other retroviruses; Integrase Inhibitors of HIV and other retroviruses; Cefaclor (Ceclor); Acyclovir (Zovirax); Norfloxacin (Noroxin); Cefoxitin (Mefoxin); Cefuroxime axetil (Ceftin); Ciprofloxacin (Cipro); Aininacrine Hydrochloride; Benzethonium Chloride: Bithionolate Sodium; Bromchlorenone; Carbamide Peroxide; Cetalkonium Chloride; Cetylpyridinium Chloride: Chlorhexidine Hydrochloride; Clioquinol; Domiphen Bromide; Fenticlor; Fludazonium Chloride; Fuchsin, Basic; Furazolidone; Gentian Violet; Halquinols; Hexachlorophene: Hydrogen Peroxide; Ichthammol; Imidecyl Iodine; Iodine; Isopropyl Alcohol; Mafenide Acetate; Meralein Sodium; Mercufenol Chloride; Mercury, Ammoniated; Methylbenzethonium Chloride; Nitrofurazone; Nitromersol; Octenidine Hydrochloride; Oxychlorosene; Oxychlorosene Sodium; Parachlorophenol, Camphorated; Potassium Permanganate; Povidone-Iodine; Sepazonium Chloride; Silver Nitrate; Sulfadiazine, Silver; Symclosene; Thimerfonate Sodium; Thimerosal: Troclosene Potassium.

Antibodies that can be used with an agent comprising JFPB, JFPH, and/or functional equivalents include those useful in cancer and infectious disease as well as other disorders for which antibodies and antigens have been identified and which would benefit from an enhanced immune response.

In some embodiments, an agent comprising JFPB, JFPH, and/or functional equivalents is used with normal and hyper-immune globulin therapy. Normal immune globulin therapy utilizes an antibody product from the serum of normal blood donors. This pooled product contains low titers of antibody to a wide range of antigens such as those of infectious pathogens (e.g., bacteria, viruses such as hepatitis A, parvovirus, enterovirus, fungi and parasites). Hyper-immune globulin therapy utilizes antibodies which are prepared from the serum of individuals who have high titers of an antibody to a particular antigen. The antibodies may be those that are currently used or in development for treating infectious diseases. Examples include zoster immune globulin (useful for the prevention of varicella-zoster in immunocompromised children and neonates), human rabies immunoglobulin (useful in the post-exposure prophylaxis of a subject bitten by a rabid animal), hepatitis A or B immune globulin (useful in the prevention of hepatitis A or B virus, especially in a subject exposed to the virus), RSV immune globulin (useful in the treatment of respiratory syncitial virus infections), tetanus immunoglobulin; measles immunoglobulin (useful in the prevention of infection in immunocompromised or adult subjects); rubella immunoglobulin (useful in the prevention of infection in pregnant female subjects).

Other antibodies for infectious diseases include anti-shiga toxin antibodies, anti-staphylococcal antibodies (Virion Systems), and the like.

Antibodies specific for CD20 include Rituxan, IDEC-Y2B8. Antibodies specific for HER2/neu include Herceptin.

Some commercially available anti-cancer antibodies along with their commercial source are as follows: anti-CD20 mAb (monoclonal antibody), rituximab, Rituxan, Non-Hodgkin's lymphoma, B cell lymphoma (IDEC/Genentech); anti-CD20 mAb, tositumomab Bexxar, Non-Hodgkin's lymphoma (Corixa/GlaxoSmithKline); anti-HER2, trastuzumab, Herceptin, breast and ovarian cancer (Genentech); anti-HER2, MDX-210, prostate, non-small cell lung cancer, breast, pancreatic, ovarian, renal and colon cancer (Medarex/Novartis); anti-CA 125 mAb, oregovoinab, B43.13, Ovarex, ovarian cancer (Altarex); Breva-Rex, multiple myeloma, breast, lung, ovarian (Altarex); AR54, ovarian, breast, lung (Altarex); GivaRex, pancreas, stomach, colorectal (Altarex); ProstaRex, prostate (Altarex); anti-EGF receptor mAb, IMC-C225, Erbitux, breast, head and neck, non-small cell lung, renal, prostate, colorectal and pancreatic cancer (ImClone Systems); anti-EGF receptor mAb, MDX-447, head and neck, prostate, lung, bladder, cervical, ovarian cancer (Medarex/Merck); gemtuzumab ozogamicin, Mylotarg, CMA-676, anti-CD33 (Wyeth Pharmaceuticals); anti-tissue factor protein (TF), (Sunol); ior-c5, colorectal cancer; ceal, colorectal cancer; c5, colorectal cancer; anti-EGF receptor mAb, MDX-447, head and neck, prostate, lung, bladder, cervical and ovarian cancer (Medarex/Merck); anti-17-1A mAb, edrecolomab, Panorex, colorectal, pancreatic, lung, breast and ovarian cancer (Centocor/Glaxo/Ajinomoto); anti-CD20 mAb (Y-90 labeled), ibritumomab tiuxetan (IDEC-Y2B8), Zevalin, Non-Hodgkin's lymphoma (IDEC); anti-idiotypic mAb mimic of ganglioside GD3 epitope, BEC2, small cell lung carcinoma, melanoma (imClone Systems); anti-HLA-Dr10 mAb (1311 LYM-1), Oncoly, Non-Hodgkin's lymphoma (Peregrine Pharmaceuticals); anti-CD33 humanized mAb (SMART M195), Zamyl, acute myeloid leukemia, acute promyelocytic leukemia (Protein Design Labs); anti-CD52 humAb (LDP-03), CAMPATH, chronic lymphocytic leukemia (Millenium Pharmaceuticals/Ilex Oncology); anti-CD1 mAb, ior t6, cancer (Center of Molecular Immunology); anti-CAR (complement activating receptor) mAb, MDX-11, myeloid leukemia (Medarex); humanized bispecific mAb conjugates (complement cascade activators), MDX-22, myeloid leukemia (Medarex); OV 103 (Y-90 labeled antibody), celogovab, OncoScint, ovarian and prostate cancer (Cytogen); anti-17-1A mAb, 3622W94, non-small cell lung carcinoma, prostate cancer (Glaxo Wellcome plc); anti-VEGF (RhumAb-VEGF), bevacizumab, Avastin, lung, breast, prostate, renal and colorectal cancer (Genentech); anti-TAC (IL-2 receptor) humanized Ab (SMART), daclizumab, Zenapax, leukemia, lymphoma (Protein Design Labs); anti-TAG-72 partially humanized bispecific Ab, MDX-220, lung, colon, prostate, ovarian, endometrial, pancreatic and gastric cancer (Medarex); anti-idiotypic mAb mimic of high molecular weight proteoglycan (1-Mel-1), MELIMMUNE-1, melanoma (IDEC); anti-idiotypic mAb mimic of high molecular weight proteoglycan (1-Mel-2), MELIMMUNE-2, melanoma (IDEC); anti-CEA Ab (hMN14), CEACide, colorectal cancer and other cancers (Immunomedics); Pretarget radioactive targeting agents, cancer (NeoRx); hmAbH11 scFv fragment (NovomAb-G2), H11 scFv, cancer (Viventia Biotech); anti-DNA or DNA-associated proteins (histones) mAb and conjugates, TNT (e.g. Cotara), cancer (Peregrine Pharmaceuticals); Gliomab-H mAb, brain cancer, melanoma, neuroblastoma (Viventia Biotech); GNI-250 mAb, colorectal cancer (Wyeth); anti-EGF receptor mAb, EMD-72000, cancer (Merck KgaA); anti-CD22 humanized Ab, LymphoCide, Non-Hodgkin's lymphoma (Immunomedics); anti-CD33 mAb conjugate with calicheamicin (CMA 676), gemtuzumab ozogamicin, Mylotarg, acute myelogenous leukemia (Wyeth); Monopharm-C, colon, lung and pancreatic cancer (Viventia Biotech); anti-idiotypic human mAb to GD2 ganglioside, 4B5, melanoma, small-cell lung cancer, neuroblastoma (Viventia Biotech); anti-EGF receptor humanized Ab, ior egf/r3, cancers of epithelial origin (Center of Molecular Immunology); anti-ior c2 glycoprotein mAb, ior c5, colorectal and ovarian cancer (Center of Molecular Immunology); BABS (biosynthetic antibody binding site) proteins, breast cancer (Chiron); anti-FLK-2/FLT-3 mAb, cancer (tumor-associated angiogenesis) (ImClone Systems); mAb/small-molecule conjugate, TAP (tumor-activated prodrug), cancer (ImmunoGen); anti-GD-2 bispecific mAb, MDX-260, melanoma, glioma, neuroblastoma (Medarex); antinuclear autoantibodies (binds nucleosomes), ANA Ab, cancer (Procyon Biopharma); anti-HLA-DR Ab (SMART 1D10 Ab), Remitogen, Non-Hodgkin's B-cell lymphoma (Protein Design Labs); SMART ABL 364 Ab, epithelial cell cancers, breast, lung and colon cancer (Protein Design Labs/Novartis); anti-CEA I131-labeled mAb, ImmuRAIT-CEA, colorectal cancer (Immunomedics).

Other antibodies that can be used according to the invention include anti-TNFα antibody such as infliximab (Remicade) and etanercept (Enbrel) for rheumatoid arthritis and Crohn's disease palivizumab; anti-RSV antibody for pediatric subjects; bevacizumab, breast cancer; alemtuzumab, Campath-1H, breast and renal cancer, melanoma, B cell chronic lymphocytic leukemia (Millennium and ILEX); BLyS-mAb, fSLE and rheumatoid arthritis; anti-VEGF2, melanoma, breast cancer; anti-Trail receptor; B3 mAb, breast cancer; m 170 mAb, breast cancer; mAB BR96, breast cancer; Abx-Cb1 mAb, graft versus host disease.

The invention embraces a number of classes of antibodies and fragments thereof including but not limited to antibodies directed to cancer antigens (as described above), cell surface molecule, stromal cell molecules, extracellular matrix molecules, and tumor vasculature associated molecules.

A cell surface molecule is a molecule that is expressed at the surface of a cell. In addition to an extracellular domain, it may further comprise a transmembrane domain and a cytoplasinic domain. Examples include HER 2, CD20, CD33, EGF receptor, HLA markers such as HLA-DR, CD52, CD1, CEA, CD22, GD2 ganglioside, FLK2/FLT3, VEGF, VEGFR, and the like.

A stromal cell molecule is a molecule expressed by a stromal cell. Examples include but are not limited to FAP and CD26.

An extracellular matrix molecule is a molecule found in the extracellular matrix.

Examples include but are not limited to collagen, glycosaminoglycans (GAGs), proteoglycans, elastin, fibronectin and laminin.

A tumor vasculature associated molecule is a molecule expressed by vasculature of a tumor (i.e., a solid cancer rather than a systemic cancer such as leukemia). As with a cancer antigen, a tumor vasculature associated molecule may be expressed by normal vasculature however its presence on vasculature of a tumor makes it a suitable target for anticancer therapy. In some instances, the tumor vasculature associated molecule is expressed at a higher level in tumor vasculature than it is in normal vasculature. Examples include but are not limited to endoglin (see U.S. Pat. No. 5,660,827), ELAM-1, VCAM-1, ICAM-1, ligand reactive with LAM-1, MHC class 11 antigens, aminophospholipids such as phosphatidylserine and phosphatidylethanolamine (as described in U.S. Pat. No. 6,312,694), VEGFR1 (FIt-1) and VEGFR2 (KDR/Flk-1), and other tumor vasculature associated antigens such as those described in U.S. Pat. No. 5,776,427.

Antibodies to endoglin are described in U.S. Pat. No. 5,660,827 and include TEC-4 and TEC-11, and antibodies that recognize identical epitopes to these antibodies. Antibodies to aminophospholipids are described in U.S. Pat. No. 6,312,694. Antibodies that inhibit VEGF are described in U.S. Pat. No. 6,342,219 and include 2C3 (ATCC PTA 1595). Other antibodies that are specific for tumor vasculature include antibodies that react to a complex of a growth factor and its receptor such as a complex of FGF and the FGFR or a complex of TGFβ and the TGFβR. Antibodies of this latter class are described in U.S. Pat. No. 5,965,132, and include GV39 and GV97.

It is to be understood that the antibodies embraced by the invention include those recited explicitly herein and also those that bind to the same epitope as those recited herein. Also useful in the invention are antibodies such as the following, all of which are commercially available:

Apoptosis antibodies;

BAX Antibodies: Anti-Human Bax Antibodies (Monoclonal), Anti-Human Bax Antibodies (Polyclonal), Anti-Murine Bax Antibodies (Monoclonal), Anti-Murine Bax Antibodies (Polyclonal);

Fas/Fas Ligand Antibodies: Anti-Human Fas/Fas Ligand Antibodies, Anti-Murine Fas/Fas Ligand Antibodies Granzyme Antibodies Granzyme B Antibodies;

BCL Antibodies: Anti Cytochrome C Antibodies, Anti-Human BCL Antibodies (Monoclonal), Anti-Human bcl Antibodies (Polyclonal), Anti-Murine bcl Antibodies (Monoclonal), Anti-Murine bcl Antibodies (Polyclonal);

Miscellaneous Apoptosis Antibodies: Anti TRADD, TRAIL, TRAFF, DR3 Antibodies Anti-Human Fas/Fas Ligand Antibodies Anti-Murine Fas/Fas Ligand Antibodies;

Miscellaneous Apoptosis Related Antibodies: BIM Antibodies: Anti Human, Murine bim Antibodies (Polyclonal), Anti-Human, Murine bim Antibodies (Monoclonal);

PARP Antibodies: Anti-Human PARP Antibodies (Monoclonal), Anti-Human PARP Antibodies (Polyclonal) Anti-Murine PARP Antibodies;

Caspase Antibodies: Anti-Human Caspase Antibodies (Monoclonal), Anti-Murine Caspase Antibodies;

Anti-CD Antibodies: Anti-CD29, PL18-5 PanVera, Anti-CD29, PL4-3 PanVera, Anti-CD41a, PT25-2 PanVera, Anti-CD42b, PL52-4 PanVera, Anti-CD42b, GUR20-5 PanVera, Anti-CD42b, WGA-3 PanVeraAnti-CD43, 1D4 PanVera, Anti-CD46, MCP75-6 PanVera, Anti-CD61, PL 11-7 PanVera, Anti-CD61, PL8-5 PanVera, Anti-CD62/P-slctn, PL7-6 PanVera, Anti-CD62/P-slctn, WGA-1 PanVera, Anti-CD154, SF3 PanVera; and anti-CD1, anti-CD2, anti-CD3, anti-CD4, anti-CD5, anti-CD6, anti-CD7, anti-CD8, anti-CD9, anti-CD 10, anti-CD 11, anti-C D12, anti-CD 13, anti-CD14, anti-CD15, anti-CD16, anti-CD17, anti-CD18, anti-CD19, anti-CD20, anti-CD21, anti-CD22, anti-CD23, anti-CD24, anti-CD25, anti-CD26, anti-CD27, anti-CD28, anti-CD29, anti-CD30, anti-CD31, anti-CD32, anti-CD33, anti-CD34, anti-CD35, anti-CD36, anti-CD37, anti-CD38, anti-CD39, anti-CD40 anti-CD41, anti-CD42, anti-CD43, anti-CD44, anti-CD45, anti-CD46, anti-CD47, anti-CD48, anti-CD49, anti-CD50, anti-CD51, anti-CD52, anti-CD53, anti-CD54, anti-CD55, anti-CD56, anti-CD57, anti-CD58, anti-CD59, anti-CD60, anti-CD61, anti-CD62, anti-CD63, anti-CD64, anti-CD65, anti-CD66, anti-CD67, anti-CD68, anti-CD69, anti-CD70, anti-CD71, anti-CD72, anti-CD73, anti-CD74, anti-CD75, anti-CD76, anti-CD77, anti-CD78, anti-CD79, anti-CD80, anti-CD81, anti-CD82, anti-CD83, anti-CD84, anti-CD85, anti-CD86, anti-CD87, anti-CD88, anti-CD89, anti-CD90, anti-CD91, anti-CD92, anti-CD93, anti-CD94, anti-CD95, anti-CD96, anti-CD97, anti-CD98, anti-CD99, anti- CD100, anti-CD101, anti-CD102, anti-CD103, anti-CD104, anti-CD105, anti-CD106, anti-CD 107, anti-CD 108, anti-CD 109, anti-CD 110, anti-CD111, anti-CD 112, anti-CD 113, anti-CD114, anti-CD115, anti-CD116, anti-CD117, anti-CD118, anti-CD119, anti-CD120, anti-CD121, anti-CD122, anti-CD123, anti-CD124, anti-CD125, anti-CD126, anti-CD127, anti-CD128, anti-CD129, anti-CD130, anti-CD131, anti-CD132, anti-CD133, anti-CD134, anti-CD135, anti-CD136, anti-CD137, anti-CD138, anti-CD139, anti-CD140, anti-CD141, anti-CD142, anti-CD143, anti-CD144, anti-CD145, anti-CD146, anti-CD147, anti-CD148, anti-CD149, anti-CD150, anti-CD151, anti-CD152, anti-CD153, anti-CD154, anti-CD155, anti-CD156, anti-CD157, anti-CD158, anti-CD159, anti-CD160, anti-CD161, anti-CD162, anti-CD163, anti-CD164, anti-CD165, anti-CD166, anti-CD167, anti-CD168, anti-CD169, anti-CD170, anti-CD171, anti-CD172, anti-CD173, anti-CD174, anti-CD175, anti-CD176, anti-CD177, anti-CD178, anti-CD179, anti-CD180, anti-CD181, anti-CD182, anti-CD183, anti-CD184, anti-CD185, anti-CD186, anti-CD187, anti-CD188, anti-CD189, anti-CD190, anti-CD191, anti-CD192, anti-CD193, anti-CD194, anti-CD195, anti-CD196, anti-CD197, anti-CD198, anti-CD199, anti-CD200, anti-CD201, anti-CD202, anti-CD203, anti-CD204, anti-CD205, anti-CD206, anti-CD207, anti-CD208, anti-CD209, anti-CD210, anti-CD211, anti-CD212, anti-CD213, anti-CD214, anti-CD215, anti-CD216, anti-CD217, anti-CD218, anti-CD219, anti-CD220, anti-CD221, anti-CD222, anti-CD223, anti-CD224, anti-CD225, anti-CD226, anti-CD227, anti-CD228, anti-CD229, anti-CD230, anti-CD231, anti-CD232, anti-CD233, anti-CD234, anti-CD235, anti-CD236, anti-CD237, anti-CD238, anti-CD239, anti-CD240 anti-CD241, anti-CD242, anti-CD243, anti-CD244, anti-CD245, anti-CD246, anti-CD247, anti-CD248, anti-CD249, anti-CD250, and the like;

Human Chemokine Antibodies: Human CNTF Antibodies, Human Eotaxin Antibodies, Human Epitherlial Neutrophil Activating Peptide-78, Human Exodus Antibodies, Human GRO Antibodies, Human HCC-1 Antibodies, Human 1-309 Antibodies, Human IP-10 Antibodies, Human 1-TAC Antibodies, Human LIF Antibodies, Human Liver-Expressed Chemokine Antibodies, Human lymphotoxin Antibodies, Human MCP Antibodies, Human MIP Antibodies, Human Monokine Induced by IFN-gamma Antibodies, Human NAP-2 Antibodies, Human NP-1 Antibodies, Human Platelet Factor-4 Antibodies, Human RANTES Antibodies, Human SDF Antibodies, Human TECK Antibodies;

Murine Chemokine Antibodies: Human B-Cell Attracting Murine Chemokine Antibodies, Chemokine-1 Antibodies, Murine Eotaxin Antibodies, Murine Exodus Antibodies, Murine GCP-2 Antibodies, Murine KC Antibodies, Murine MCP Antibodies, Murine MIP Antibodies, Murine RANTES Antibodies, Rat Chemokine Antibodies, Rat Chemokine Antibodies, Rat CNTF Antibodies, Rat GRO Antibodies, Rat MCP Antibodies, Rat MIP Antibodies, Rat RANTES Antibodies;

Cytokine/Cytokine Receptor Antibodies: Human Biotinylated Cytokine/Cytokine Receptor Antibodies, Human IFN Antibodies, Human IL Antibodies, Human Leptin Antibodies, Human Oncostatin Antibodies, Human TNF Antibodies, Human TNF Receptor Family Antibodies, Murine Biotinylated Cytokine/Cytokine Receptor Antibodies, Murine IFN Antibodies, Murine IL Antibodies, Murine TNF Antibodies, Murine TNF Receptor Antibodies; anti-CCR4 antibody;

Rat Cytokine/Cytokine Receptor Antibodies: Rat Biotinylated Cytokine/Cytokine Receptor Antibodies, Rat IFN Antibodies, Rat IL Antibodies, Rat TNF Antibodies;

ECM Antibodies: Collagen/Procollagen, Laminin, Collagen (Human), Laminin (Human), Procollagen (Human), Vitronectin/Vitronectin Receptor, Vitronectin (Human), Vitronectin Receptor (Human), Fibronectin/Fibronectin Receptor, Fibronectin (Human), Fibronectin Receptor (Human);

Growth Factor Antibodies: Human Growth Factor Antibodies, Murine Growth Factor Antibodies, Porcine Growth Factor Antibodies;

Miscellaneous Antibodies: Baculovirus Antibodies, Cadherin Antibodies, Complement Antibodies, C1q Antibodies, Von Willebrand Factor Antibodies, Cre Antibodies, HIV Antibodies, Influenza Antibodies, Human Leptin Antibodies, Murine Leptin Antibodies, Murine CTLA-4 Antibodies, Human CTLA-4 Antibodies, P450 Antibodies, RNA Polymerase Antibodies;

Neurobio Antibodies: Amyloid Antibodies, GFAP Antibodies, Human NGF Antibodies, Human NT-3 Antibodies, Human NT-4 Antibodies.

Still other antibodies can be used in the invention and these include antibodies listed in references such as the MSRS Catalog of Primary Antibodies, and Linscott's Directory;

In some preferred embodiments of the invention, the antibodies are Avastin (bevacizumab), BEC2 (mitumomab), Bexxar (tositumomab), Campath (alemtuzumab), CeaVac, Herceptin (trastuzumab), IMC-C225 (centuximab), LymphoCide (epratuzumab), MDX-210, Mylotarg (gemtuzumab ozogamicin), Panorex (edrecolomab), Rituxan (rituximab), Theragyn (pemtumomab), Zamyl, and Zevalin (ibritumomab tituxetan). The invention also covers antibody fragments thereof.

In some preferred embodiments, the cancer antigen is VEGF, Anti-idiotypic mAb (GD3 ganglioside mimic), CD20, CD52, Anti-idiotypic mAb (CEA mimic), ERBB2, EGFR, CD22, ERBB2 X CD65 (fc.gamma.RI), EpCam, PEM and CD33.

The invention encompasses the use of both antibodies and antibody fragments. The antibodies may be monoclonal or polyclonal, and can be prepared by conventional methodology. They may further be isolated or present in an ascites fluid. Such antibodies can be further manipulated to create chimeric or humanized antibodies as will be discussed in greater detail below.

Significantly, as is well-known in the art, only a small portion of an antibody molecule, the paratope, is involved in the binding of the antibody to its epitope (see, in general, Clark, W. R. (1986) The Experimental Foundations of Modern Immunology Wiley & Sons, Inc., New York; Roitt, 1. (1991) Essential Immunology, 7th Ed., Blackwell Scientific Publications, Oxford). The pFc' and Fc regions, for example, are effectors of the complement cascade but are not involved in antigen binding. An antibody from which the pFc' region has been enzymatically cleaved, or which has been produced without the pFc' region, designated an F(ab').sub.2 fragment, retains both of the antigen binding sites of an intact antibody. Similarly, an antibody from which the Fc region has been enzymatically cleaved, or which has been produced without the Fc region, designated an Fab fragment, retains one of the antigen binding sites of an intact antibody molecule. Proceeding further, Fab fragments consist of a covalently bound antibody light chain and a portion of the antibody heavy chain denoted Fd. The Fd fragments are the major determinant of antibody specificity (a single Fd fragment may be associated with up to ten different light chains without altering antibody specificity) and Fd fragments retain epitope-binding ability in isolation.

Within the antigen-binding portion of an antibody, as is well-known in the art, there are complementarity determining regions (CDRs), which directly interact with the epitope of the antigen, and framework regions (FRs), which maintain the tertiary structure of the paratope (see, in general, Clark, 1986; Roitt, 1991). In both the heavy chain Fd fragment and the light chain of IgG immunoglobulins, there are four framework regions (FR1 through FR4) separated respectively by three complementarity determining regions (CDR1 through CDR3). The CDRs, and in particular the CDR3 regions, and more particularly the heavy chain CDR3, are largely responsible for antibody specificity.

It is now well-established in the art that the non-CDR regions of a mammalian antibody may be replaced with similar regions of co-specific or heterospecific antibodies while retaining the epitopic specificity of the original antibody. This is most clearly manifested in the development and use of "humanized" antibodies in which non-human CDRs are covalently joined to human FR and/or Fc/pFc' regions to produce a functional antibody. Thus, for example, PCT International Publication Number WO 92/04381 teaches the production and use of humanized murine RSV antibodies in which at least a portion of the murine FR regions has been replaced by FR regions of human origin. Such antibodies, including fragments of intact antibodies with antigen-binding ability, are often referred to as "chimeric" antibodies. Commercial sources of humanized or chimeric antibodies include GenPharm, Xenotech, AbGenix and CeliGeneSys.

Thus, as will be apparent to one of ordinary skill in the art, the present invention also provides for F(ab')$_2$, Fab, Fv and Fd fragments; chimeric antibodies in which the Fc and/or FR and/or CDR1 and/or CDR2 and/or light chain CDR3 regions have been replaced by homologous human or non-human sequences; chimeric F(ab')$_2$ fragment antibodies in which the FR and/or CDR1 and/or CDR2 and/or light chain CDR3 regions have been replaced by homologous human or non-human sequences; chimeric Fab fragment antibodies in which the FR and/or CDR1 and/or CDR2 and/or light chain CDR3 regions have been replaced by homologous human or non-human sequences; and chimeric Fd fragment antibodies in which the FR and/or CDR1 and/or CDR2 regions have been replaced by homologous human or non-human sequences. The present invention also includes so-called single chain antibodies.

In some embodiments, administration of an agent comprising JFPB, JFPH, and/or functional equivalents and an antibody or fragment thereof such as an anti-cancer antibody or antibody fragment, or an anti-microbial antibody or antibody fragment, has a benefit over the administration of either agent alone. In some embodiments, the effect is additive, and in others it is synergistic.

Thus, in one aspect of the invention, an agent comprising JFPB, JFPH, and/or functional equivalents and the anti-cancer antibody or fragment thereof are administered as a synergistic combination in an effective amount to treat or reduce the risk of developing a cancer. As used herein, the term "synergistic" describes an effect resulting from the combination of at least two agents which is greater than the effect of each of the individual agents when used alone. When used together either or both agents may be used at lower doses than would be used if either agent was administered alone. In these embodiments, either agent or both may be administered in a "sub-therapeutic" dose for each alone, the combination, however, being therapeutic.

Treatment after a disorder has started aims to reduce, ameliorate or altogether eliminate the disorder, and/or its associated symptoms, or prevent it from becoming worse. Treatment of subjects before a disorder has started (i.e., prophylactic treatment) aims to reduce the risk of developing the disorder. As used herein, the term "prevent" refers to the prophylactic treatment of patients who are at risk of developing a disorder (resulting in a decrease in the probability that the subject will develop the disorder), and to the inhibition of further development of an already established disorder.

The antibodies provided herein can be used additionally for delivery of toxic substances to cancer cells. Antibodies are commonly conjugated to toxins such as ricin (e.g., from castor beans), calicheamicin and maytansinoids, to radioactive isotopes such as Iodine-131 and Yttrium-90, to chemotherapeutic agents, or to biological response modifiers. In this way, the toxic substances can be concentrated in the region of the cancer and non-specific toxicity to normal cells can be minimized. In addition to the use of antibodies which are specific for cancer antigens, antibodies which bind to vasculature, such as those which bind to endothelial cells, are also useful in the invention. This is because, generally, solid tumors are dependent upon newly formed blood vessels to survive, and thus most tumors are capable of recruiting and stimulating the growth of new blood vessels. As a result, one strategy of many cancer medicaments is to attack the blood vessels feeding a tumor and/or the connective tissues (or stroma) supporting such blood vessels.

The compositions comprising JFPB, JFPH, and/or functional equivalents of the invention can further include chemotherapeutic agents such as but not limited to those currently in use with the antibodies recited herein. Several chemotherapeutic agents can be categorized as DNA damaging agents and these include topoisomerase inhibitors (e.g., etoposide, ramptothecin, topotecan, teniposide, mitoxantrone), anti-microtubule agents (e.g., vincristine, vinblastine), anti-metabolic agents (e.g., cytarabine, methotrexate, hydroxyurea, 5-fluorouracil, floxuridine, 6-thioguanine, 6-mercaptopurine, fludarabine, pentostatin, chlorodeoxyadenosine), DNA alkylating agents (e.g., cisplatin, mechlorethamine, cyclophosphamide, ifosfamide, melphalan, chorambucil, busulfan, thiotepa, carmustine, lomustine, carboplatin, dacarbazine, procarbazine), DNA strand break inducing agents (e.g., bleomycin, doxorubicin, daunorubicin, idarubicin, mitomycin C), and radiation therapy.

Important anticancer agents are those selected from the group consisting of: Acivicin; Aclarubicin; Acodazole Hydrochloride; Acronine; Adozelesin; Adriamycin; Aldesleukin; Alitretinoin; Allopurinol Sodium; Altretamine; Ambomycin; Ametantrone Acetate; Aminoglutethimide; Amsacrine; Anastrozole; Annonaceous Acetogenins; Anthramycin; Asimicin; Asparaginase; Asperlin; Azacitidine; Azetepa; Azotomycin; Batimastat; Benzodepa; Bexarotene; Bicalutamide; Bisantrene Hydrochloride; Bisnafide Dimesylate; Bizelesin; Bleomycin Sulfate; Brequinar Sodium; Bropirimine; Bullatacin; Busulfan; Cabergoline; Cactinomycin; Calusterone; Caracemide; Carbetimer; Carboplatin; Carmustine; Carubicin Hydrochloride; Carzelesin; Cedefingol; Celecoxib; Chlorambucil; Cirolemycin; Cisplatin; Cladribine; Crisnatol Mesylate; Cyclophosphamide; Cytarabine; Dacarbazine; DACA (N-[2-(Dimethyl-amino)ethyl]acridine-4-carboxamide); Dactinomycin; Daunorubicin Hydrochloride; Daunomycin; Decitabine; Denileukin Diftitox; Dexormaplatin; Dezaguanine; Dezaguanine Mesylate; Diaziquone; Docetaxel; Doxorubicin; Doxorubicin Hydrochloride; Droloxifene; Droloxifene Citrate; Dromostanolone Propionate; Duazomycin; Edatrexate; Eflornithine Hydrochloride; Elsamitrucin; Enloplatin; Enpromate; Epipropidine; Epirubicin Hydrochloride; Erbulozole; Esorubicin Hydrochloride; Estramustine; Estramustine Phosphate Sodium; Etanidazole; Ethiodized Oil I 131; Etoposide; Etoposide Phosphate; Etoprine; Fadrozole Hydrochloride; Fazarabine; Fenretinide; Floxuridine; Fludarabine Phosphate; Fluorouracil; 5-FdUMP; Flurocitabine; Fosquidone; Fostriecin Sodium; FK-317; FK-973; FR-66979; FR-900482; Gemcitabine; Geimcitabine Hydrochloride; Gemtuzumab Ozogamicin; Gold Au 198; Goserelin Acetate; Guanacone; Hydroxyurea; Idarubicin Hydrochloride; Ifosfamide; Ilmofosine; Interferon Alfa-2a; Interferon Alfa-2b; Interferon Alfa-n1; Interferon Alfa-n3; Interferon Beta-1a; Interferon Gamma-1b; Iproplatin; Irinotecan Hydrochloride; Lanreotide Acetate; Letrozole; Leuprolide Acetate; Liarozole Hydrochloride; Lometrexol Sodium; Lomustine; Losoxantrone Hydrochloride; Masoprocol; Maytansine; Mechlorethamine Hydrochloride; Megestrol Acetate; Melengestrol Acetate; Melphalan; Menogaril; Mercaptopurine; Methotrexate; Methotrexate Sodium; Methoxsalen; Metoprine; Meturedepa; Mitindomide; Mitocarcin; Mitocromin; Mitogillin; Mitomalcin; Mitomycin; Mytomycin C; Mitosper; Mitotane; Mitoxantrone Hydrochloride; Mycophenolic Acid; Nocodazole; Nogalamycin; Oprelvekin; Ormaplatin; Oxisuran; Paclitaxel; Pamidronate Disodium; Pegaspargase; Peliomycin; Pentamustine; Peplomycin Sulfate; Perfosfamide; Pipobroman; Piposulfan; Piroxantrone Hydrochloride; Plicamycin; Plomestane; Porfimer Sodium; Porfiromycin; Prednimustine; Procarbazine Hydrochloride; Puromycin; Puromycin Hydrochloride; Pyrazofurin; Riboprine; Rituximab; Rogletimide; Rolliniastatin; Safingol; Safingol Hydrochloride; Samarium/Lexidronam; Semustine; Simtrazene; Sparfosate Sodium; Sparsomycin; Spirogermanium Hydrochloride; Spiromustine; Spiroplatin; Squamocin; Squamotacin; Streptonigrin; Streptozocin; Strontium Chloride Sr 89; Sulofenur; Talisomycin; Taxane; Taxoid; Tecogalan Sodium; Tegafur; Teloxantrone Hydrochloride; Temoporfin; Teniposide; Teroxirone; Testolactone; Thiamiprine; Thioguanine; Thiotepa; Thymitaq; Tiazofurin; Tirapazamine; Tomudex; TOP-53; Topotecan Hydrochloride; Toremifene Citrate; Trastuzumab; Trestolone Acetate; Triciribine Phosphate; Trimetrexate; Trimetrexate Glucuronate; Triptorelin; Tubulozole Hydrochloride; Uracil Mustard; Uredepa; Valrubicin; Vapreotide; Verteporfin; Vinblastine; Vinblastine Sulfate; Vincristine; Vincristine Sulfate; Vindesine; Vindesine Sulfate; Vinepidine Sulfate; Vinglycinate Sulfate; Vinleurosine Sulfate; Vinorelbine Tartrate; Vinrosidine Sulfate; Vinzolidine Sulfate; Vorozole; Zeniplatin; Zinostatin; Zorubicin Hydrochloride; 2-Chlorodeoxyadenosine; 2'-Deoxyformycin; 9-aminocamptothecin; raltitrexed; N-propargyl-5,8-dideazafolic acid; 2-chloro-2'-arabino-fluoro-2'-deoxyadenosine; 2-chloro-2'-deoxyadenosine; anisomycin; trichostatin A; hPRL-G129R; CEP-751; linomide; sulfur mustard; nitrogen mustard (mechlorethamine); cyclophosphamide; melphalan; chlorambucil; ifosfamide; busulfan; N-methyl-N-nitrosourea (MNU); N,N'-Bis(2-chloroethyl)-N-nitrosourea (BCNU); N-(2-chloroethyl)-N'-cyclohex-yl-N-nitrosourea (CCNU); N-(2-chloroethyl)-N'-(trans-4-methylcyclohexyl-N-nitrosourea (MeCCNU); N-(2-chloroethyl)-N'-(diethyl)ethylphosphonate-N-nit-rosourea (fotemustine); streptozotocin; diacarbazine (DTIC); mitozolomide; temozolomide; thiotepa; mitomycin C; AZQ; adozelesin; Cisplatin; Carboplatin; Ormaplatin; Oxaliplatin; C1-973; DWA 2114R; JM216; JM335; Bis (platinum); tomudex; azacitidine; cytarabine; gemcitabine; 6-Mercaptopurine; 6-Thioguanine; Hypoxanthine; teniposide; 9-amino camptothecin; Topotecan; CPT-11; Doxorubicin; Daunomycin; Epirubicin; darubicin; mitoxantrone; losoxantrone; Dactinomycin (Actinomycin D); amsacrine; pyrazoloacridine; all-trans retinol; 14-hydroxy-retro-retinol; all-trans retinoic acid; N-(4-Hydroxyphenyl) retinamide; 13-cis retinoic acid; 3-Methyl TTNEB; 9-cis retinoic acid; fludarabine (2-F-ara-AMP); and 2-chlorodeoxyadenosine (2-Cda).

Other anti-neoplastic compounds include: 20-epi-1,25 dihydroxyvitamnin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bleomycin $A_2$; bleomycin $B_2$; bropirimine; budotitane; buthionine sulfoximine; calcipotriol; calphostin C; camptothecin derivatives (e.g., 10-hydroxy-camptothecin); canarypox IL-2; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; 2' deoxycoformycin (DCF); deslorelin; dexifosfamide; dexrazoxane; dexverapamil; diaziquone; didemnin B; didox; diethylnorspermine; dihydro-5-azacytidine; dihydrotaxol, 9-; dioxamycin; diphenyl spiromustine; discodermolide; docosanol; dolasetron; doxifluridine; droloxifene; dronabinol; duocarmycin SA; ebselen; ecomustine; edelfosine; edrecolomab; eflornithine; elemene; emitefur; epirubicin; epothilones (A, R=H; B, R=Me); epithilones; epristeride; estramustine analogue; estrogen agonists; estrogen antagonists; etanidazole; etoposide; etoposide 4'-phosphate (etopofos); exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; homoharringtonine (HHT); hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; ipomeanol, 4-; irinotecan; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptoistatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix met alloproteinase inhibitors; menogaril; merbarone; meterelin; methioninase; metoclopramide; MIF inhibitor; mifepristone; miltefosine; mirimostim; mismatched double stranded RNA; mithracin; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; O6-benzylguanine; octreotide; okicenone; oligonucleotides; onapristone; ondansetron; ondansetron; oracin; oral cytokine inducer; ormaplatin; osaterone; oxaliplatin; oxaunomycin; paclitaxel analogues; paclitaxel derivatives; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; podophyllotoxin; porfimer sodium; porfiromycin; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rogletimide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen binding protein; sizofuran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosanninoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thalidomide; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene dichloride; topotecan; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; zinostatin, and stimalamer.

Other anti-cancer agents include: Antiproliferative agents (e.g., Piritrexim Isothionate), Antiprostatic hypertrophy agent (e.g., Sitogluside), Benign prostatic hyperplasia therapy agents (e.g., Tamsulosin Hydrochloride), Prostate growth inhibitor agents (e.g., Pentomone), and Radioactive agents: Fibrinogen 1 125; Fludeoxyglucose F 18; Fluorodopa F 18; Insulin I 125; Insulin I 131; Iobenguane I 123; Iodipamide Sodium I 131; Iodoantipyrine I 131; Iodocholesterol I 131; Iodohippurate Sodium I 123; Iodohippurate Sodium I 125; Iodohippurate Sodium I 131; Iodopyracet I 125; Iodopyracet I 131; Iofetamine Hydrochloride I 123; Iomethin I 125; Iomethin I 131; Iothalamate Sodium I 125; Iothalamate Sodium I 131; Iotyrosine I 131; Liothyronine I 125; Liothyronine I 131; Merisoprol Acetate Hg 197; Merisoprol Acetate Hg 203; Merisoprol Hg 197; Selenomethionine Se 75; Technetium Tc 99m Antimony Trisulfide Colloid; Technetium Tc 99m Bicisate; Technetium Tc 99m Disofenin; Technetium Tc 99m Etidronate; Technetium Tc 99m Exametazime; Technetium Tc 99m Furifosmin; Technetium Tc 99m Gluceptate; Technetium Tc 99m Lidofenin; Technetium Tc 99m Mebrofenin; Technetium Tc 99m Medronate; Technetium Tc 99m Medronate Disodium; Technetium Tc 99m Mertiatide; Technetium Tc 99m Oxidronate; Technetium Tc 99m Pentetate; Technetium Tc 99m Pentetate Calcium Trisodium; Technetium Tc 99m Sestamibi; Technetium Tc 99m Siboroxime; Technetium Tc 99m Succimer; Technetium Tc 99m Sulfur Colloid; Technetium Tc 99m Teboroxime; Technetium Tc 99m Tetrofosmin; Technetium Tc 99m Tiatide; Thyroxine I 125; Thyroxine I 131; Tolpovidone I 131; Triolein I 125; Triolein I 131.

Another category of anti-cancer agents is anti-cancer Supplementary Potentiating Agents, including: Tricyclic anti-depressant drugs (e.g., imipramine, desipramine, amitryptyline, clomipramine, trimipramine, doxepin, nortriptyline, protriptyline, amoxapine and maprotiline); non-tricyclic anti-depressant drugs (e.g., sertraline, trazodone and citalopram); $Ca^{++}$ antagonists (e.g., verapamil, nifedipine, nitrendipine and caroverine); Calmodulin inhibitors (e.g., prenylamine, trifluoroperazine and clomipramine); Amphotericin B; Triparanol analogues (e.g., tamoxifen); antiarrhythmic drugs (e.g., quinidine); antihypertensive drugs (e.g., reserpine); Thiol depleters (e.g., buthionine and sulfoximine) and Multiple Drug Resistance reducing agents such as Cremaphor EL.

Particularly important anticancer agents are those selected from the group consisting of: annonaceous acetogenins; asimicin; rolliniastatin; guanacone, squamocin, bullatacin; squamotacin; taxanes; paclitaxel; gemcitabine; methotrexate FR-900482; FK-973; FR-66979; FK-317; 5-FU; FUDR; FdUMP; Hydroxyurea; Docetaxel; discodermolide; epothilones; vincristine; vinblastine; vinorelbine; meta-pac; irinotecan; SN-38; 10-OH campto; topotecan; etoposide; adriamycin; flavopiridol; Cis-Pt; carbo-Pt; bleomycin; mitomycin C; mithramycin; capecitabine; cytarabine; 2-C1-2'deoxyadenosine; Fludarabine-PO.sub.4; mitoxantrone; mitozolomide; Pentostatin; Tomudex.

One particularly preferred class of anticancer agents are taxanes (e.g., paclitaxel and docetaxel) are preferred. Another important category of anticancer agent is annonaceous acetogenin.

In some embodiments, an agent comprising JFPB, JFPH, and/or functional equivalent are administered together with anti-cancer compounds selected from the group consisting of aldesleukin, asparaginase, bleomycin sulfate, carboplatin, chlorambucil, cisplatin, cladribine, cyclophosphamide, cytarabine, dacarbazine, dactinomycin, daunorubicin hydrochloride, docetaxel, doxorubicin, doxorubicin hydrochloride, epirubicin hydrochloride, etoposide, etoposide phosphate, floxuridine, fludarabine, fluorouracil, gemcitabine, gemcitabine hydrochloride, hydroxyurea, idarubicin hydrochloride, ifosfamide, interferons, interferon-α2a, interferon-α2b, interferon- αn3, interferon-α1b, interleukins, irinotecan, mechlorethamine hydrochloride, melphalan, mercatopurine, methotrexate, methotrexate sodium, mitomycin, mitoxantrone, paclitaxel, pegaspargase, pentostatin, prednisone, profimer sodium, procabazine hydrochloride, taxol, taxotere, teniposide, topotecan hydrochloride, vinblastine sulfate, vincristine sulfate and vinorelbine tartrate.

Other cancer therapies include hormonal manipulation, particularly for breast and gynecological cancers. In some embodiments, an agent comprising JFPB, JFPH, and/or functional equivalent is used in combination with tamoxifen or aromatase inhibitor arimidex (i.e., anastrozole), or simply for disorders responsive to either (e.g., breast cancer).

In some embodiments, an agent comprising JFPB, JFPH, and/or functional equivalent can also be combined, and/or administered substantially simultaneously, with enzyme inhibitor agents such as CDK inhibitors, tyrosine kinase inhibitors, MAP kinase inhibitors, and EGFR inhibitors (e.g., C225).

In some embodiments, the combination therapy is administered to subjects having or at risk of developing cancer. A subject having a cancer is a subject that has detectable cancerous cells. A subject at risk of developing a cancer is one who has a higher than normal probability of developing cancer. These subjects include, for instance, subjects having a genetic abnormality that has been demonstrated to be associated with a higher likelihood of developing a cancer, subjects having a familial disposition to cancer, subjects exposed to cancer causing agents (i.e., carcinogens) such as tobacco, asbestos, or other chemical toxins, and subjects previously treated for cancer and in apparent remission.

"Cancer" as used herein refers to an uncontrolled growth of cells which interferes with the normal functioning of the bodily organs and systems. Cancers which migrate from their original location and seed vital organs can eventually lead to the death of the subject through the functional deterioration of the affected organs. Hemopoietic cancers, such as leukemia, are able to outcompete the normal hemopoietic compartments in a subject, thereby leading to hemopoietic failure (in the form of anemia, thrombocytopenia and neutropenia) ultimately causing death.

A metastasis is a region of cancer cells, distinct from the primary tumor location resulting from the dissemination of cancer cells from the primary tumor to other parts of the body. At the time of diagnosis of the primary tumor mass, the subject may be monitored for the presence of metastases. Metastases are most often detected through the sole or combined use of magnetic resonance imaging (MRI) scans, computed tomography (CT) scans, blood and platelet counts, liver function studies, chest X-rays and bone scans in addition to the monitoring of specific symptoms.

A cancer cell is a cell that divides and reproduces abnormally due to a loss of normal growth control. Cancer cells almost always arise from at least one genetic mutation. In some instances, it is possible to distinguish cancer cells from their normal counterparts based on profiles of expressed genes and proteins, as well as to the level of their expression. Genes commonly affected in cancer cells include oncogenes, such as ras, neu/HER2/erbB, myb, myc and abl, as well as tumor suppressor genes such as p53, Rb, DCC, RET and WT. Cancer-related mutations in some of these genes leads to a decrease in their expression or a complete deletion. In others, mutations cause an increase in expression or the expression of an activated variant of the normal counterpart.

The term "tumor" is usually equated with neoplasm, which literally means "new growth" and is used interchangeably with "cancer." A "neoplastic disorder" is any disorder associated with cell proliferation, specifically with a neoplasm. A "neoplasm" is an abnormal mass of tissue that persists and proliferates after withdrawal of the carcinogenic factor that initiated its appearance. There are two types of neoplasms, benign and malignant. Nearly all benign tumors are encapsulated and are noninvasive; in contrast, malignant tumors are almost never encapsulated but invade adjacent tissue by infiltrative destructive growth. This infiltrative growth can be followed by tumor cells implanting at sites discontinuous with the original tumor. The method of the invention can be used to treat neoplastic disorders in humans, including but not limited to: sarcoma, carcinoma, fibroma, leukemia, lymphoma, melanoma, myeloma, neuroblastoma, rhabdomyosarcoma, retinoblastoma, and glioma as well as each of the other tumors described herein.

Cancers include, but are not limited to, basal cell carcinoma, biliary tract cancer; bladder cancer; bone cancer; brain and CNS cancer; breast cancer; cervical cancer; choriocarcinoma; colon and rectum cancer; connective tissue cancer; cancer of the digestive system; endometrial cancer; esophageal cancer; eye cancer; cancer of the head and neck; gastric cancer; intra-epithelial neoplasm; kidney cancer; larynx cancer; leukemia including acute myeloid leukemia, acute lymphoid leukemia, chronic myeloid leukemia, chronic lymphoid leukemia; liver cancer; lung cancer (e.g. small cell and non-small cell); lymphoma including Hodgkin's and Non-Hodgkin's lymphoma; melanoma; myeloma; neuroblastoma; oral cavity cancer (e.g., lip, tongue, mouth, and pharynx); ovarian cancer; pancreatic cancer; prostate cancer; retinoblastoma; rhabdomyosarcoma; rectal cancer; renal cancer; cancer of the respiratory system; sarcoma; skin cancer; stomach cancer; testicular cancer; thyroid cancer; uterine cancer; cancer of the urinary system, as well as other carcinomas and sarcomas.

Carcinomas are cancers of epithelial origin. Carcinomas intended for treatment with the methods of the invention include, but are not limited to, acinar carcinoma, acinous carcinoma, alveolar adenocarcinoma (also called adenocystic carcinoma, adenomyoepithelioina, cribriform carcinoma and cylindroma), carcinoma adenomatosum, adenocarcinoma, carcinoma of adrenal cortex, alveolar carcinoma, alveolar cell carcinoma (also called bronchiolar carcinoma, alveolar cell tumor and pulmonary adenomatosis), basal cell carcinoma, carcinoma basocellulare (also called basaloma, or basiloma, and hair matrix carcinoma), basaloid carcinoma, basosquamous cell carcinoma, breast carcinoma, bronchioalveolar carcinoma, bronchiolar carcinoma, bronchogenic carcinoma, cerebriform carcinoma, cholangiocellular carcinoma (also called cholangioma and cholangiocarcinoma), chorionic carcinoma, colloid carcinoma, comedo carcinoma, corpus carcinoma, cribriform carcinoma, carcinoma en cuirasse, carcinoma cutaneum, cylindrical carcinoma, cylindrical cell carcinoma, duct carcinoma, carcinoma durum, embryonal carcinoma, encephaloid carcinoma, epibulbar carcinoma, epidermoid carcinoma, carcinoma epitheliale adenoides, carcinoma exulcere, carcinoma fibrosum, gelatiniform carcinoma, gelatinous carcinoma, giant cell carcinoma, gigantocellulare, glandular carcinoma, granulosa cell carcinoma, hair-matrix carcinoma, hematoid carcinoma, hepatocellular carcinoma (also called hepatoma, malignant hepatoma and hepatocarcinoma), Huirthle cell carcinoma, hyaline carcinoma, hypernephroid carcinoma, infantile embryonal carcinoma, carcinoma in situ, intraepidermal carcinoma, intraepithelial carcinoma, Krompecher's carcinoma, Kulchitzky-cell carcinoma, lenticular carcinoma, carcinoma lenticulare, lipomatous carcinoma, lymphoepithelial carcinoma, carcinoma mastitoides, carcinoma medullare, medullary carcinoma, carcinoma melanodes, melanotic carcinoma, mucinous carcinoma, carcinoma muciparum, carcinoma mucocellulare, mucoepidermoid carcinoma, carcinoma mucosum, mucous carcinoma, carcinoma myxomatodes, nasopharyngeal carcinoma, carcinoma nigrum, oat cell carcinoma, carcinoma ossificans, osteoid carcinoma, ovarian carcinoma, papillary carcinoma, periportal carcinoma, preinvasive carcinoma, prostate carcinoma, renal cell carcinoma of kidney (also called adenocarcinoma of kidney and hypemephoroid carcinoma), reserve cell carcinoma, carcinoma sarcomatodes, scheinderian carcinoma, scirrhous carcinoma, carcinoma scroti, signet-ring cell carcinoma, carcinoma simplex, small-cell carcinoma, solanoid carcinoma, spheroidal cell carcinoma, spindle cell carcinoma, carcinoma spongiosum, squamous carcinoma, squamous cell carcinoma, string carcinoma, carcinoma telangiectaticum, carcinoma telangiectodes, transitional cell carcinoma, carcinoma tuberosum, tuberous carcinoma, verrucous carcinoma, carcinoma vilosum. In preferred embodiments, the methods of the invention are used to treat subjects having cancer of the breast, cervix, ovary, prostate, lung, colon and rectum, pancreas, stomach or kidney.

Another particularly important cancer type is sarcomas. Sarcomas are rare mesenchymal neoplasms that arise in bone and soft tissues. Different types of sarcomas are recognized and these include: liposarcomas (including myxoid liposarcomas and pleiomorphic liposarcomas), leiomyosarcomas, rhabdomyosarcomas, malignant peripheral nerve sheath tumors (also called malignant schwannomas, neurofibrosarcomas, or neurogenic sarcomas), Ewing's tumors (including Ewing's sarcoma of bone, extraskeletal (i.e., non-bone) Ewing's sarcoma, and primitive neuroectodermal tumor [PNET]), synovial sarcoma, angiosarcomas, hemangiosarcomas, lymphangiosarcomas, Kaposi's sarcoma, hemangioendothelioma, fibrosarcoma, desmoid tumor (also called aggressive fibromatosis), dermatofibrosarcoma protuberans (DFSP), malignant fibrous histiocytoma (MFH), hemangiopericytoma, malignant mesenchymoma, alveolar soft-part sarcoma, epithelioid sarcoma, clear cell sarcoma, desmoplastic small cell tumor, gastrointestinal stromal tumor (GIST) (also known as GI stromal sarcoma), osteosarcoma (also known as osteogenic sarcoma)-skeletal and extraskeletal, and chondrosarcoma.

In some embodiments, the cancers to be treated are refractory cancers. A "refractory cancer" as used herein is a cancer that is resistant to the ordinary standard of care prescribed. These cancers may appear initially responsive to a treatment (and then recur), or they may be completely non-responsive to the treatment. The ordinary standard of care will vary depending upon the cancer type, and the degree of progression in the subject. It may be a chemotherapy, or surgery, or radiation, or a combination thereof. Those of ordinary skill in the art are aware of such standards of care. Subjects being treated according to the invention for a refractory cancer therefore may have already been exposed to another treatment for their cancer. Alternatively, if the cancer is likely to be refractory (e.g., given an analysis of the cancer cells or history of the subject), then the subject may not have already been exposed to another treatment.

Examples of refractory cancers include, but are not limited to, leukemias, melanomas, renal cell carcinomas, colon cancer, liver (hepatic) cancers, pancreatic cancer, Non-Hodgkin's lymphoma, and lung cancer.

The invention can also be used to treat cancers that are immunogenic. Cancers that are immunogenic are cancers that are known to (or likely to) express immunogens on their surface or upon cell death. These immunogens are in vivo endogenous sources of cancer antigens and their release can be exploited by the methods of the invention in order to treat the cancer. Examples of immunogenic cancers include, for example, malignant melanoma and renal cell cancer.

Subjects at risk of developing a cancer include subjects that are known or are suspected of being exposed to a carcinogen. A carcinogen is an agent capable of initiating development of malignant cancers. Exposure to carcinogens generally increases the risk of neoplasms in subjects, usually by affecting DNA directly. Carcinogens may take one of several forms such as chemical, electromagnetic radiation, or may be an inert solid body. Examples of chemical carcinogens include tobacco, asbestos, and the like.

In some embodiments, the goal of immunotherapy (e.g., with the compositions and methods of the present invention) is to augment a patient's immune response to an established tumor. Different types of cells that can kill tumor targets in vitro and in vivo have been identified: natural killer cells (NK cells), cytolytic T lymphocytes (CTLs), lymphokine-activated killer cells (LAKs), activated macrophages, and neutrophils. NK cells can kill tumor cells without having been previously sensitized to specific antigens, and the activity does not require the presence of class I antigens encoded by the major histocompatibility complex (MHC) on target cells. NK cells are thought to participate in the control of nascent tumors and in the control of metastatic growth. In contrast to NK cells, CTLs can kill tumor cells only after they have been sensitized to tumor antigens and when the target antigen is expressed on the tumor cells that also express MHC class 1. CTLs are thought to be effector cells in the rejection of transplanted tumors and of tumors caused by DNA viruses. LAK cells are a subset of null lymphocytes distinct from the NK and CTL populations. Activated macrophages and neutrophils can directly kill tumor cells in a manner that is not antigen dependent nor MHC restricted. In addition, neutrophils can inhibit tumor growth by killing endothelial cells of the vasculature that provide blood supply to the tumor. Thus, activated macrophages and neutrophils are thought to decrease the growth rate of the tumors they infiltrate.

The vaccine methods and compositions described herein similarly envision the use of nucleic acid based vaccines in addition to peptide based vaccines. The art is familiar with nucleic acid based vaccines.

The invention seeks to enhance other forms of immunotherapy including dendritic cell vaccines. These vaccines generally include dendritic cells loaded ex vivo with antigens such as tumor-associated antigens. The dendritic cells can be incubated with the antigen, thereby allowing for antigen processing and expression on the cell surface, or the cells may simply be combined with the antigen prior to injection in vivo. Alternatively, the dendritic cells may be activated in vitro and then re-infused into a subject in the activated state. In some embodiments, an agent comprising JFPB, JFPH, and/or functional equivalent can be combined with the dendritic cells in all of these embodiments. Examples of dendritic cell based vaccines include autologous tumour antigen-pulsed dendritic cells (advanced gynaecological malignancies); blood-derived dendritic cells loaded ex vivo with prostate cancer antigen (Provenge; Dendreon Corporation); blood-derived dendritic cells loaded ex vivo with antigen for multiple myeloma and other B-cell malignancies (Mylovenge; Dendreon Corporation); and blood-derived dendritic cells loaded ex vivo with antigen for cancers expressing the HER-2/neu proto-oncogene (APC8024; Dendreon Corporation); xenoantigen (e.g., PAP) loaded dendritic cells, and the like.

One advantage of the combined use of an agent comprising JFPB, JFPH, and/or functional equivalent and the foregoing vaccines is the reduction in the number of immunizations that a subject must receive in order to achieve a therapeutically or prophylactically effective immune response. For example, for some infectious diseases, three or more vaccinations are required before a fully effective immune response is generated and the subject is immunized. This number can be reduced by combining an agent comprising JFPB, JFPH, and/or functional equivalent compound administration with the vaccine, either physically or temporally. Accordingly, in some embodiments, an agent comprising JFPB, JFPH, and/or functional equivalent compounds are particularly suited for administering to subjects at risk of infectious disease.

Another form of immunotherapy is the use of lymphokine activated killer cells (LAKs) that are primed in vitro with lymphokines and then re-infused into a subject. In some embodiments, an agent comprising JFPB, JFPH, and/or functional equivalent are combined with such cells either as an addition to the activating lymphokine or in place of it.

A subject shall mean a human or animal including but not limited to a dog, cat, horse, cow, pig, sheep, goat, chicken, rodent e.g., rats and mice, primate, e.g., monkey, and fish or aquaculture species such as fin fish (e.g., salmon) and shellfish (e.g., shrimp and scallops). Subjects suitable for therapeutic or prophylactic methods include vertebrate and invertebrate species. Subjects can be house pets (e.g., dogs, cats, fish, etc.), agricultural stock animals (e.g., cows, horses, pigs, chickens, etc.), laboratory animals (e.g., mice, rats, rabbits, etc.), zoo animals (e.g., lions, giraffes, etc.), but are not so limited. Although many of the embodiments described herein relate to human disorders, the invention is also useful for treating other nonhuman vertebrates.

The present invention also embraces the use of adjuvants. Adjuvant substances derived from microorganisms, such as *bacillus* Calmette-Guerin, heighten the immune response and enhance resistance to tumors in animals. Adjuvants that may be combined with an agent comprising JFPB, JFPH, and/or functional equivalent include alum, immunostimulatory oligonucleotides such as CpG oligonucleotides, QS-21, and the like. These and other adjuvants are listed herein in greater detail.

The term "effective amount" of either individual or combination of compounds refers to the amount necessary or sufficient to realize a desired biologic effect. For example, in some embodiments, an effective amount of the combination is that amount necessary to cause activation of the immune system. In some embodiments, this results in the development of an antigen specific immune response. Generally, an effective amount is that amount that provides a biologically beneficial effect. The biologically beneficial effect may be the amelioration and or absolute elimination of symptoms resulting from the disorder being treated e.g., cancer or infectious disease. In another embodiment, the biologically beneficial effect is the complete abrogation of the disorder e.g., cancer, as evidenced for example, by the absence of a tumor or a biopsy or blood smear which is free of cancer cells. In other embodiments, the desired biologic effect is the prevention of a disease state (e.g., cancer or infectious disease).

The effective amount may vary depending upon the particular compound and the particular antibody used. The effective amount for any particular application can also vary depending on such factors as the cancer being treated, the size of the subject, or the severity of the disease or condition. One of ordinary skill in the art can empirically determine the effective amount of a particular composition comprising JFPB, JFPH, and/or functional equivalent and anti-cancer antibody combination without necessitating undue experimentation. Combined with the teachings provided herein, by choosing among the various active compounds and weighing factors such as potency, relative bioavailability, patient body weight, severity of adverse side-effects and preferred mode of administration, an effective prophylactic or therapeutic treatment regimen can be planned which does not cause substantial toxicity and yet is entirely effective to treat the particular subject.

In some instances, a sub-therapeutic dosage of either an agent comprising JFPB, JFPH, and/or functional equivalent or the anti-cancer treatment, or a sub-therapeutic dosage of both, is used in the treatment of a subject having, or at risk of developing cancer. As an example, it has been discovered according to the invention, that when the two classes of drugs are used together, the anti-cancer antibody can be administered in a sub-therapeutic dose and still produce a desirable therapeutic result. A "sub-therapeutic dose" as used herein refers to a dosage which is less than that dosage which would produce a therapeutic result in the subject if administered in the absence of the other agent. Thus, the sub-therapeutic dose of a anti-cancer antibody is one which would not produce the desired therapeutic result in the subject in the absence of the administration of an agent comprising JFPB, JFPH, and/or functional equivalent. Therapeutic doses of anti-cancer antibodies are well known in the field of medicine for the treatment of cancer. These dosages have been extensively described in references such as Remington's Pharmaceutical Sciences, 18th ed., 1990, or the Physician Desktop Reference; as well as many other medical references relied upon by the medical profession as guidance for the treatment of cancer.

For any compound described herein a therapeutically effective amount can be initially determined from cell culture assays. In particular, the effective amount of an agent comprising JFPB, JFPH, and/or functional equivalent can be determined using in vitro stimulation assays. The stimulation index of immune cells can be used to determine an effective amount of the particular compound for the particular subject, and the dosage can be adjusted upwards or downwards to achieve the desired levels in the subject.

Therapeutically effective amounts can also be determined in animal studies. For instance, the effective amount of an agent comprising JFPB, JFPH, and/or functional equivalent and an anti-cancer antibody to induce a synergistic response can be assessed using in vivo assays of tumor regression and/or prevention of tumor formation. Relevant animal models include assays in which malignant cells are injected into the animal subjects, usually in a defined site. Generally, a range of doses of an agent comprising JFPB, JFPH, and/or functional equivalent are administered into the animal along with a range of anti-cancer antibody doses. Inhibition of the growth of a tumor following the injection of the malignant cells is indicative of the ability to reduce the risk of developing a cancer. Inhibition of further growth (or reduction in size) of a pre-existing tumor is indicative of the ability to treat the cancer. Mice which have been modified to have human immune system elements can be used as recipients of human cancer cell lines to determine the effective amount of the synergistic combination.

The applied dose of both agents can be adjusted based on the relative bioavailability and potency of the administered compounds, including the adjuvants used. Adjusting the dose to achieve maximal efficacy based on the methods described above and other methods are well within the capabilities of the ordinarily skilled artisan.

Subject doses of the compounds described herein typically range from about 0.1 µg to 10,000 mg, more typically from about 1 µg/day to 8000 mg, even more typically from about 10 µg to 5 mg, and most typically from about 10 µg to 100 pg. Stated in terms of subject body weight, typical dosages range from about 0.1 µg to 20 mg/kg/day, more typically from about 1 to 10 mg/kg/day, and most typically from about 1 to 5 mg/kg/day (e.g., of JFPH is administered), although daily doses may be more than 20 mg/kg/day or less than 0.1 µg/kg/day.

For example, in some embodiments, the agent is administered in amounts of less than or equal to 1.0 mg/kg per day. This includes amounts equal to or less than 0.9, 0.8, 0.7, 0.6, 0.5, 0.4, 0.3, 0.2, 0.1 mg/kg per day. The agents may also be administered in amounts of less than or equal to 0.1 mg/kg per day (e.g., less than or equal to 0.09, 0.08, 0.07, 0.06, 0.5, 0.04, 0.03, 0.02 or 0.01 mg/kg/day). In some embodiments, the agents are administered in a range of about 0.005 mg/kg per day to less than 1.0 mg/kg per day (or about 0.005 mg/kg per day to equal to or less than 0.1 mg/kg per day). In some embodiments, more than 20 mg/kg/day In some embodiments (e.g., in methods particularly directed at subjects at risk of developing a disorder), timing of the administration of an agent comprising JFPB, JFPH, and/or functional equivalent and the anti-cancer antibody or antibody fragment may be particularly important. For instance, in a subject with a genetic predisposition to cancer, the agents may be administered to the subject on a routine schedule.

A "routine schedule" as used herein, refers to a predetermined designated period of time. The routine schedule may encompass periods of time which are identical or which differ in length, as long as the schedule is predetermined. For instance, the routine schedule may involve administration on a daily basis, every two days, every three days, every four days, every five days, every six days, a weekly basis, a monthly basis or any set number of days or weeks therebetween, every two months, three months, four months, five months, six months, seven months, eight months, nine months, ten months, eleven months, twelve months, etc. Alternatively, the predetermined routine schedule may involve administration on a daily basis for the first week, followed by a monthly basis for several months, and then every three months after that. Any particular combination would be covered by the routine schedule as long as it is determined ahead of time that the appropriate schedule involves administration on a certain day.

In some embodiments, an agent comprising JFPB, JFPH, and/or functional equivalent of the invention is administered neat, or in the context of a vector or delivery system. An example of a chemical/physical vector of the invention is a colloidal dispersion system. Colloidal dispersion systems include lipid-based systems including oil-in-water emulsions, micelles, mixed micelles, and liposomes. A preferred colloidal system of the invention is a liposome. Liposomes are artificial membrane vessels which are useful as a delivery vector in vivo or in vitro. It has been shown that large unilamellar vessels (LUV), which range in size from 0.2-4.0 µm can encapsulate large macromolecules. RNA, DNA and intact virions can be encapsulated within the aqueous interior and be delivered to cells in a biologically active form (Fraley, et al., Trends Biochem. Sci., (1981) 6:77).

Liposomes may be targeted to a particular tissue by coupling the liposome to a specific ligand such as a sugar, glycolipid, or protein. Ligands which may be useful for targeting a liposome to an immune cell include, but are not limited to: intact or fragments of molecules which interact with immune cell specific receptors and molecules, such as antibodies, which interact with the cell surface markers of immune cells. Such ligands may easily be identified by binding assays well known to those of skill in the art. In still other embodiments, the liposome may be targeted to the cancer by coupling it to a one of the immunotherapeutic antibodies discussed earlier. Additionally, the vector may be coupled to a nuclear targeting peptide, which will direct the vector to the nucleus of the host cell.

Lipid formulations for transfection are commercially available from QIAGEN, for example, as EFFECTENE (a non-liposomal lipid with a special DNA condensing enhancer) and SUPERFECT (a novel acting dendrimeric technology).

Liposomes are commercially available from Gibco BRL, for example, as LIPOFECTIN and LIPOFECTACE, which are formed of cationic lipids such as N-[1-(2,3 dioleyloxy)-propyl]-N,N, N-trimethylammonium chloride (DOTMA) and dimethyl dioctadecylammoniuin bromide (DDAB). Methods for making liposomes are well known in the art and have been described in many publications. Liposomes also have been reviewed by Gregoriadis, G. in Trends in Biotechnology, (1985) 3:235-241.

In another embodiment the chemical/physical vector is a biocompatible microsphere that is suitable for delivery, such as oral or mucosal delivery. Such microspheres are disclosed in Chickering et al., Biotech. And Bioeng., (1996) 52:96-101 and Mathiowitz et al., Nature, (1997) 386:.410-414 and PCT Patent Application WO97/03702.

Both non-biodegradable and biodegradable polymeric matrices can be used to deliver an agent comprising JFPB, JFPH, and/or functional equivalent and/or the anti-cancer antibody to the subject. Biodegradable matrices are preferred. Such polymers may be natural or synthetic polymers. The polymer is selected based on the period of time over which release is desired, generally in the order of a few hours to a year or longer. Typically, release over a period ranging from between a few hours and three to twelve months is most desirable. The polymer optionally is in the form of a hydrogel that can absorb up to about 90% of its weight in water and further, optionally is cross-linked with multi-valent ions or other polymers.

The polymeric matrix preferably is in the form of a microparticle such as a microsphere (wherein the agents are dispersed throughout a solid polymeric matrix) or a microcapsule (wherein the agents are stored in the core of a polymeric shell). Other forms of the polymeric matrix for containing the agents include films, coatings, gels, implants, and stents. The size and composition of the polymeric matrix device is selected to result in favorable release kinetics in the tissue into which the matrix is introduced. The size of the polymeric matrix further is selected according to the method of delivery which is to be used, typically injection into a tissue or administration of a suspension by aerosol into the nasal and/or pulmonary areas. Preferably when an aerosol route is used the polymeric matrix and an agent comprising JFPB, JFPH, and/or functional equivalent and the anti-cancer antibody are encompassed in a surfactant vehicle. The polymeric matrix composition can be selected to have both favorable degradation rates and also to be formed of a material which is bioadhesive, to further increase the effectiveness of transfer when the matrix is administered to a nasal and/or pulmonary surface that has sustained an injury. The matrix composition also can be selected not to degrade, but rather, to release by diffusion over an extended period of time. In some embodiments, an agent comprising JFPB, JFPH, and/or functional equivalent is administered to the subject via an implant while the anti-cancer antibody is administered acutely.

Bioadhesive polymers of particular interest include bioerodible hydrogels described by H. S. Sawhney, C. P. Pathak and J. A. Hubell in Macromolecules, (1993) 26:581-587, the teachings of which are incorporated herein, polyhyaluronic acids, casein, gelatin, glutin, polyanhydrides, polyacrylic acid, alginate, chitosan, poly(methyl methacrylates), poly (ethyl methacrylates), poly(butylmethacrylate), poly(isobutyl methacrylate), poly(hexylmethacrylate), poly(isodecyl methacrylate), poly(laurel methacrylate), poly(phenyl methacrylate), poly(methyl acrylate), poly(isopropyl acrylate), poly(isobutyl acrylate), and poly(octadecyl acrylate).

Other delivery vehicles can be used and these include: cochleates (Gould-Fogerite et al., 1994, 1996); Emulsomes (Vancott et al., 1998, Lowell et al., 1997); ISCOMs (Mowat et al., 1993, Carlsson et al., 1991, Hu et., 1998, Morein et al., 1999); liposomes (Childers et al., 1999, Michalek et al., 1989, 1992, de Haan 1995a, 1995b); live bacterial vectors (e.g., *Salmonella, Escherichia coli, Bacillus* calmatte-guerin, *Shigella, Lactobacillus*) (Hone et al., 1996, Pouwels et al., 1998, Chatfield et al., 1993, Stover et al., 1991, Nugent et al., 1998); live viral vectors (e.g., Vaccinia, adenovirus, Herpes Simplex) (Gallichan et al., 1993, 1995, Moss et al., 1996, Nugent et al., 1998, Flexner et al., 1988, Morrow et al., 1999); microspheres (Gupta et al., 1998, Jones et al., 1996, Maloy et al., 1994, Moore et al., 1995, O'Hagan et al., 1994, Eldridge et al., 1989); nucleic acid vaccines (Fynan et al., 1993, Kuklin et al., 1997, Sasaki et al., 1998, Okada et al., 1997, Ishii et al., 1997); polymers (e.g. carboxymethylcellulose, chitosan) (Hamajima et al., 1998, Jabbal-Gill et al., 1998); polymer rings (Wyatt et al., 1998); proteosomes (Vancott et al., 1998, Lowell et al., 1988, 1996, 1997); sodium fluoride (Hashi et al., 1998); transgenic plants (Tacket et al., 1998, Mason et al., 1998, Haq et al., 1995); virosomes (Gluck et al., 1992, Mengiardi et al., 1995, Cryz et al., 1998); and, virus-like particles (Jiang et al., 1999, Leibl et al., 1998).

The compositions and methods of the invention in certain instances may be useful for replacing existing surgical procedures or drug therapies, although in most instances the present invention is useful in improving the efficacy of existing therapies for treating such conditions. Accordingly combination therapy may be used to treat the subjects that are undergoing or that will undergo a treatment for inter alia cancer or infectious disease. For example, an agent comprising JFPB, JFPH, and/or functional equivalent may be administered to a subject in combination with another anti-proliferative (e.g., an anti-cancer) therapy. Suitable anti-cancer therapies include surgical procedures to remove the tumor mass, chemotherapy or localized radiation. The other antiproliferative therapy may be administered before, concurrent with, or after treatment with the agent of the invention. There may also be a delay of several hours, days and in some instances weeks between the administration of the different treatments, such that the agent may be administered before or after the other treatment. In some embodiments, an agent comprising JFPB, JFPH, and/or functional equivalent may be administered with or without the antigens or antibodies, prior to the administration of the other anti-proliferative treatment (e.g., prior to surgery, radiation or chemotherapy), although the timing is not so limited. Although not intending to be bound by any particular mechanism, it is proposed that the administration of an agent comprising JFPB, JFPH, and/or functional equivalent inducing memory within the immune cell compartment, for example, by the induction of memory T cells, and B cells. Although a mechanism is not needed to practice the present invention, and the invention is not limited to any particular mechanism, this is believed to occur via the enhanced expression of cytokines induced by an agent comprising JFPB, JFPH, and/or functional equivalent, particularly the induction of IL-2 and/or IFN-γ. The ability to generate memory T cells can enhance immune responses to, for example, cancerous cells that are remaining following a surgical procedure, or following chemotherapy or radiation. The invention further contemplates the use an agent comprising JFPB, JFPH, and/or functional equivalent in cancer subjects prior to and following surgery, radiation or chemotherapy in order to create memory immune cells to the cancer antigen. In this way, memory cells of the immune system can be primed with cancer antigens and thereby provide immune surveillance in the long term. This is particularly suited to radiotherapy of subjects where immune cells so primed can invade a tumor site and effectively clear any remaining tumor debris. This in turn promotes further immunity to the cancer, particularly to antigens that might not have been exposed in the context of a tumor mass pre-treatment.

It is to be understood that in other embodiments, subjects can be treated with an agent comprising JFPB, JFPH, and/or functional equivalent without any other therapy, as well. In some embodiments of the present invention, the methods are particularly directed to subjects at high risk of cancer, such as those predisposed for familial (e.g., familial colon polyposis, BRCA1- or BRCA2-associated breast cancer, Wilms tumour, colorectal cancer, Li-Fraumeni Syndrome, ovarian cancer, and prostate cancer), or non-familial genetic reasons. Subjects at high risk are also those that manifest pre-cancerous symptoms such as pre-cancerous polyps (e.g., in colon cancer), or pre-cancerous lesions (e.g., in HPV-induced cervical cancer).

In some embodiments, an agent comprising JFPB, JFPH, and/or functional equivalent can also be administered in combination with non-surgical anti-proliferative (e.g., anti-cancer) drug therapy. In one embodiment, the agent may be administered in combination with an anti-cancer compound such as a cytostatic compound. A cytostatic compound is a compound (e.g., a nucleic acid, a protein) that suppresses cell growth and/or proliferation. In some embodiments, the cytostatic compound is directed towards the malignant cells of a tumor. In yet other embodiments, the cytostatic compound is one which inhibits the growth and/or proliferation of vascular smooth muscle cells or fibroblasts.

According to the methods of the invention, an agent comprising JFPB, JFPH, and/or functional equivalent and the anti-cancer antibodies may be administered prior to, concurrent with, or following other anti-cancer compounds. The administration schedule may involve administering the different agents in an alternating fashion. In other embodiments, the combination therapy of the invention may be delivered before and during, or during and after, or before and after treatment with other therapies. In some cases, the agent is administered more than 24 hours before the administration of the other anti-proliferative treatment. In other embodiments, more than one anti-proliferative therapy may be administered to a subject. For example, the subject may receive the agents of the invention, in combination with both surgery and at least one other anti-proliferative compound. Alternatively, the agent may be administered in combination with more than one anti-cancer drug.

In some embodiments, an agent comprising JFPB, JFPH, and/or functional equivalent and anti-cancer antibodies can be combined with other therapeutic agents such as adjuvants to enhance immune responses even further. An agent comprising JFPB, JFPH, and/or functional equivalent, anti-cancer antibody, and other therapeutic agent may be administered simultaneously or sequentially. When the other therapeutic agents are administered simultaneously they can be administered in the same or separate formulations, but are administered at the same time. The administration of the other therapeutic agents (such as adjuvants) and an agent comprising JFPB, JFPH, and/or functional equivalent and anti-cancer antibodies can also be temporally separated, meaning that the therapeutic agents are administered at a different time, either before or after, the administration of an agent comprising JFPB, JFPH, and/or functional equivalent and anti-cancer antibodies. The separation in time between the administration of these compounds may be a matter of minutes or it may be longer. Other therapeutic agents include but are not limited to nucleic acid adjuvants, non-nucleic acid adjuvants, cytokines, non-immunotherapeutic antibodies, antigens, etc.

A nucleic acid adjuvant is an adjuvant that is a nucleic acid. Examples include immunostimulatory nucleic acid molecules such as those containing CpG dinucleotides, as described in U.S. Pat. No. 6,194,388B1, issued Feb. 27, 2001, U.S. Pat. No. 6,207,646 B1, issued Mar. 27, 2001, and U.S. Pat. No. 6,239,116 B1, issued May 29, 2001.

A "non-nucleic acid adjuvant" is any molecule or compound except for the immunostimulatory nucleic acids described herein which can stimulate the humoral and/or cellular immune response. Non-nucleic acid adjuvants include, for instance, adjuvants that create a depo effect, immune-stimulating adjuvants, adjuvants that create a depo effect and stimulate the immune system and mucosal adjuvants.

An "adjuvant that creates a depo effect" as used herein is an adjuvant that causes an antigen, such as a cancer antigen present in a cancer vaccine, to be slowly released in the body, thus prolonging the exposure of immune cells to the antigen. This class of adjuvants includes but is not limited to alum (e.g., aluminum hydroxide, aluminum phosphate); or emulsion-based formulations including mineral oil, non-mineral oil, water-in-oil or oil-in-water-in oil emulsion, oil-in-water emulsions such as Seppic ISA series of Montanide adjuvants (e.g., Montanide ISA 720, AirLiquide, Paris, France); MF-59 (a squalene-in-water emulsion stabilized with Span 85 and Tween 80; Chiron Corporation, Emeryville, Calif.; and PROVAX (an oil-in-water emulsion containing a stabilizing detergent and a micelle-forming agent; IDEC Pharmaceuticals Corporation, San Diego, Calif.).

An "immune stimulating adjuvant" is an adjuvant that causes activation of a cell of the immune system. It may, for instance, cause an immune cell to produce and secrete cytokines. This class of adjuvants includes but is not limited to saponins purified from the bark of the *Q. saponaria* tree, such as QS21 (a glycolipid that elutes in the 21.sup.st peak with HPLC fractionation; Antigenics, Inc., Waltham, Mass.); poly [di(carboxylatophenoxy) phosphazene (PCPP polymer; Virus Research Institute, USA); derivatives of lipopolysaccharides such as monophosphoryl lipid A (MPL; Ribi ImmunoChem Research, Inc., Hamilton, Mont.), muramyl dipeptide (MDP; Ribi) and threonyl-muramyl dipeptide (t-MDP; Ribi); OM-174 (a glucosamine disaccharide related to lipid A; OM Pharma SA, Meyrin, Switzerland); and *Leishmania* elongation factor (a purified *Leishmania* protein; Corixa Corporation, Seattle, Wash.).

"Adjuvants that create a depo effect and stimulate the immune system" are those compounds which have both of the above-identified functions. This class of adjuvants includes but is not limited to ISCOMS (Immunostimulating complexes which contain mixed saponins, lipids and form virus-sized particles with pores that can hold antigen; CSL, Melbourne, Australia); SB-AS2 (SmithKline Beecham adjuvant system #2 which is an oil-in-water emulsion containing MPL and QS21: SmithKline Beecham Biologicals [SBB], Rixensart, Belgium); SB-AS4 (SmithKline Beecham adjuvant system #4 which contains alum and MPL; SBB, Belgium); non-ionic block copolymers that form micelles such as CRL 1005 (these contain a linear chain of hydrophobic polyoxpropylene flanked by chains of polyoxyethylene; Vaxcel, Inc., Norcross, Ga.); and Syntex Adjuvant Formulation (SAF, an oil-in-water emulsion containing Tween 80 and a nonionic block copolymer; Syntex Chemicals, Inc., Boulder, Colo.).

A "non-nucleic acid mucosal adjuvant" as used herein is an adjuvant other than an immunostimulatory nucleic acid that is capable of inducing a mucosal immune response in a subject when administered to a mucosal surface in conjunction with an antigen. Mucosal adjuvants include but are not limited to Bacterial toxins: e.g., Cholera toxin (CT), CT derivatives including but not limited to CT B subunit (CTB) (Wu et al., 1998, Tochikubo et al., 1998); CTD53 (Val to Asp) (Fontana et al., 1995); CTK97 (Val to Lys) (Fontana et al., 1995); CTK104 (Tyr to Lys) (Fontana et al., 1995); CTD53/K63 (Val to Asp, Ser to Lys) (Fontana et al., 1995); CTH54 (Arg to His) (Fontana et al., 1995); CTN107 (His to Asn) (Fontana et al., 1995); CTE114 (Ser to Glu) (Fontana et al., 1995); CTE112K (Glu to Lys) (Yamamoto et al., 1997a); CTS61F (Ser to Phe) (Yamamoto et al., 1997a, 1997b); CTS106 (Pro to Lys) (Douce et al., 1997, Fontana et al., 1995); and CTK63 (Ser to Lys) (Douce et al., 1997, Fontana et al., 1995), Zonula occludens toxin, zot, *Escherichia coli* heat-labile enterotoxin, Labile Toxin (LT), LT derivatives including but not limited to LT B subunit (LTB) (Verweij et al., 1998); LT7K (Arg to Lys) (Komase et al., 1998, Douce et al., 1995); LT61F (Ser to Phe) (Komase et al., 1998); LT112K (Glu to Lys) (Komase et al., 1998); LT118E (Gly to Glu) (Komase et al., 1998); LT146E (Arg to Glu) (Komase et al., 1998); LT192G (Arg to Gly) (Komase et al., 1998); LTK63 (Ser to Lys) (Marchetti et al., 1998, Douce et al., 1997, 1998, Di Tommaso et al., 1996); and LTR72 (Ala to Arg) (Giuliani et al., 1998), Pertussis toxin, PT. (Lycke et al., 1992, Spangler B D, 1992, Freytag and Clemments, 1999, Roberts et al., 1995, Wilson et al., 1995) including PT-9K/129G (Roberts et al., 1995, Cropley et al., 1995); Toxin derivatives (see below) (Holmgren et al., 1993, Verweij et al., 1998, Rappuoli et al., 1995, Freytag and Clements, 1999); Lipid A derivatives (e.g., monophosphoryl lipid A, MPL) (Sasaki et al., 1998, Vancott et al., 1998; Muramyl Dipeptide (MDP) derivatives (Fukushima et al., 1996, Ogawa et al., 1989, Michalek et al., 1983, Morisaki et al., 1983); Bacterial outer membrane proteins (e.g., outer surface protein A (OspA) lipoprotein of *Borrelia hurgdorferi*, outer membrane protine of *Neisseria meningitidis*)(Marinaro et al., 1999, Van de Verg et al., 1996); Oil-in-water emulsions (e.g., MF59) (Barchfield et al., 1999, Verschoor et al., 1999, O'Hagan, 1998); Aluminum salts (Isaka et al., 1998, 1999); and Saponins (e.g., QS21) Aquila Biopharmaceuticals, Inc., Worcester, Mass.) (Sasaki et al., 1998, MacNeal et al., 1998), ISCOMS, MF-59 (a squalene-in-water emulsion stabilized with Span 85 and Tween 80; Chiron Corporation, Emeryville, Calif.); the Seppic ISA series of Montanide adjuvants (e.g., Montanide ISA 720; AirLiquide, Paris, France); PROVAX (an oil-in-water emulsion containing a stabilizing detergent and a micell-forming agent; IDEC Pharmaceuticals Corporation, San Diego, Calif.); Syntext Adjuvant Formulation (SAF; Syntex Chemicals, Inc., Boulder, Colo.); poly[di(carboxylatophenoxy)phosphazene (PCPP polymer; Virus Research Institute, USA) and *Leishmania* elongation factor (Corixa Corporation, Seattle, Wash.).

Cytokines and chemokines can potentially be cleaved and thereby inactivated by post proline cleaving enzymes. In some embodiments, administration of an agent comprising JFPB, JFPH, and/or functional equivalent with cytokines and/or chemokines enhances the efficacy of these latter agents by protecting them from degradation.

Immune responses can also be induced or augmented by the co-administration or co-linear expression of cytokines or chemokines (Bueler & Mulligan, 1996; Chow et al., 1997; Geissler et al., 1997; Iwasaki et al., 1997; Kim et al., 1997) or B-7 co-stimulatory molecules (Iwasaki et al., 1997; Tsuji et al., 1997) with an agent comprising JFPB, JFPH, and/or functional equivalent and anti-cancer antibodies. The cytokines and/or chemokines can be administered directly or may be administered in the form of a nucleic acid vector that encodes the cytokine, such that the cytokine can be expressed in vivo. In some embodiments, the cytokine or chemokine is administered in the form of a plasmid expression vector. The term "cytokine" is used as a generic name for a diverse group of soluble proteins and peptides which act as humoral regulators at nano- to picomolar concentrations and which, either under normal or pathological conditions, modulate the functional activities of individual cells and tissues. These proteins also mediate interactions between cells directly and regulate processes taking place in the extracellular environment. Cytokines also are central in directing the T cell response. Examples of cytokines include, but are not limited to IL-1, IL-2, IL-4, IL-5, IL-6, IL-7, IL-10, IL-12, IL-15, IL-18, granulocyte-macrophage colony stimulating factor (GM-CSF), granulocyte colony stimulating factor (G-CSF), interferon-$\gamma$ (WFN-$\gamma$), IFN-$\alpha$, tumor necrosis factor (TNF), TGF-$\beta$, FLT-3 ligand, and CD154 (CD40 ligand). In some embodiments, the cytokine is a Th1 cytokine. In still other embodiments, the cytokine is a Th2 cytokine.

The term "chemokine" is used as a generic name for peptides or polypeptides that act principally to chemoattract effector cells of both innate and adaptive immunity. In general, chemokines are subset of cytokines. Chemokines are thought to coordinate immunological defenses against tumors and infectious agents by concentrating neutrophils, macrophages, eosinophils and T and B lymphocytes at the anatomical site in which the tumor or infectious agent is present. In addition, many chemokines are known to activate the effector cells so that their immune functions (e.g., cytolysis of tumor cells) are enhanced on a per cell basis. Two groups of chemokines are distinguished according to the positions of the first two cysteine residues that are conserved in the amino-terminal portions of the polypeptides. The residues can either be adjacent or separated by one amino acid, thereby defining the CC and CXC cytokines respectively. The activity of each chemokine is restricted to particular effector cells, and this specificity results from a cognate interaction between the chemokine and a specific cell membrane receptor expressed by the effector cells. For example, the CXC chemokines IL-8, Gro$\alpha$/$\beta$, and ENA 78 act specifically on neutrophils, whereas the CC cheinokines RANTES, MIP-1$\alpha$ and MCP-3 act oil monocytes and activated T cells. In addition, the CXC chemokine IP-10 appears to have anti-angiogenic activity against tumors as well as being a chemoattractant for activated T cells. MIP-1$\alpha$ also reportedly has effects on hemopoietic precursor cells.

In other aspects, the invention relates to kits that are useful in the treatment of disease (e.g., cancer or infectious disease). One kit of the invention includes a sustained release vehicle containing an agent comprising JFPB, JFPH, and/or functional equivalent and a container housing an anti-cancer antibody (or an antigen) and instructions for timing of administration of the both. A sustained release vehicle is used herein in accordance with its prior art meaning of any device which slowly releases an agent comprising JFPB, JFPH, and/or functional equivalent.

Such systems can avoid repeated administrations of the compounds, increasing convenience to the subject and the physician. Many types of release delivery systems are available and known to those of ordinary skill in the art. They include polymer base systems such as poly(lactide-glycolide), copolyoxalates, polycaprolactones, polyesteramides, polyorthoesters, polyhydroxybutyric acid, and polyanhydrides. Microcapsules of the foregoing polymers containing drugs are described in, for example, U.S. Pat. No. 5,075,109. Delivery systems also include non-polymer systems that are: lipids including sterols such as cholesterol, cholesterol esters and fatty acids or neutral fats such as mono-di- and tri-glycerides; hydrogel release systems; sylastic systems; peptide based systems; wax coatings; compressed tablets using conventional binders and excipients; partially fused implants; and the like. Specific examples include, but are not limited to: (a) erosional systems in which an agent of the invention is contained in a form within a matrix such as those described in U.S. Pat. Nos. 4,452,775, 4,675,189, and 5,736,152, and (b) diffusional systems in which an active component permeates at a controlled rate from a polymer such as described in U.S. Pat. Nos. 3,854,480, 5,133,974 and 5,407,686. In addition, pump-based hardware delivery systems can be used, some of which are adapted for implantation.

The pharmaceutical compositions of the invention contain an effective amount of an agent comprising JFPB, JFPH, and/or functional equivalent and anti-cancer antibody and/or an antigen and/or other therapeutic agents, optionally included in a pharmaceutically-acceptable carrier.

The terms "pharmaceutically acceptable" or "pharmacologically acceptable," as used herein, refer to compositions that do not substantially produce adverse allergic or immunological reactions when administered to a subject (e.g., an animal or a human). Moreover, in certain embodiments, the compositions of the present invention may be formulated for horticultural or agricultural use. Such formulations include dips, sprays, seed dressings, stem injections, sprays, and mists.

As used herein, the term "topically" refers to application of the compositions of the present invention to the surface of the skin and mucosal cells and tissues (e.g., alveolar, buccal, lingual, masticatory, or nasal mucosa, and other tissues and cells that line hollow organs or body cavities).

As used herein, the term "pharmaceutically acceptable carrier" refers to any of the standard pharmaceutical carriers including, but not limited to, phosphate buffered saline solution, water, emulsions (e.g., such as an oil/water or water/oil emulsions), and various types of wetting agents, any and all solvents, dispersion media, coatings, sodium lauryl sulfate, isotonic and absorption delaying agents, disintrigrants (e.g., potato starch or sodium starch glycolate), and the like. The compositions also can include stabilizers and preservatives. For examples of carriers, stabilizers and adjuvants. (See e.g., Martin, Remington's Pharmaceutical Sciences, 15th Ed., Mack Publ. Co., Easton, Pa. (1975), incorporated herein by reference).

As used herein, the term "pharmaceutically acceptable salt" refers to any salt (e.g., obtained by reaction with an acid or a base) of a compound of the present invention that is physiologically tolerated in the target subject (e.g., a mammalian subject, and/or in vivo or ex vivo, cells, tissues, or organs). "Salts" of the compounds of the present invention may be derived from inorganic or organic acids and bases.

Examples of acids include, but are not limited to, hydrochloric, hydrobromic, sulfuric, nitric, perchloric, fumaric, maleic, phosphoric, glycolic, lactic, salicylic, succinic, toluene-p-sulfonic, tartaric, acetic, citric, methanesulfonic, ethanesulfonic, formic, benzoic, malonic, sulfonic, naphthalene-2-sulfonic, benzenesulfonic acid, and the like. Other acids, such as oxalic, while not in themselves pharmaceutically acceptable, may be employed in the preparation of salts useful as intermediates in obtaining the compounds of the invention and their pharmaceutically acceptable acid addition salts.

Examples of bases include, but are not limited to, alkali metal (e.g., sodium) hydroxides, alkaline earth metal (e.g., magnesium) hydroxides, ammonia, and compounds of formula $NW_4^+$, wherein W is $C_{1-4}$ alkyl, and the like.

Examples of salts include, but are not limited to: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, flucoheptanoate, glycerophosphate, hemisulfate, heptanoate, hexanoate, chloride, bromide, iodide, 2-hydroxyethanesulfonate, lactate, maleate, methanesulfonate, 2-naphthalenesulfonate, nicotinate, oxalate, palmoate, pectinate, persulfate, phenylpropionate, picrate, pivalate, propionate, succinate, tartrate, thiocyanate, tosylate, undecanoate, and the like. Other examples of salts include anions of the compounds of the present invention compounded with a suitable cation such as $Na^+$, $NH_4^+$, and $NW_4^+$ (wherein W is a $C_{1-4}$ alkyl group), and the like. For therapeutic use, salts of the compounds of the present invention are contemplated as being pharmaceutically acceptable. However, salts of acids and bases that are non-pharmaceutically acceptable may also find use, for example, in the preparation or purification of a pharmaceutically acceptable compound.

For therapeutic use, salts of the compounds of the present invention are contemplated as being pharmaceutically acceptable. However, salts of acids and bases that are non-pharmaceutically acceptable may also find use, for example, in the preparation or purification of a pharmaceutically acceptable compound.

As used herein, the term "administration" refers to the act of giving a drug, prodrug, or other agent, or therapeutic treatment (e.g., compositions/agents of the present invention) to a physiological system (e.g., a subject or in vivo, in vitro, or ex vivo cells, tissues, and organs). Exemplary routes of administration to the human body can be through the eyes (opthalmic), mouth (oral), skin (transdermal), nose (nasal), lungs (inhalant), oral mucosa (buccal), ear, by injection (e.g., intravenously, subcutaneously, intratumorally, intraperitoneally, etc.) and the like.

As used herein, the term "co-administration" refers to the administration of at least two agent(s) (e.g., two or more of JFPB, JFPH, and/or functional equivalent) or other agent/therapy to a subject. In some embodiments, the co-administration of two or more agents/therapies is concurrent. In other embodiments, a first agent/therapy is administered prior to a second agent/therapy. Those of skill in the art understand that the formulations and/or routes of administration of the various agents/therapies used may vary. The appropriate dosage for co-administration can be readily determined by one skilled in the art. In some embodiments, when agents/therapies are co-administered, the respective agents/therapies are administered at lower dosages than appropriate for their administration alone. Thus, co-administration is especially desirable in embodiments where the co-administration of the agents/therapies lowers the requisite dosage of a known potentially harmful (e.g., toxic) agent(s).

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions. Another suitable compound for sustained release delivery is GELFOAM, a commercially available product consisting of modified collagen fibers.

Alternatively, the active compounds may be in powder form for constitution with a suitable vehicle, e.g., sterile pyrogen-free water, before use.

The pharmaceutical compositions also may comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols.

The agents can be administered by any ordinary route for administering medications. Depending upon the type of cancer to be treated, an agent comprising JFPB, JFPH, and/or functional equivalent and/or anti-cancer antibodies of the invention may be inhaled, ingested or administered by systemic routes. Systemic routes include oral and parenteral. In some embodiments, inhaled medications are preferred because of the direct delivery to the lung, particularly in lung cancer patients. Several types of metered dose inhalers are regularly used for administration by inhalation. These types of devices include metered dose inhalers (MDI), breath-actuated MDI, dry powder inhaler (DPI), spacer/holding chambers in combination with MDI, and nebulizers.

For use in therapy, an effective amount of an agent comprising JFPB, JFPH, and/or functional equivalent can be administered to a subject by any mode that delivers the compound to the affected organ or tissue, or alternatively to the immune system.

The administration route of an agent comprising JFPB, JFPH, and/or functional equivalent and the other agents described herein is not limiting on the administration route of the antibody, antibody fragment or antigen described herein. In some embodiments, an agent comprising JFPB, JFPH, and/or functional equivalent may be administered in the same route, and in the same formulation as the antibody, antibody fragment or antigen. In some embodiments, it may be administered in a different route, different formulation, and even on a different schedule. In some embodiments, an agent comprising JFPB, JFPH, and/or functional equivalent is administered orally, and the antibody, antibody fragment or antigen is administered parenterally, preferably by intramuscular or subcutaneous injection, although it is not so limited.

In some embodiments, the antigens or antibodies are administered mucosally. In these and other embodiments, the subject may be passively or actively exposed to an antigen. Passive exposure occurs when the subject comes in contact with an antigen, such as an infectious pathogen, by being in an environment in which the pathogen is present, and unbeknownst to the subject. Active exposure on the other hand occurs when the subject is deliberately administered an antigen generally for the purpose of vaccination. Passive exposure to infectious pathogens often occurs at the mucosal surfaces such as the oral, nasal, vaginal, penile, and rectal surfaces. Accordingly, the invention embraces exposure of antigens at these surfaces, prior to, substantially simultaneously with, and/or following administration of an agent comprising JFPB, JFPH, and/or functional equivalent.

In some embodiments, it is preferred that antigens and antibodies be administered by routes that mimic the routes through which antigens or carcinogens would enter the body of the subject. For example, if the antigen is from a respiratory virus, then in some embodiments, it is preferable to administer the antigen by inhalation. Similarly, if the antigen is from a microbe that is generally transmitted by sexual intercourse, then, in some embodiments, it is preferable to administer such antigens or antibodies to a vaginal, penile or rectal surface.

In some embodiments, an agent comprising JFPB, JFPH, and/or functional equivalent is administered orally, preferably by ingestible tablets that enter the gastrointestinal tract. In some embodiments, the antigens or antibodies are also administered via the same route. In some instances, it is preferred that an agent comprising JFPB, JFPH, and/or functional equivalent be formulated together with the antigens, and this may be the case particularly in subjects that have or are at risk of developing an infection (e.g. an HIV infection).

In still other embodiments, an agent comprising JFPB, JFPH, and/or functional equivalent is administered locally, and optionally the antigens or antibodies are administered locally as well.

For oral administration, an agent comprising JFPB, JFPH, and/or functional equivalent can be formulated readily by combining the active compound(s) with pharmaceutically acceptable carriers well known in the art. Such carriers enable the compounds of the invention to be formulated as tablets, pills, dragees, capsules, liquids, gels, syrups, slurries, suspensions and the like, for oral ingestion by a subject to be treated. Pharmaceutical preparations for oral use can be obtained as solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate. Optionally the oral formulations may also be formulated in saline or buffers for neutralizing internal acid conditions or may be administered without any carriers.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. Microspheres formulated for oral administration may also be used. Such microspheres have been well defined in the art. All formulations for oral administration should be in dosages suitable for such administration.

For buccal administration, the compositions may take the form of tablets or lozenges formulated in conventional manner.

For administration by inhalation, the compounds for use according to the present invention may be conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g. gelatin for use in an inhaler or insufflator may be formulated containing a powder mix of the compound and a suitable powder base such as lactose or starch. Techniques for preparing aerosol delivery systems are well known to those of skill in the art. Generally, such systems should utilize components which will not significantly impair the biological properties of the therapeutic (see, for example, Sciarra and Cutie, "Aerosols," in Remington's Pharmaceutical Sciences, 18th edition, 1990, pp 1694-1712; incorporated by reference). Those of skill in the art can readily determine the various parameters and conditions for producing aerosols without resort to undue experimentation.

An agent comprising JFPB, JFPH, and/or functional equivalent, when it is desirable to deliver systemically, may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

The compounds may also be formulated in rectal or vaginal compositions such as suppositories or retention enemas, e.g., containing conventional suppository bases such as cocoa butter or other glycerides.

In addition to the formulations described previously, an agent comprising JFPB, JFPH, and/or functional equivalent may be formulated as a depot preparation. Such long acting formulations may be formulated with suitable polymeric or hydrophobic materials (for example as an emulsion in an acceptable oil) or ion exchange resins, or as sparingly soluble derivatives, for example, as a sparingly soluble salt.

Suitable liquid or solid pharmaceutical preparation forms are, for example, aqueous or saline solutions for inhalation, microencapsulated, encochleated, coated onto microscopic gold particles, contained in liposomes, nebulized, aerosols, pellets for implantation into the skin, or dried onto a sharp object to be scratched into the skin. The pharmaceutical compositions also include granules, powders, tablets, coated tablets, (micro)capsules, suppositories, syrups, emulsions, suspensions, creams, drops or preparations with protracted release of active compounds, in whose preparation excipients and additives and/or auxiliaries such as disintegrants, binders, coating agents, swelling agents, lubricants, flavorings, sweeteners or solubilizers are customarily used as described above. The pharmaceutical compositions are suitable for use in a variety of drug delivery systems. For a brief review of methods for drug delivery, see Langer, Science 249:1527-1533, 1990, which is incorporated herein by reference.

In some important embodiments, the timing of administration of an agent comprising JFPB, JFPH, and/or functional equivalent and the antigen are important. Thus, the invention embraces the administration of an agent comprising JFPB, JFPH, and/or functional equivalent, preferably with an antigen, prior to treatment with other conventional therapy. For example, if the subject has cancer, then conventional therapy includes surgical removal of a tumor, radiation therapy, or chemotherapy. It is preferred in some instances to administer an agent comprising JFPB, JFPH, and/or functional equivalent with antigen prior to this therapy, and even more preferred to administer an agent comprising JFPB, JFPH, and/or functional equivalent with antigen after this therapy as well. Thus, the method would involve both a prime and a boost dose to antigen (i.e., with an agent comprising JFPB, JFPH, and/or functional equivalent). In some embodiments, the antigen alone can be administered particularly in the boost dose.

In some embodiments, the antibody or antibody fragment may be administered together with an agent comprising JFPB, JFPH, and/or functional equivalent in a multi-day cycle. The multi-day cycle be a 2, 3, 4, 5, 6, 7, 8, 9, 10, or more day cycle. The antibody or fragment thereof may be administered on the first day of such a cycle, followed by administration of t an agent comprising JFPB, JFPH, and/or functional equivalent for a number of days, which may or may not be consecutive. For example, an agent comprising JFPB, JFPH, and/or functional equivalent may be administered on all remaining days of a multi-day cycle. An agent comprising JFPB, JFPH, and/or functional equivalent may be administered once, twice, three, or more times per day as well. The multi-day cycle may be repeated once, twice, three, or more times. Alternatively, it may be repeated for a length of time such as a week, a month, two months, or more, depending upon the status of the subject and the therapeutic response observed. As a non-limiting example, the antibody or fragment thereof is administered on the first day of a seven day cycle, and an agent comprising JFPB, JFPH, and/or functional equivalent is administered twice a day for the remaining six days of the seven day cycle. The seven day cycle is performed four times resulting in a 28 day treatment.

The invention further provides kits (e.g., pharmaceutical preparations) that minimally comprise the agents of the invention. In some embodiments, the kit comprises an agent comprising JFPB, JFPH, and/or functional equivalent. In some embodiments, the kit comprises in one container an antibody or antibody fragment, preferably formulated and contained for administration by injection, and in another container an agent comprising JFPB, JFPH, and/or functional equivalent (e.g., formulated for oral administration (e.g., as a tablet)). As another example, the kits may comprise in one container both an agent comprising JFPB, JFPH, and/or functional equivalent and an antigen, or a cocktail of antigens. Alternatively, an agent comprising JFPB, JFPH, and/or functional equivalent and the antigens may be provided in the same kit but in different containers, and in different formulations for different administration routes. In some embodiments, it is preferred to provide all the active agents in a powdered form such as a lyophilized form that can be reconstituted prior to administration to a subject. All the kits of the invention can optionally contain instructions for storage, reconstitution (if applicable) and administration.

EXPERIMENTAL

The following examples are provided in order to demonstrate and further illustrate certain preferred embodiments and aspects of the present invention and are not to be construed as limiting the scope thereof.

Example 1

Identification of Small Molecules Capable of Altering CD154 Function

Hundreds of thousands of small molecules were screened for their ability to stabilize CD154 trimer activity on the cell surface, or in soluble form. Specifically, a suitable pocket for targeting the small molecule was identified and computer modeling carried out in order to identify candidate molecules from roughly 250,000 small molecules/chemicals. A theoretical molecular model of the functional homotrimeric murine CD154 protein complex was obtained from the NIH Center for Molecular Modeling database (PDB theoretical model code 1 CDA) and compared to that of the human CD154 crystallographic structure (PDB code 1ALY). Analysis demonstrated very high homology between the mouse and human structures at primary, secondary and tertiary levels. The model was then analyzed for a suitable site for docking studies. For evaluation and docking purposes, each of the three chains of the homotrimer was designated specific residue numbers. Thus, each residue in each chain possessed an identifying number code: chain 1 (residues assigned numbers 1-146), chain 2 (residues assigned numbers 147-292) and chain 3 (residues assigned numbers 293-438). The residues determined to define the binding site for stabilization of the trimer are listed in Table 1, below. The putative binding site is shown in FIG. 1(a).

TABLE 1

Residues in each homotrimeric complex CD154 chain used to define the binding site for trimer stabilization.

| Chain 1 | | Chain 2 | | Chain 3 | |
|---|---|---|---|---|---|
| Amino Acid Residue | Number Code | Amino Acid Residue | Number Code | Amino Acid Residue | Number Code |
| ASP | 2 | ASP | 150 | GLN | 298 |
| GLU | 3 | GLN | 152 | ARG | 342 |
| ASP | 4 | ARG | 196 | | |
| GLN | 6 | LEU | 292 | | |
| ARG | 50 | | | | |
| LYS | 145 | | | | |
| LEU | 146 | | | | |

Computerized docking screens were carried out using this binding site to screen 250,000 small molecules/chemicals from the available chemicals directory (See, e.g., ACD, at http://cds.dl.ac.uk/cds/help/acdmovies.html). Parameters were set in order to find compounds that would function to stabilize the three chains that form the functional CD154 homotrimer. C-Dock software was used to calculate stabilizing compounds and affinities were used to score each compound in the ACD.

FIG. 1(a) depicts the binding site that was targeted (arrow). This site is only present in the trimer form of CD154, as it forms a 'pocket' at the interface of the three CD154 chains. Each CD154 chain of the trimer is identified. The binding site is more fully described by residue in Table 1. FIG. 1(b) is but one example of a docked chemical from the top 500 scored ACD list after computerized screening was carried out. The lines leading from the chemical, shown in its most stable orientation within the binding site as determined by C-Dock software, are polar interactions accessible to the binding site.

The top 500 compounds were then screened visually to select the top compounds for in vitro screening. An example of this screen is demonstrated in FIG. 1(b), wherein one of the top 500 small molecules is shown docked into the binding site described in Table 1. Upon manual screening of the top 500 scored compounds, 25 were selected for biological screening. Of the 25 compounds, 18 were commercially available and purchased for experimentation.

Example 2

Establishing an in vitro Biologic Screen for Candidate Small Molecules

The initial biological screen for the selected small molecule compounds was based in functional characteristics of enhancement of Th1 function and secretion of Th1 cytokines (e.g., Interferon-γ (IFN-γ)). In this process, dendritic cells (DC) were obtained by GM-CSF stimulation of bone marrow stem cells for 6 days, pulsed for 18 hours with $OVA_{323-339}$ peptide to load specific antigen on these antigen presenting cells and then purified using CD11c magnetic bead separation. This population of cells is routinely >98% CD11c positive, as determined by flow cytometry. Transgenic T cells with specificity for the ovalbumin 323-339 epitope ($OVA_{323-339}$) were obtained from naïve spleens of DO11.10 transgenic mice. The splenic cells were harvested and magnetic beads used to isolate the CD4 T cell population. This latter population of cells is routinely >95% $CD4^+$. The cells were then co-cultured in round-bottomed 96 well tissue culture plates, at varying ratios, maintaining $2 \times 10^5$ $CD4^+$ T cells in each well, and varying the number of dendritic cells added (See FIG. 2).

As shown in FIG. 2(a), co-culture of peptide-pulsed DC and DO11.10 transgenic T cells proliferation peaked on days 4 and 5. FIG. 2(b) shows that this proliferative response was determined by the optimal ratio of T cells:DC, with a useful range of 16 to 256:1, with T cells remaining constant and diminishing DC additions. As shown in FIG. 2(c), the induction of the response is dependent upon $OVA_{323-339}$ peptide, and is therefore antigen-specific, since an irrelevant peptide loaded population of DC did not induce DO11.10 T cell proliferation.

Figure 2:
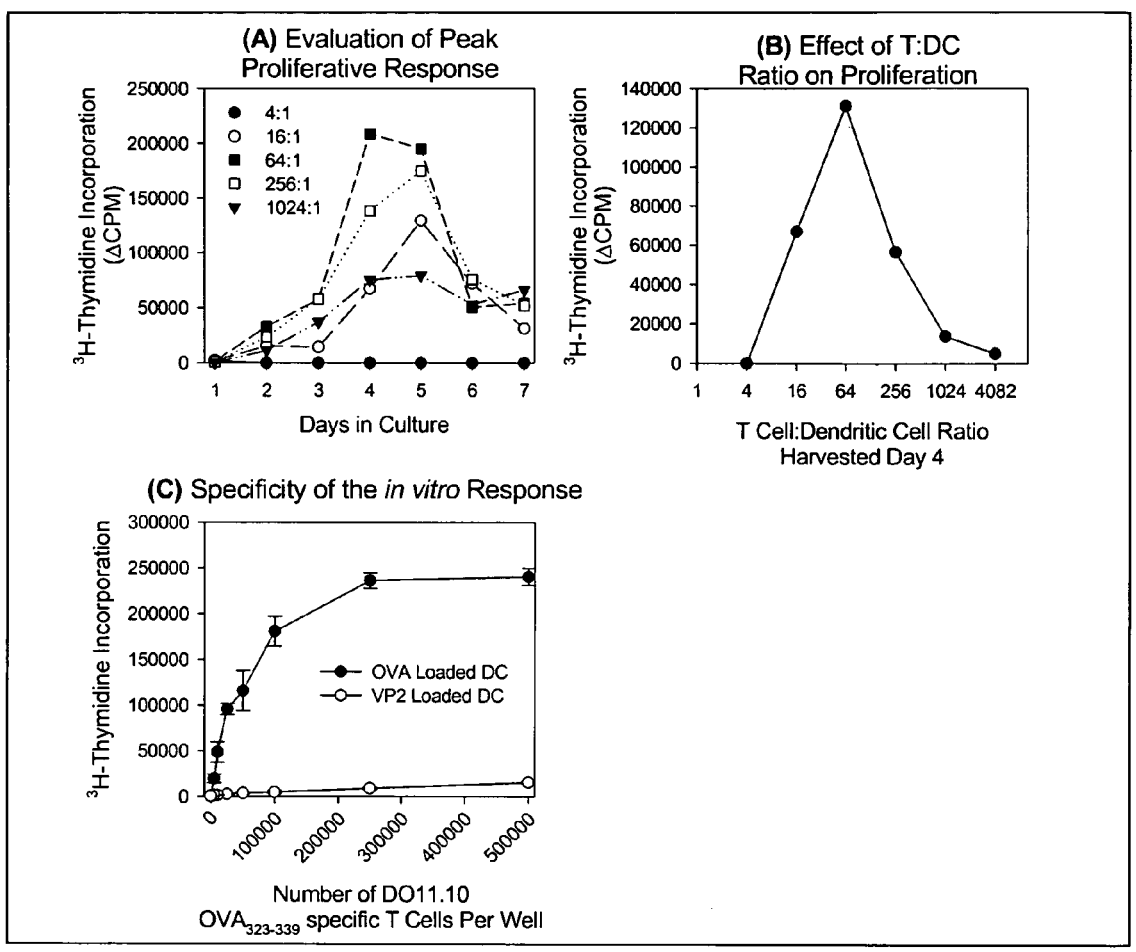
FIG. 2 shows results of the in vitro Screening Assay.
Figure 3:
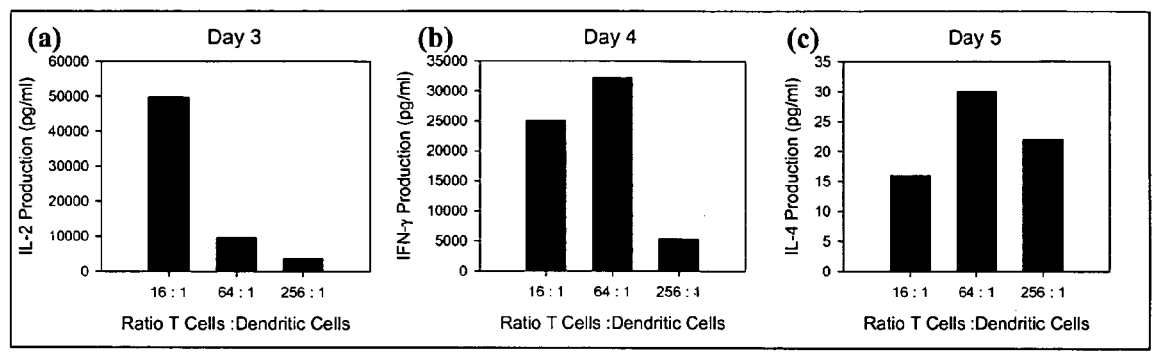
FIG. 3 shows low T:DC Ratios bias Type 2 Responses whereas high ratios promote IFN-γ Secretion.

As shown in FIG. 2, the co-culture system is antigen-specific and the peak response by proliferation was determined on days 4 and 5. In addition, the ratio of CD4 T cells to dendritic cells (T:DC) plays a critical role in defining the efficiency of the induced T cell response. At very high DC ratios (e.g., 4:1) the T cell response failed to occur. From 16:1 to 256:1, the proliferative response reached its peak, and diminished as fewer DC were added to the wells. This ratio effect was predicted to also influence cytokine production. As shown in FIG. 3, cytokine production was dependent on the strength of T cell engagement by DC, since modification of the ratios dramatically changed the cytokine response. IL-2 secretion was determined to be optimal on day 3, while IFN-γ and IL-4 secretion were optimal on days 4 and 5, respectively. Thus, at a 16:1 and 64:1 ratio, Type 1 responses (as determined by IL-2 and IFN-γ secretion) were optimal, with very high IL-2 secretion seen at 16:1 ratios. The ratio of cells did not appear to affect IL-4 secretion, to any large extent, since optimal secretion was seen at 64 and 256:1 ratios, however, IFN-γ secretion was shown to be markedly reduced at 256:1 ratios. It was predicted that at a 256:1 ratio, where competition for TCR engagement with limited APC presentation is high, Type 1 responses would be low and a bias seen towards that of a Type 2 response (IL-4).

Thus, this in vitro system demonstrates an excellent screen for molecules whereby it is possible to evaluate the enhancement of Type 1 responses over that of Type 2 responses, at lower ratios of T:DC. For example, if the small molecules work through CD154 stabilization, the proliferative response should remain comparable between groups, but the IFN-γ secretory response should be augmented. As the ratio of T:DC are reduced, this should increase such enhancement as Type 1 responses would otherwise be suboptimal, as discussed below.

Example 3

In vitro Testing of Candidate Small Molecule Compounds

The in vitro screen for functional activity was based on two parameters. The first parameter, $^3$H-thymidine incorporation measuring proliferation of $OVA_{323-339}$-peptide-specific DO11.10 T cells cultured in the presence of $OVA_{323-339}$-peptide pulsed GM-CSF derived dendritic cells, should not be affected by CD154-CD40 interactions, and thus was used as a screen for non-specific toxicity of the compounds to immune cell co-cultures. The second parameter, which is controlled in the DO11.10 T cell —$OVA_{323-339}$-peptide loaded dendritic cell co-cultures by CD40 ligation, is that of Interferon-γ secretion by the activated T cells.

Blockade of the CD154-CD40 interactions, or elimination of the CD154-CD40 ligand pair interactions, has been shown to eliminate IFN-γ secretion, in vitro. Thus, it was hypothesized that if it was possible to enhance immune function by stabilization of CD154-CD40 ligand pair interactions through prolonged stability of CD154 homotrimers, then IFN-γ production should be increased by addition of the small molecule compounds. Thus, by screening out compounds that inhibited T cell proliferation and identifying only compounds that did not significantly affect T cell proliferation while specifically augmenting IFN-γ production, the inventors sought to ensure that a) the specificity of the response is to that which the assay is designed, b) compounds with toxic effects were quickly eliminated from the screen, and c) enhancement of CD40 dependent events would be identified.

An initial screen was carried out with 18 compounds, using the in vitro screening process established in Example 2, above. Initially, all 18 compounds were evaluated for toxicity at 5 mM and 0.1 µM, by evaluation of proliferation of 16:1 and 64:1 ratio T:DC co-cultures. Second, expression of IFN-γ was observed and compared to that of control samples. Of the initial 18 small molecule compounds, 5 compounds were eliminated at this early stage because they inhibited T cell proliferation and were toxic to the cells in culture. Two of the 18 small molecule compounds were identified that consistently enhanced IFN-γ secretion in these cultures, but had no effect on T cell proliferation. These two compounds, JFPH and JFPB, were selected for further study, as described below.

Example 4

Characterization of Two Small Molecule Compounds

Figure 4:
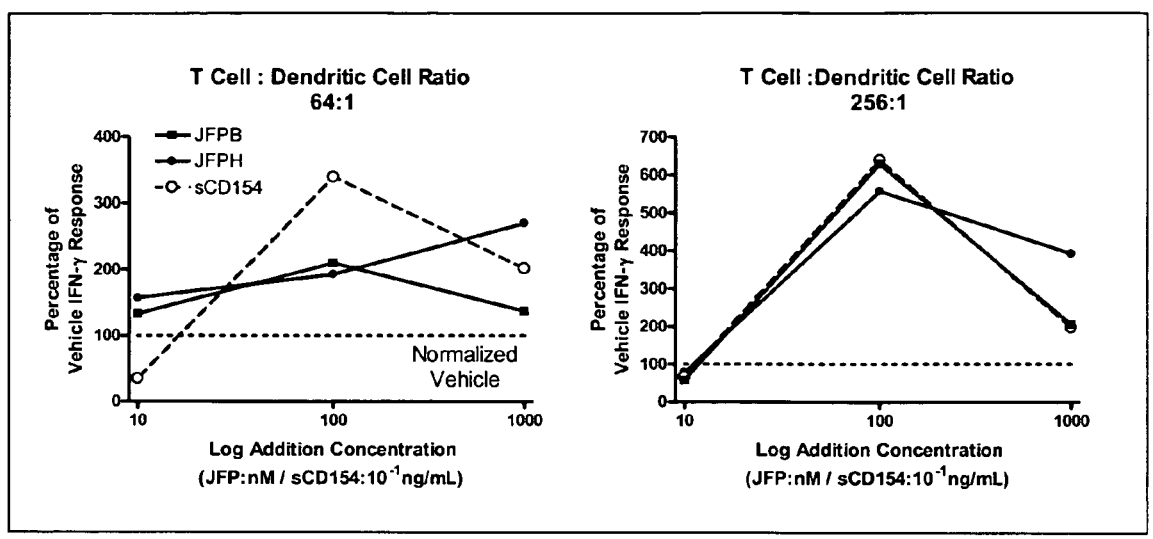
FIG. 4 depicts the titration of IFN-γ response by two small molecule compounds, JFPB and JFPH.

At an optimal Type 1 induction of IFN-γ secretion (e.g., at a 64:1 ratio, there was at least a 2 fold increase in IFN-γ production (See FIG. 4, left panel). In addition, this enhancement titrated with the reduction in concentration of the compounds. At the highest concentration, enhancement was observed with JFPH, while JFPB and control sCD40L trimers demonstrated reduced IFN-γ enhancement (1000 ng/ml and 100 ng/ml, respectively). sCD40L trimers were added as a positive control.

Small molecules in DMSO vehicle were added at various dilutions to co-cultures of DC-T cells and after four days supernatants characterized for the production of IFNγ. As shown in the FIG. 4, left panel, at 64:1, where responses are optimal, little difference was seen over that of the control vehicle response. By contrast, in FIG. 4, right panel, where the environment is not conducive to IFN-γ production, the addition of small molecules demonstrated enhancement of IFN-γ secretion. In each case, soluble CD154 trimers were used as a positive control.

The physiologic process that appears stabilized by the two small molecule compounds was consistent across experiments. The 2 fold increase in IFN-γ secretion seen at the 64:1 ratio was quite small, since this ratio produced optimal levels of IFN-γ secretion already (FIG. 3). The fact that even then some enhancement occurred suggests that CD154-CD40 interactions are still limiting in these cultures, particularly since sCD40L had a dramatic enhancing effect on this response. Given that the small molecules should enhance suboptimal Type 2 responses and push them towards a Type 1 response, the 256:1 ratio, which is a Type 2 response (See, e.g., FIG. 3), demonstrated far more enhancement of IFN-γ secretion (FIG. 4, right panel), compared to that of the vehicle control. The two selected small molecules acted in a very similar fashion to that of the sCD40L positive control. At a 1100 nM concentration, IFN-γ secretion was augmented approximately 6 fold, reaching the levels of the Th1 responses in the 64:1 ratio co-cultures. Thus, the small molecules appear to enhance Type 1 responses similarly to that of sCD40L trimers from an otherwise normal Type 2 response.

Example 5

Identification of Functionally Equivalent Small Molecules

The two compounds identified that stabilized CD154 trimer expression by T cells were JFPB (ethyl N-[[1-(2-[[3-chloro-5-(trifluoromethyl)-2-pyridinyl]amino]ethyl]-2,4-dioxo-1,2,3,4-tetrahydro-5-pyrimidinyl]carbonyl]carbamate (See, e.g., Bionet Research Limited, England, product code 3G-960) and JFPH (4-azocan-1-YL-5,7-dichloro-2-(trifluoromethyl)quinoline (See, e.g., Maybridge International Limited, England, product code KM10695). Using a Tanimoto similarity search, compounds with high amounts of similarity to the two identified compounds were identified. Twenty-seven compounds were identified based on a Tanimoto score >0.6. These compounds are identified in Table 2 and are depicted below. As described herein, these compounds find use in the compositions and methods of the present invention.

TABLE 2

ACD2003.2 Hit list of compounds scoring >0.6 Tanimoto score for similarity to JFPB and JFPH. 2.35 million compounds in this database were screened.

| MFC | Manufacturer | Tanimoto score |
| --- | --- | --- |
| MFCD00069852 | RBI-LOPAC | 0.61 |
| MFCD00160647 | SALOR | 0.65 |
| MFCD00172969 | AMBRINTER/BIONET/INTRCHM-SC | 0.81 |
| MFCD00172995 | AMBRINTER/BIONET/INTRCHM-SC | 0.77 |
| MFCD00172996 | AMBRINTER/BIONET/INTRCHM-SC | 1.00 |

TABLE 2-continued

ACD2003.2 Hit list of compounds scoring >0.6 Tanimoto score for similarity to JFPB and JFPH. 2.35 million compounds in this database were screened.

| MFC | Manufacturer | Tanimoto score |
| --- | --- | --- |
| MFCD00179472 | MAYBRIDGE | 0.61 |
| MFCD00264882 | XSCIEXCH | 0.62 |
| MFCD00264930 | XSCIEXCH | 0.62 |
| MFCD00265045 | XSCIEXCH | 0.61 |
| MFCD00274875 | MAYBRIDGE | 0.63 |
| MFCD00662110 | MAYBRIDGE | 0.62 |
| MFCD00662186 | MAYBRIDGE | 0.76 |
| MFCD00662188 | MAYBRIDGE | 0.64 |
| MFCD00662191 | MAYBRIDGE | 0.68 |
| MFCD00662213 | MAYBRIDGE | 0.67 |
| MFCD00663780 | AMBRINTER/BIONET/INTRCHM-SC | 0.70 |
| MFCD00793042 | AMBRINTER/BIONET/INTRCHM-SC | 0.72 |
| MFCD00793045 | AMBRINTER/BIONET/INTRCHM-SC | 0.60 |
| MFCD00793049 | AMBRINTER/BIONET/INTRCHM-SC | 0.64 |
| MFCD01465738 | INTRCHM-SC/SPECS-SC | 0.62 |
| MFCD01468770 | CHEMBRIDGE | 0.60 |
| MFCD01469511 | CHEMBRIDGE | 0.70 |
| MFCD01566485 | MAYBRIDGE | 0.67 |
| MFCD01566499 | MAYBRIDGE | 0.60 |

Structures of the small molecule compounds listed in Table 2:

MFCD00172969

5-Acetyl-1-[2-(3-chloro-5-trifluoromethyl-pyridin-2-ylamino)-ethyl]-1Hpyrimidine-2,4-dione

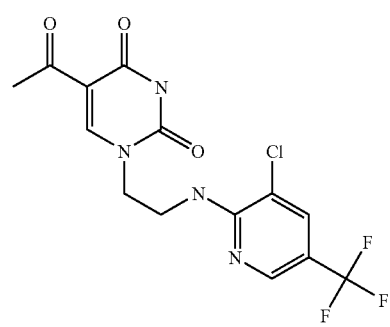

MFCD00172995

5-acetyl-1-[2-[[3-chloro-5-(trifluoromethyl)-1H-pyrid-2-yl]amino]ethyl]-1H-pyrimidine-2,4-dione

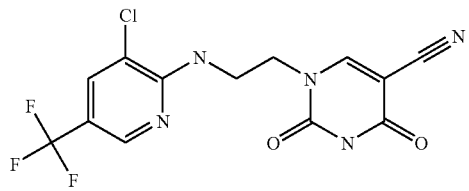

MFCD00172996

[1-[2-(3-Chloro-5-trifluoromethyl-pyridin-2-ylamino)-ethyl]-2,4-dioxo-1,2,3,4-tetrahydro-pyrimidine-5-carbonyl]-carbamic acid ethyl ester

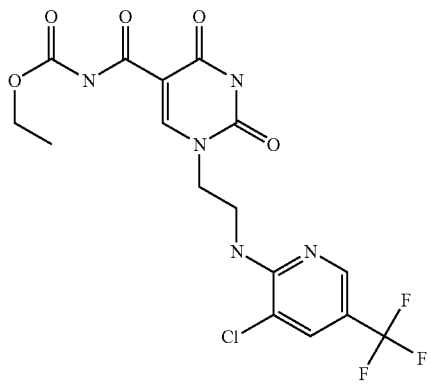

MFCD00179472

[2,4-Dioxo-1-(2-pyridin-4-yl-ethyl)-1,2,3,4-tetrahydro-pyrimidine-5-carbonyl]-carbamic acid ethyl ester

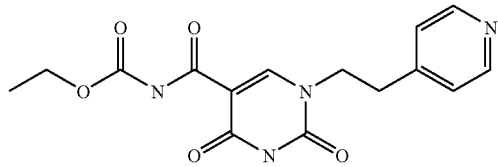

MFCD00264930

Cyclohexanecarboxylic acid (2-methyl-quinolin-4-yl)-amide

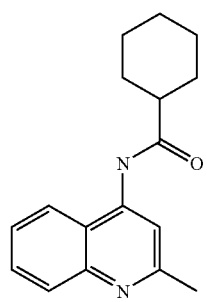

MFCD00274875

4-(2-Trifluoromethyl-quinolin-4-yl)-piperazine-1-carboxylic acid(3,5-dichloro-phenyl)-amide

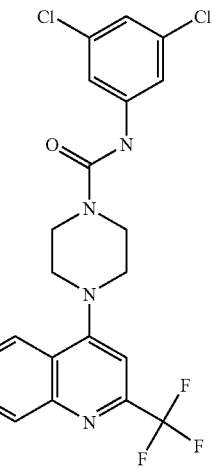

MFCD00662110

1-[4-(2-Trifluoromethyl-quinolin-4-yl)-piperazin-1-yl]-ethanone

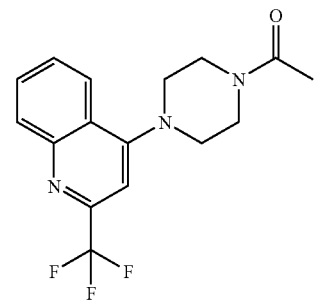

MFCD00662186

8-Chloro-4-piperidin-1-yl-2-trifluoromethyl-quinoline

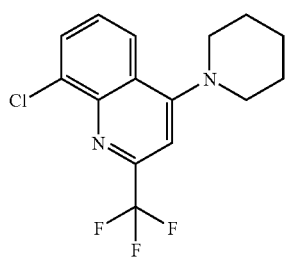

MFCD00662188

8-Chloro-4-morpholin-4-yl-2-trifluoromethyl-quinoline

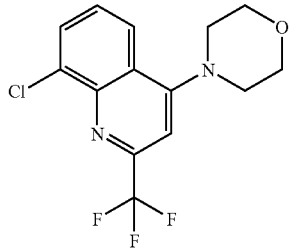

MFCD00662191

4-(4-Benzhydryl-piperidin-1-yl)-8-chloro-2-trifluoromethyl-quinoline

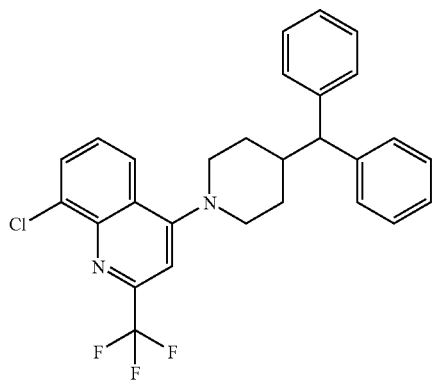

MFCD00662213

1-(8-Chloro-2-trifluoromethyl-quinolin-4-yl)-piperidine-4-carboxylicacid ethyl ester

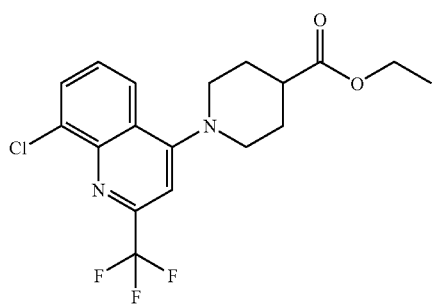

MFCD00663780

1-[2-(3-Chloro-5-trifluoromethyl-pyridin-2-ylamino)-ethyl]-6-methyl-4-oxo-1,4-dihydro-pyrimidine-5-carbonitrile

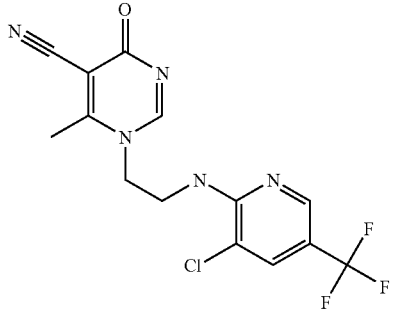

MFCD00793042

6-Chloro-3-[2-(3-chloro-5-trifluoromethyl-pyridin-2-ylamino)-ethyl]-1Hpyrimidine-2,4-dione

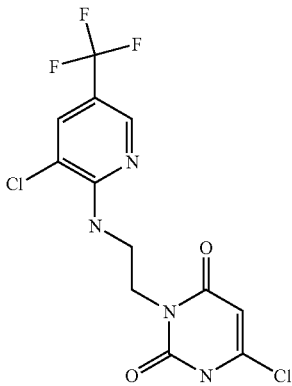

MFCD00793045

3-[2-(3-Chloro-trifluoromethyl-pyridin-2-ylamino)-ethyl]-6-(pyridin-2-ylsulfanyl)-1H-pyrimidine-2,4-dione

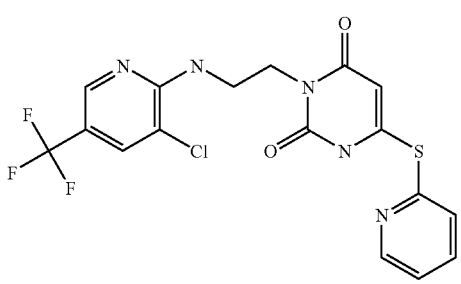

MFCD00793049

3-[2-(3-Chloro-5-trifluoromethyl-pyridin-2-ylamino)-ethyl]-6-(pyrimidin-2-ylsulfanyl)-1H-pyrimidine-2,4-dione

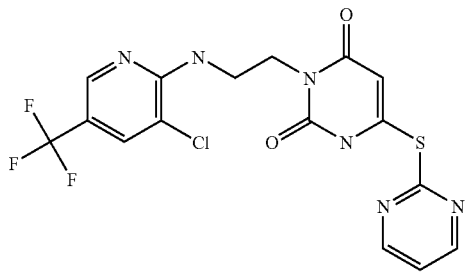

MFCD01465738

[1-[2-(2-Hydroxy-ethylamino)-ethyl]-2,4-dioxo-1,2,3,4-tetrahydro-pyrimidine-5-carbonyl]-carbamic acid ethyl ester

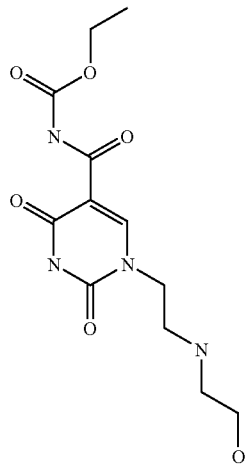

MFCD01468770

(7-Chloro-4-methyl-quinolin-2-yl)-cycloheptyl-amine288.8200

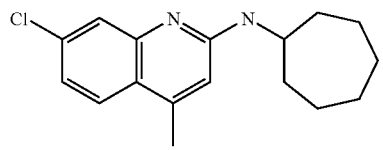

MFCD01469511

7-Chloro-4-methyl-2-perhydro-azocin-1-yl-quinoline

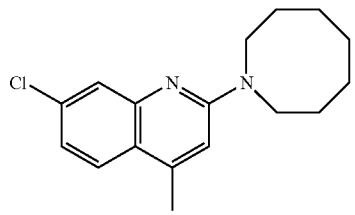

MFCD01566485

2-[Methyl-(2-trifluoromethyl-quinolin-4-yl)-amino]-ethanol

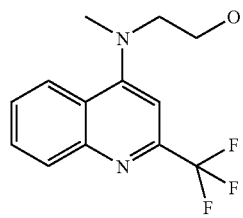

MFCD01566499

(4-Chloro-phenyl)-carbamic acid2-[methyl-(2-trifluoromethyl-quinolin-4-yl)-amino]-ethyl ester

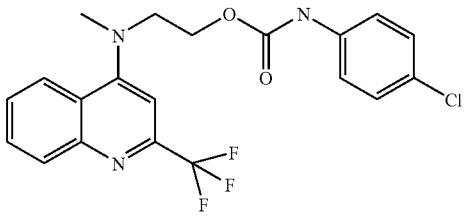

The present invention is not limited to the specifically recited compounds. Indeed, the present invention contemplates the administration of suitable isomers, enantiomers, racemic compounds, metabolites, derivatives, and/or pharmaceutically acceptable salts (e.g., in combination with acids or bases) and the like. The present invention also encompasses prodrugs comprising the compounds of the present invention.

As used herein, the term "derivative" of a compound refers to a chemically modified compound wherein the chemical modification takes place either at a functional group of the compound, aromatic ring, or carbon backbone. Such derivatives include esters of alcohol-containing compounds, esters of carboxy-containing compounds, amides of amine-containing compounds, amides of carboxy-containing compounds, imines of amino-containing compounds, acetals of aldehyde-containing compounds, ketals of carbonyl-containing compounds, and the like.

As used herein the term "prodrug" refers to a pharmacologically inactive derivative of a parent "drug" molecule that requires biotransformation (e.g., either spontaneous or enzymatic) within the target physiological system to release, or to convert (e.g., enzymatically, mechanically, electromagnetically, etc.) the "prodrug" into the active "drug." "Prodrugs" are designed to overcome problems associated with stability, toxicity, lack of specificity, or limited bioavailability. Exemplary "prodrugs" comprise an active "drug" molecule itself (e.g., the compounds of the present invention) and a chemical masking group (e.g., a group that reversibly suppresses the activity of the "drug"). Some preferred "prodrugs" are variations or derivatives of compounds that have groups cleavable under metabolic conditions. Exemplary "prodrugs" become pharmaceutically active in vivo or in vitro when they undergo solvolysis under physiological conditions or undergo enzymatic degradation or other biochemical transformation (e.g., phosphorylation, hydrogenation, dehydrogenation, glycosylation, etc.). Prodrugs often offer advantages of solubility, tissue compatibility, or delayed release in the mammalian organism. (See e.g., Bundgard, Design of Prodrugs, pp. 7-9, 21-24, Elsevier, Amsterdam (1985); and Silverman, The Organic Chemistry of Drug Design and Drug Action, pp. 352-401, Academic Press, San Diego, Calif. (1992)). Common "prodrugs" include acid derivatives such as esters prepared by reaction of parent acids with a suitable alcohol (e.g., a lower alkanol), amides prepared by reaction of the parent acid compound with an amine (e.g., as described above), or basic groups reacted to form an acylated base derivative (e.g., a lower alkylamide).

Example 6

In Vivo Testing of the Small Molecule Compounds

Experiments were conducted to confirm that the small molecules could stabilize and therefore enhance Th1 effector function in vivo. Efficacy was tested in a mouse model of experimental autoimmune encephalomyelitis (EAE), a model of Multiple Sclerosis (MS) (See, e.g., Karlsson et al., The Journal of Immunology, 2003, 170: 1019-1026).

EAE is dependent upon CD154-CD40 interactions in the central nervous system (CNS). Initial experiments were carried out to determine the effects of these small molecules on clinical disease severity in an optimal process of induction of EAE. The compounds should not modify the severity of clinical disease over that of the vehicle control treated animals, but enhancement and prolonged Th1 responses peripherally may be observed. Second, experiments were conducted to address whether the severity and/or incidence of EAE disease could be enhanced by the small molecule therapy in mice immunized with suboptimal myelin antigenic peptide, such that the small molecules might enhance in vivo functional activity of the antigen specific Th1 cells induced in these mice, that normally would have low incidence and severity of clinical disease.

Figure 5:
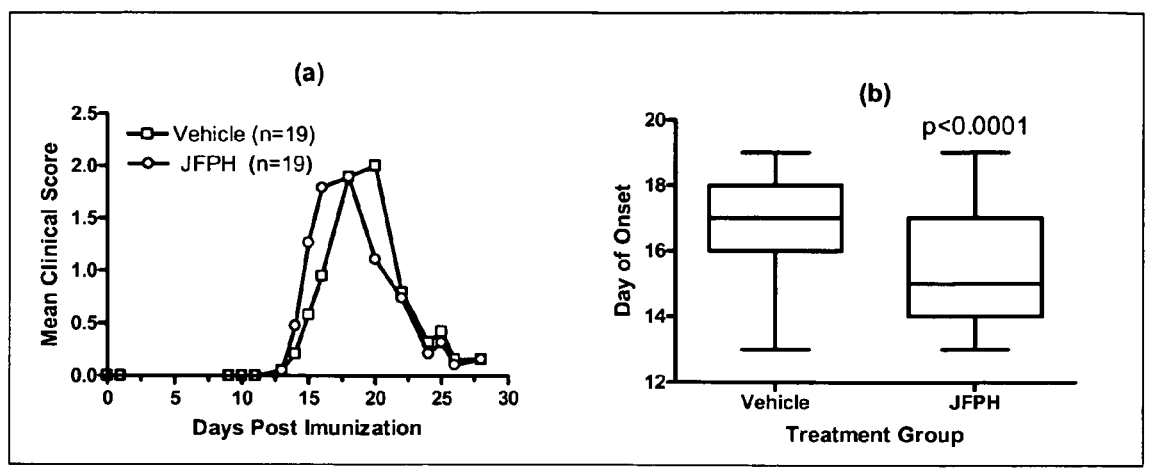
FIG. 5 shows that JFPH accelerated disease onset in EAE mice induced under optimal conditions.

Mice were immunized with $PLP_{139-151}$-peptide in CFA and treated on days 9 and 10 with 100 nmol JFPH in olive oil or vehicle alone. Clinical disease was then evaluated. Clinical severity was assessed on a 0 to 5 scale as follows: grade 1, limp tail; grade 2, limp tail and hind limb weakness (waddling gait); grade 3, partial hind limb paralysis; grade 4, complete hind limb paralysis; and grade 5, moribund. The data are plotted as the daily mean clinical score for all animals in a particular treatment group, and mean day of onset for each mouse was determined and plotted (See, FIG. 5(b)) as a box and whisker plot. When optimal EAE induction was carried out using 50 μg doses of $PLP_{139-151}$ peptide, disease severity was not affected by treatment with 100 nmol JFPH on days 9 and 10 post-immunization. However, the mean day of disease onset was earlier in the JFPH treated mice compared to vehicle controls (p<0.0001) as determined by a Wilcoxon Sign-Rank test. While vehicle mean day of onset was 16.68±1.60 (standard deviation), JFPH treated mice had a mean day of onset of 15.47±1.68 (See, FIG. 5).

Figure 6:
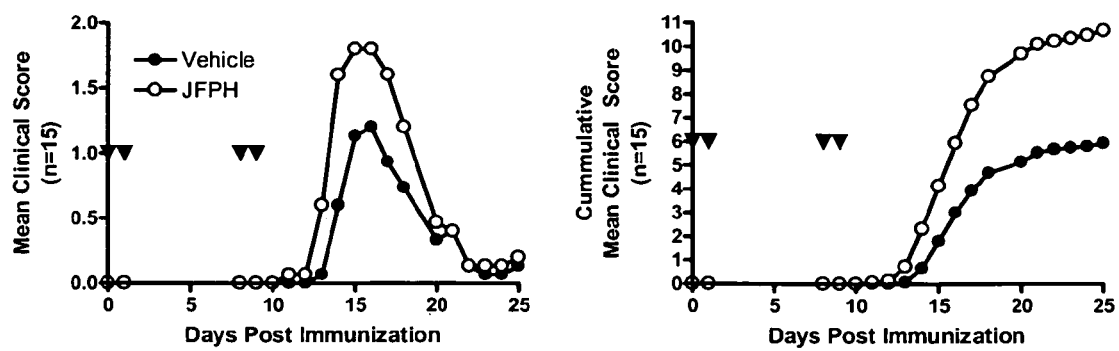
FIG. 6 shows that JFPH accelerated disease onset in EAE mice induced under suboptimal conditions.

In experiments where suboptimal induction of EAE was induced with 25 μg doses of $PLP_{139-151}$ peptide, the incidence of disease was low for vehicle treated mice (60%) compared to that of JFPH treated mice (100%). Briefly, mice were immunized with 25 μg $PLP_{139-151}$-peptide in CFA and treated on days 0, 1, 8 and 9 with 100 nmol JFPH in olive oil or vehicle of olive oil alone (FIG. 6, treatment days marked by downward triangles). Clinical disease was evaluated and the cumulative mean clinical scores determined by addition of scores cumulatively with each subsequent day of evaluation (FIG. 6, right panel). The average maximum score for vehicle treated mice was 1.2 (due in part to one individual mouse) versus 1.8 for JFPH treated mice, and in both mean day of onset and mean day of peak disease severity, the JFPH treated mice reached these time points an average of 3 days earlier than that of vehicle treated mice. There was no difference in the mean day of remission (defined by a reduction of one full score for two days), indicating that disease course was an average of 3 days longer for JFPH treated versus vehicle alone control treated groups.

Example 7

Characterization of JFPH Treatment in a Murine Tumor Model

In order to evaluate the efficacy of JFPH in a murine tumor model, Balb/c mice were first injected with syngeneic renal cell carcinoma (RCC) cells. The injections were delivered either sub-cutaneously or orthotopically under the kidney capsule (intra-renal). JFPH drug was diluted in olive oil to a desired concentration. Mice were injected with JFPH in olive oil intra-peritoneally 3×/week for a total of 3 weeks, beginning on day 3 post-tumor cell injection. As a vehicle control, mice were administered with only olive oil (no JFPH). For the sub-cutaneous tumor model, primary tumors were measured with calipers 3×/week and the tumor area was calculated. For the intra-renal tumor model, mice were euthanized on day 21 post tumor-cell injection and the lungs were harvested and placed in fixative. The number of lung metastases were then counted under a dissecting microscope.

Figure 7:
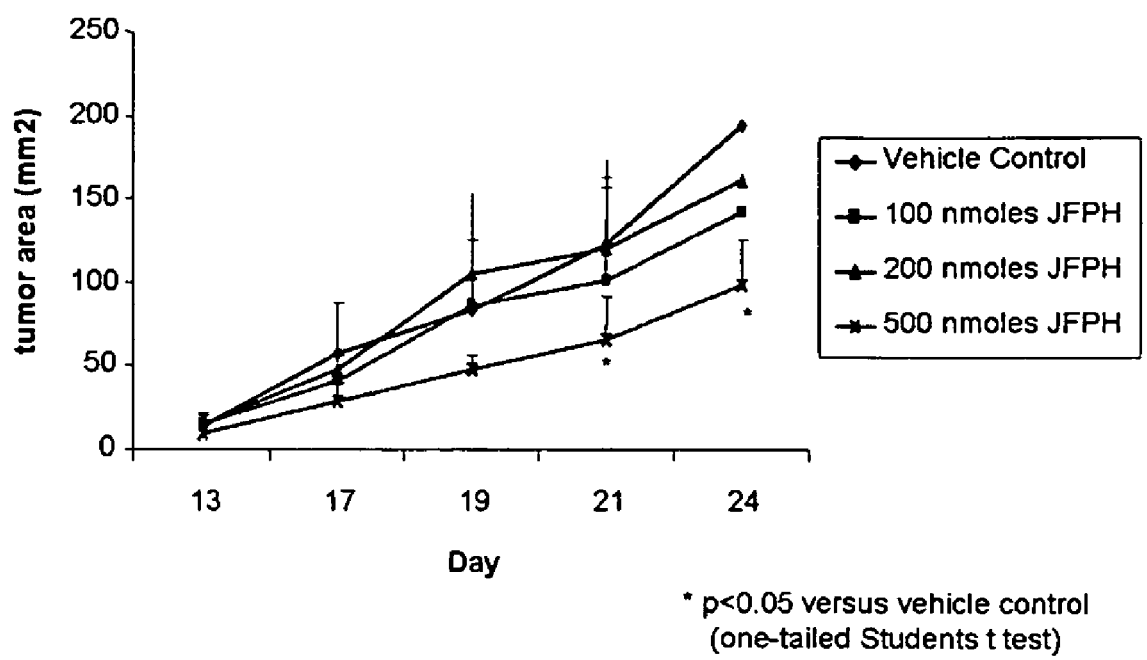
FIG. 7 shows that treatment of mice with JFPH delays sub-cutaneous growth of renal cancer.
Figure 8:
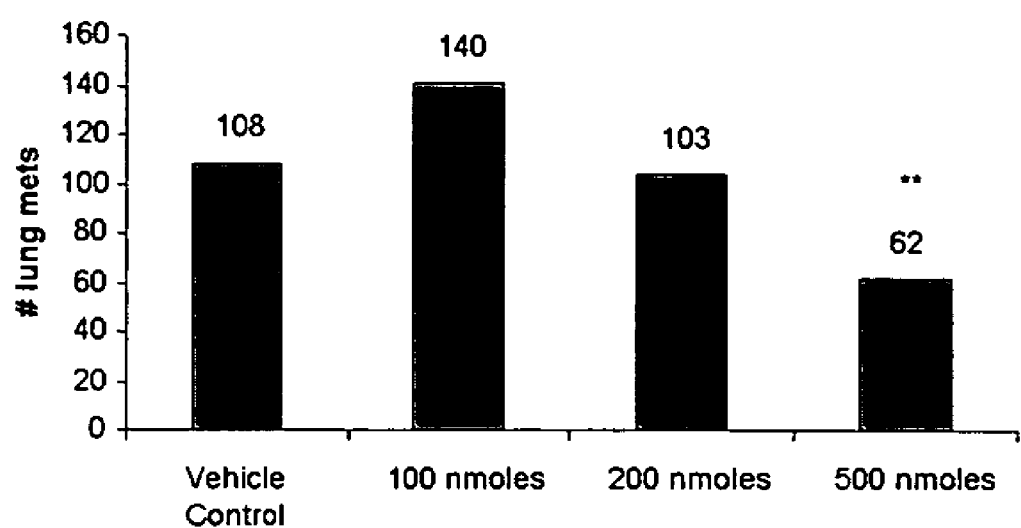
FIG. 8 shows that treatment of mice with JFPH reduces renal cancer metastasis.
Figure 9:
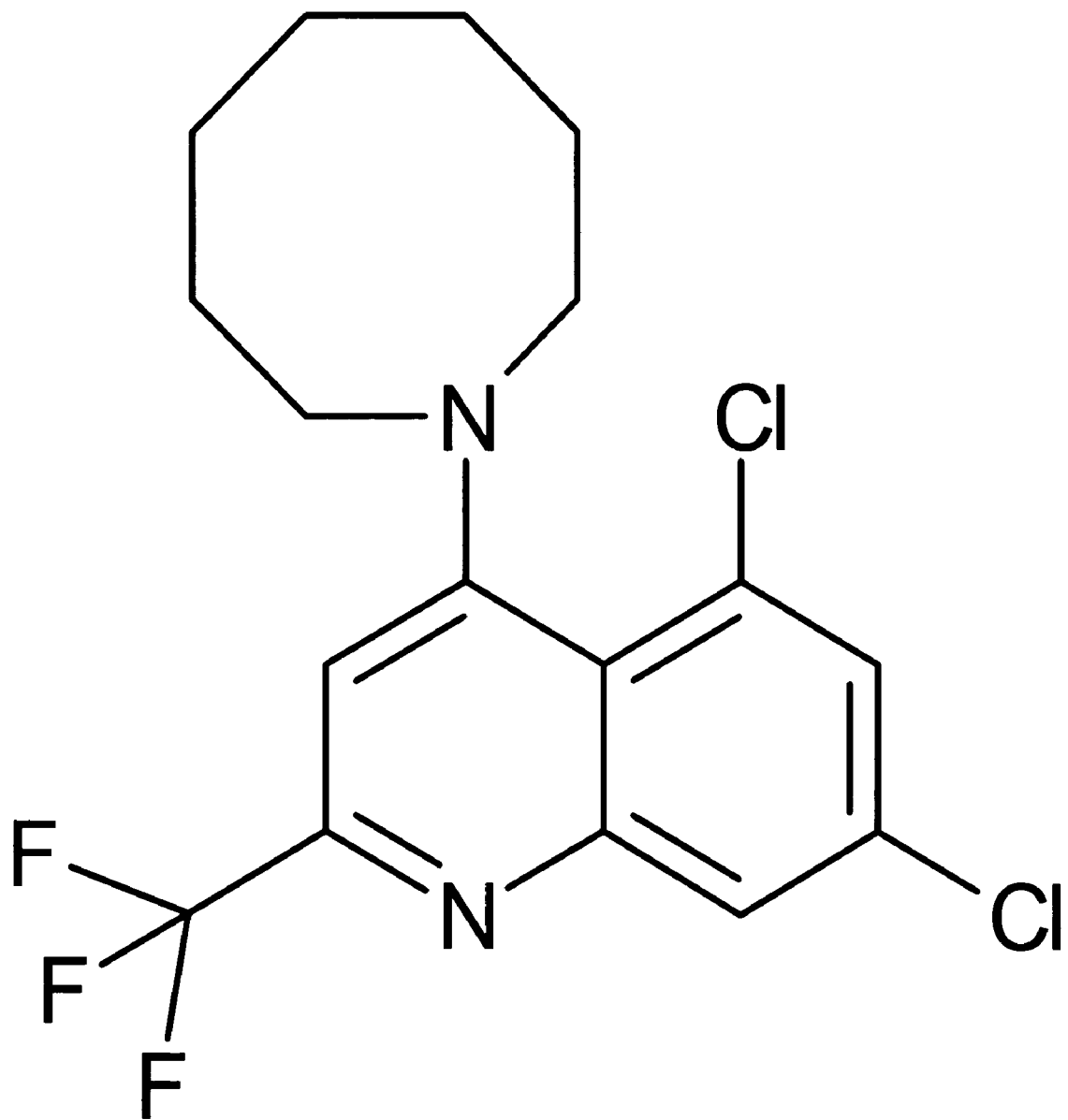
FIG. 9 shows the structure of JFPH.
Figure 10:
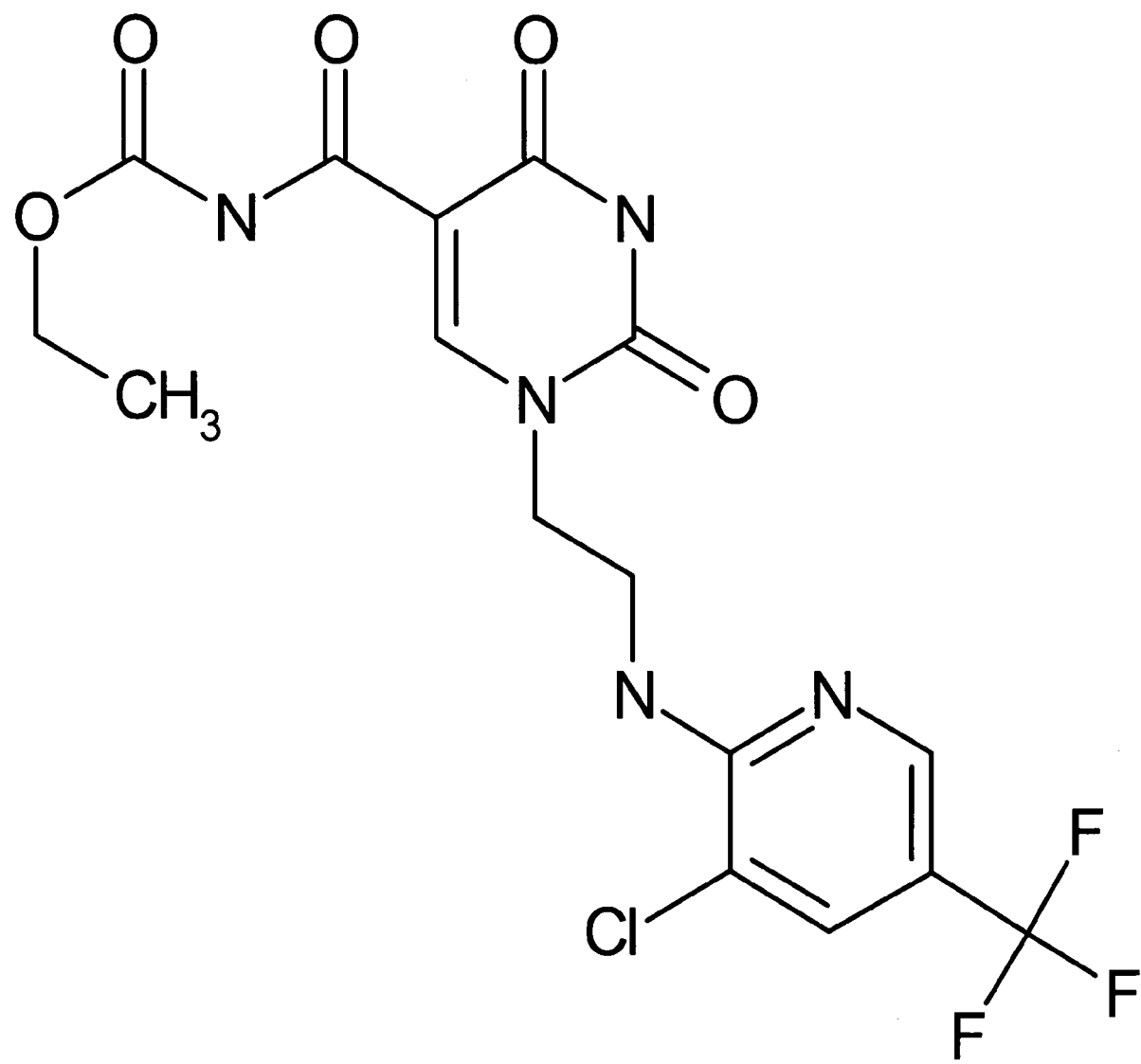
FIG. 10 shows the structure of JFPB.

Mice administered JFPH at various concentrations displayed delayed renal cancer tumor growth compared to control mice that did not receive JFPH (See FIG. 7). Additionally, mice administered 500 nmoles of JFPH displayed a significant reduction of renal cancer metastasis compared to control mice that did not receive JFPH (See FIG. 8). Although an understanding of the mechanism is not necessary to practice the present invention and the present invention is not limited to any particular mechanism of action, in some embodiments, administration of JFPH to a subject enhances the subjects immune system thereby decreasing tumor growth and metastasis in the subject.

All publications and patents mentioned in the above specification are herein incorporated by reference. Various modifications and variations of the described compositions and methods of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in the relevant fields are intended to be within the scope of the present invention.

We claim:

1. A method for stimulating an immune response in a vertebrate comprising administering to said vertebrate a composition comprising: i) JFPB (ethyl N-[[1-(2-[[3-chloro-5-(trifluoromethyl)-2-pyridinyl]amino]ethyl)-2,4-dioxo-1,2,3,4-tetrahydro-5-pyrimidinyl]carbonyl]carbamate) and/or JFPH (4-azocan-1-YL-5,7-dichloro-2-(trifluoromethyl)quinoline), and ii) an antigen.

2. The method of claim 1, wherein said vertebrate has or is at risk of developing cancer.

3. The method of claims 1, wherein said vertebrate is a subject having or at risk of developing an infectious disease or an infection.

4. The method of claim 3, wherein said infection is selected from the group consisting of a bacterial infection, a viral infection, a fungal infection, a yeast infection, a mycobacterial infection, and a parasitic infection.

5. The method of claim 1, wherein said composition is administered in an amount effective to stimulate an immune response.

6. The method of claim 5, wherein said immune response is a cell-mediated immune response.

7. The method of claim 5, wherein said immune response is an adaptive immune response.

8. The method of claim 5, wherein said immune response is a Th1-type immune response.

9. The method of claim 5, wherein said immune response is an antibody mediated immune response.

10. The method of claim 1, wherein said composition is administered in combination with an antibody or antibody fragment.

11. The method of claim 9, wherein said antibody or antibody fragment is specific for a cancer or cancer antigen.

12. The method of claim 9, wherein said antibody or antibody fragment is administered in a sub-therapeutic dose.

13. The method of claim 1, wherein said composition comprises said JFPB (ethyl N-[[1-(2-[[3-chloro-5-(trifluoromethyl)-2-pyridinyl]amino]ethyl)-2,4-dioxo-1,2,3,4-tetrahydro-5-pyrimidinyl]carbonyl]carbamate) and said antigen.

14. The method of claim 1, wherein said composition comprises said JFPH (4-azocan-1-YL-5,7-dichloro-2-(trifluoromethyl)quinoline) and said antigen.

15. A method for stimulating an immune response in a vertebrate comprising administering to said vertebrate a composition comprising JFPH (4-azocan-1-YL-5,7-dichloro-2-(trifluoromethyl)quinoline), wherein said subject has a cancer.

* * * * *

UNITED STATES PATENT AND TRADEMARK OFFICE
CERTIFICATE OF CORRECTION

PATENT NO. : 7,601,355 B2
APPLICATION NO. : 11/444591
DATED : October 13, 2009
INVENTOR(S) : Laurence Howard It is certified that error appears in the above-identified patent and that said Letters Patent is hereby corrected as shown below:

Page 12, column 1, line 8, the Federal Funding should read -- The government has certain rights in the invention.

Signed and Sealed this

Twenty-third Day of March, 2010

David J. Kappos
*Director of the United States Patent and Trademark Office*